US009000132B2

(12) United States Patent
Miller et al.

(10) Patent No.: US 9,000,132 B2
(45) Date of Patent: *Apr. 7, 2015

(54) LIPOPROTEIN-ASSOCIATED PHOSPHOLIPASE A2 ANTIBODY COMPOSITIONS AND METHODS OF USE

(71) Applicant: diaDexus, Inc., South San Francisco, CA (US)

(72) Inventors: Paul Levi Miller, South San Francisco, CA (US); Laura Corral, San Francisco, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/956,139

(22) Filed: Jul. 31, 2013

(65) Prior Publication Data

US 2014/0275485 A1    Sep. 18, 2014

Related U.S. Application Data

(63) Continuation of application No. 13/839,041, filed on Mar. 15, 2013.

(51) Int. Cl.
*C07K 16/40* (2006.01)
*C12N 9/20* (2006.01)
*G01N 33/573* (2006.01)

(52) U.S. Cl.
CPC . *C07K 16/40* (2013.01); *C12N 9/20* (2013.01); *G01N 33/573* (2013.01); *C07K 2317/56* (2013.01)

(58) Field of Classification Search
None
See application file for complete search history.

(56) References Cited

U.S. PATENT DOCUMENTS

| | | |
|---|---|---|
| 3,773,391 A | 11/1973 | Crandall et al. |
| RE30,985 E | 6/1982 | Cartaya |
| 4,485,045 A | 11/1984 | Regen |
| 4,544,545 A | 10/1985 | Ryan et al. |
| 4,560,655 A | 12/1985 | Baker |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,892,538 A | 1/1990 | Aebischer et al. |
| 4,927,762 A | 5/1990 | Darfler |
| 4,975,278 A | 12/1990 | Senter et al. |
| 5,013,556 A | 5/1991 | Woodle et al. |
| 5,091,527 A | 2/1992 | Junius et al. |
| 5,122,469 A | 6/1992 | Mather et al. |
| 5,208,020 A | 5/1993 | Chari et al. |
| 5,229,275 A | 7/1993 | Goroff |
| 5,283,187 A | 2/1994 | Aebischer et al. |
| 5,500,362 A | 3/1996 | Robinson et al. |
| 5,532,152 A | 7/1996 | Cousens et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,573,905 A | 11/1996 | Lerner et al. |
| 5,587,458 A | 12/1996 | King et al. |
| 5,591,669 A | 1/1997 | Krimpenfort et al. |
| 5,605,801 A | 2/1997 | Cousens et al. |
| 5,641,669 A | 6/1997 | Cousens et al. |
| 5,641,870 A | 6/1997 | Rinderknecht et al. |
| 5,648,237 A | 7/1997 | Carter |
| 5,656,431 A | 8/1997 | Cousens et al. |
| 5,698,403 A | 12/1997 | Cousens et al. |
| 5,731,168 A | 3/1998 | Carter et al. |
| 5,739,277 A | 4/1998 | Presta et al. |
| 5,789,199 A | 8/1998 | Joly et al. |
| 5,821,337 A | 10/1998 | Carter et al. |
| 5,837,234 A | 11/1998 | Gentile et al. |
| 5,840,523 A | 11/1998 | Simmons et al. |
| 5,847,088 A | 12/1998 | Cousens et al. |
| 5,869,046 A | 2/1999 | Presta et al. |
| 5,880,273 A | 3/1999 | Adachi et al. |
| 5,977,308 A | 11/1999 | Cousens et al. |
| 5,981,252 A | 11/1999 | MacPhee et al. |
| 6,177,257 B1 | 1/2001 | MacPhee et al. |

(Continued)

FOREIGN PATENT DOCUMENTS

| | | |
|---|---|---|
| EP | 0183070 | 6/1986 |
| EP | 0203089 | 12/1986 |

(Continued)

OTHER PUBLICATIONS

Janeway et al., Immunobiology, 3rd edition, 1997, Garland Press, pp. 3:1-3:11.*
Rudikoff et al., Proc Natl Acad Sci USA, 1982, 79:1979-1983.*
Portolano et al., J. Immunol., 1993, 150:880-887.*
Fundamental Immunology, William E. Paul, M.D. ed., 3d ed. 1993, p. 242.*
Akiyama et al.; Determination of platelet-activating factor acetylhydrolase activity by blotting, beta-radioluminescence, and ultrahigh-sensitivity television camera detection; Analytical Biochemistry; 218(2):295-299; May 1, 1994.
Akiyama et al.; Identification of a Major PAF Acetylhydrolase in Human Serum/Plasma as a 43 kDa Glycoprotein Containing about 9 kDa Asparagine-Conjugated Sugar Chain(s); Journal of Biochemistry; 123(5):786-789; May 1998.

(Continued)

*Primary Examiner* — Michael Szperka
(74) *Attorney, Agent, or Firm* — Shay Glenn LLP

(57) ABSTRACT

The invention provides isolated anti-Lp-PLA2 antibodies that bind to Lp-PLA2. The invention also encompasses compositions comprising an anti-Lp-PLA2 antibody. These compositions can be provided in an article of manufacture or a kit. Another aspect of the invention is an isolated nucleic acid encoding an anti-Lp-PLA2 antibody, as well as an expression vector comprising the isolated nucleic acid. Also provided are cells that produce the anti-Lp-PLA2 antibodies. The invention encompasses a method of producing the anti-Lp-PLA2 antibodies. Other aspects of the invention are a method of detecting an Lp-PLA2 in a subject.

13 Claims, No Drawings

(56) References Cited

U.S. PATENT DOCUMENTS

| | | | |
|---|---|---|---|
| 6,203,790 | B1 | 3/2001 | Cousens et al. |
| 7,217,535 | B2 | 5/2007 | MacPhee et al. |
| 7,301,043 | B2 | 11/2007 | Deigner et al. |
| 7,416,853 | B2 | 8/2008 | MacPhee et al. |
| 7,531,316 | B2 | 5/2009 | Hu et al. |
| 7,741,020 | B2 | 6/2010 | Shou et al. |
| 8,088,886 | B2 | 1/2012 | MacPhee et al. |
| 8,575,348 | B2 | 11/2013 | Rao et al. |
| 8,637,524 | B2 | 1/2014 | Rao et al. |
| 2002/0102231 | A1 | 8/2002 | Dietsch et al. |
| 2003/0072747 | A1 | 4/2003 | Cousens et al. |
| 2003/0148398 | A1 | 8/2003 | MacPhee et al. |
| 2007/0166777 | A1 | 7/2007 | Shou et al. |
| 2007/0281323 | A1* | 12/2007 | Wolfert et al. ............... 435/7.4 |
| 2008/0280829 | A1 | 11/2008 | Shi et al. |
| 2010/0256919 | A1 | 10/2010 | Shou et al. |
| 2011/0280829 | A1 | 11/2011 | David et al. |
| 2012/0276569 | A1 | 11/2012 | Shou et al. |

FOREIGN PATENT DOCUMENTS

| | | |
|---|---|---|
| EP | 0244234 | 11/1987 |
| EP | 0402226 | 12/1990 |
| EP | 0404097 A2 | 12/1990 |
| EP | 0658205 A1 | 6/1995 |
| EP | 0673426 A1 | 9/1995 |
| EP | 0816504 A2 | 1/1998 |
| EP | 0658205 B1 | 3/2000 |
| EP | 0673426 B1 | 6/2001 |
| EP | 1318154 A1 | 6/2003 |
| EP | 1718967 A2 | 11/2006 |
| EP | 1735457 A1 | 12/2006 |
| EP | 2253702 A1 | 11/2010 |
| EP | 2290094 A1 | 3/2011 |
| JP | 4346797 | 12/1992 |
| JP | 6116279 A | 4/1994 |
| JP | 7059597 A | 3/1995 |
| JP | 3036883 B2 | 4/2000 |
| JP | 2002179545 | 6/2002 |
| JP | 2002223794 A | 8/2002 |
| JP | 2004018501 | 1/2004 |
| JP | 4220603 B2 | 2/2009 |
| KR | 10-11411189 B1 | 5/2012 |
| WO | WO81/01145 A1 | 4/1981 |
| WO | WO87/00195 A1 | 1/1987 |
| WO | WO88/07378 A1 | 10/1988 |
| WO | WO90/03430 A1 | 4/1990 |
| WO | WO91/00360 A1 | 1/1991 |
| WO | WO92/20373 A1 | 11/1992 |
| WO | WO93/08829 A1 | 5/1993 |
| WO | WO93/11161 A1 | 6/1993 |
| WO | WO93/16185 A2 | 8/1993 |
| WO | WO93/25673 A1 | 12/1993 |
| WO | WO94/04690 A1 | 3/1994 |
| WO | WO95/09921 A1 | 4/1995 |
| WO | WO96/07321 A1 | 3/1996 |
| WO | WO96/16673 A1 | 6/1996 |
| WO | WO97/38731 A1 | 10/1997 |
| WO | WO98/02463 A1 | 1/1998 |
| WO | WO00/24910 A1 | 5/2000 |
| WO | WO00/32808 A1 | 6/2000 |
| WO | WO00/66567 A1 | 11/2000 |
| WO | WO01/60805 A1 | 8/2001 |
| WO | WO02/30904 A1 | 4/2002 |
| WO | WO02/30911 A1 | 4/2002 |
| WO | WO03/041712 A1 | 5/2003 |
| WO | WO03/086400 A1 | 10/2003 |
| WO | WO03/087088 A2 | 10/2003 |
| WO | WO2004/089184 A2 | 10/2004 |
| WO | WO2005/001416 A2 | 1/2005 |
| WO | WO2005/074604 A2 | 8/2005 |
| WO | WO2005/113797 A2 | 12/2005 |
| WO | WO2011/137419 A1 | 11/2011 |

OTHER PUBLICATIONS

Akiyama et al.; New Serum PAF acetylhydrolase detection method used with the Blotting Method and Beta of 3Hacetyl-PAF; Proceedings of Japanese Conference on the Biochemistry of Lipids; 36:43-46; (year of publication is sufficiently earlier than the effective U.S. filing date and any foreign priority date) 1994; English abstract.

Artsaenko et al.; Expression of a single-chain Fv antibody against abscisic acid creates a wilty phenotype in transgenic tobacco; Plant J; 8(5):745-50; Nov. 1995.

Balafa et al.; Urine of Patients with Nephrotic Syndrome Contains the Plasma Type of PAF-Acetylhydrolase Associated with Lipoproteins; Nephron Physiology; 97(3):45-52; (year of publication is sufficiently earlier than the effective U.S. filing date and any foreign priority date) 2004.

Balestrieri et al.; Measurement of Platelet-Activating Factor Acetylhydrolase Activity by Quantitative High-Performance Liquid Chromatography Determination of Courmarin-Derivatized 1-0-alkyl-2-sn-lysoglyceryl-3-phosphorylcholine; Analytical Biochemistry; 233(2): 145-50; Jan. 1996.

Ballantyne et al.; Lipoprotein-associated phospholipase A2, high-sensitivity C-reactive protein, and risk for incident ischemic stroke in middle-aged men and women in the Atherosclerosis Risk in Communities (ARIC) study; Arch Intern Med.; 165(21):2479-84; Nov. 28, 2005.

Ballantyne et al.; Lipoprotein-associated phospholipase A2, high-sensitivity C-reactive protein, and risk for incident coronary heart disease in middle-aged men and women in the Atherosclerosis Risk in Communities (ARIC) study; Circulation; 109:837-42; Feb. 2004.

Bell et al.; Systematic Screening of the LDL-PLA2Gene for Polymorphic Variants and Case-Control Analysis in Schizophrenia; Biochem and Biophys Res Commun.; 241(3):630-635; Dec. 29, 1997.

BISC 429; BISC 429: Experimental Techniques II Separation Methods. Acid Phosphatase-Enzyme Assay; Siman Fraser University available at www.sfu.ca/bisc/bisc-429/enzymeassay.html#intro, including Image if Google search showing that the document as been available since Jan. 31, 2002.

Blake et al.; Inflammatory bio-markers and cardiovascular risk prediction; J Intern Med; 252(4):283-94; Oct. 2002.

Blankenberg et al.; Plasma PAF-acetylhydrolase in patients with coronary artery disease: results of a cross-sectional analysis; J. Lipid Res.; 44:(7) 1381-1386; May 1, 2003.

Blankenberg et al.; Plasma PAF-acetylhydrolase in patients with coronary artery disease: results of a cross-sectional analysis; J Lipid Res; 44(7):1381-6; Jul. 2003.

Boyd et al.; 2-(Alkylthio)pyrimidin-4-ones as novel, reversible inhibitors of lipoprotein-associated phospholipase A2; Bioorg Med Chem Lett; 10(4):395-398; Feb. 21, 2000.

Boyd et al.; N-1 Substituted Pyrimidin-4-Ones: Novel, Orally Active Inhibitors of Lipoprotein-Associated Phospholipase A2; Bioorg Med Chem Lett; 10(22):2557-2561; Nov. 20, 2000.

Bravata et al.; Thrombolysis for acute stroke in routine clinical practice; Arch Intern Med; 162(17):1994-2001; Sep. 23, 2002.

Brites et al.; Paraoxonase 1 and Platelet-Activating Factor Acetylhydrolase Activities in Patients with Low HDL-Cholesterol Levels with or without Primary Hypertriglyceridemia; Archives of Medical Research; 35(3):235-240; May-Jun. 2004.

Busby et al.; SB-253514 and analogues: novel inhibitors of lipoprotein associated phospholipase A2 produced by *Pseudomonas fluorescens* DSM 11579. II. Physico-chemical properties and structure elucidation; J Antibiot; 53(7):670-6; Jul. 2000.

Caron et al.; Engineered humanized dimeric forms of IgG are more effective antibodies; J Exp Med; 176(4):1191-5; Oct. 1, 1992.

Carter et al.; Humanization of an anti-p185HER2 antibody for human cancer therapy; Proc Natl Acad Sci USA; 89(10):4285-9; May 15, 1992.

Casas et al.; PLA2G7 genotype, lipoprotein-associated phospholipase A2 activity, and coronary heart disease risk in 10 494 cases and 15 624 controls of European Ancestry; Circulation; 121(21):2284-93; Jun. 1, 2010.

Caslake et al.; Lipoprotein-associated Phospholipase A2 platelet-activating factor acetylhydrolase: a potential new risk factor for coronary artery disease; Atherosclerosis; 150(2): 413-9; Jun. 2000.

(56) References Cited

OTHER PUBLICATIONS

Cayman Chemical, Ann Arbor, MI; PAF Acetylhydrolase Assay Kit; Catalog No. 760901; Cayman Chemical Company, Ann Harbor, MI; Jun. 22, 2005.
Chari et al.; Immunoconjugates containing novel maytansinoids: promising anticancer drugs; Cancer Res; 52(1):127-31; Jan. 1, 1992.
Clynes et al.; Fc receptors are required in passive and active immunity to melanoma; Proc Natl Acad Sci USA; 95(2):652-6; Jan. 20, 1998.
Cucchiara et al.; Lipoprotein-associated phospholipase A2 and C-reactive protein for risk-stratification of patients with TIA; Stroke; 40(7):2332-6.; Jul. 2009.
Dada et al; LP-PLA2: an emerging biomarker of coronary heart disease; Expert Review of Molecular Diagnostics; 2(1): 17-22; Jan. 2002.
Davies; The pathophysiology of acute coronary syndromes; Heart; 83:361-6; Mar. 2000.
Deigner et al.; Novel reversible, irreversible and fluorescent inhibitors of plateletactivating factor acetylhydrolase as mechanistic probes; Atherosclerosis; 144(1):79-90; May 1999.
Diadexus Inc.; Enzyme Immunoassay for the Quantitative Determination of Lp-PLA2 in Human Plasma and Serum; Aug. 2005.
Eaton; Cholesterol testing and management: a national comparison of family physicians, general internists, and cardiologists; J Am Board Fam Pract; 11(3):180-6; May-Jun. 1998.
Elkind et al.; High-sensitivity C-reactive protein, lipoprotein-associated phospholipase A2, and outcome after ischemic stroke; Arch Intern Med; 166(19):2073-80; Oct. 23, 2006.
Eppstein et al.; Biological activity of liposome-encapsulated murine interferon gamma is mediated by a cell membrane receptor; Proc Natl Acad Sci USA; 82(11):3688-92; Jun. 1985.
Evan et al.; Isolation of monoclonal antibodies specific for human c-myc proto-oncogene product; Mol Cell Biol; 5(12):3610-6; Dec. 1985.
Field et al.; Purification of a RAS-responsive adenylyl cyclase complex from *Saccharomyces cerevisiae* by use of an epitope addition method; Mol Cell Biol; 8(5):2159-65; May 1988.
Flegar-Mestric et al.; Serum platelet-activating factor acetylhydriolase activity in patients with angiographically established cerebrovascular stenosis; Clinical Chemistry and Laboratory Medicine; Proceesing of the IFFCC-FESCC European Congress; 15'h Barcelona, Spain: 369-372; Publisher Monduzzi Editore, Bologna, Italy; Jun. 1-5, 2003 (Abstract only).
Fujimura et al.; Serum platelet-activating factor acetylhydrolase activity in rats with gastric ulcers induced by water-immersion stress; Scand J Gastroenterol Suppl.; 24(162):59-62; (year of publication is sufficiently earlier than the effective U.S. filing date and any foreign priority date) 1989.
Furie et al.; Lipoprotein-associated phospholipase A2 activity predicts early stroke recurrence [abstract]; Stroke; 38(2):458; Feb. 2007.
Furukawa et al.; Platelet-Activating FactorRInduced Ischemic Bowel Necrosis: The Effect of Platelet-Activating Factor Acetylhydrolase; Pediatr Res.; 34(2):237-41; Aug. 1993.
Glass et al.; Atherosclerosis: The road ahead; Cell; 104:503-16; Feb. 23, 2001.
Gorelick; Lipoprotein-associated phospholipase A2 and risk of stroke; Am J Cardiol; 101(12A):34F-40F; Jun. 16, 2008.
Graham et al.; Characteristics of a human cell line transformed by DNA from human adenovirus type 5; J Gen Virol; 36(1):59-72; Jul. 1977.
Grallert et al.; Eight genetic loci associated with variation in lipoprotein-associated phospholipase A2 mass and activity and coronary heart disease: meta-analysis of genome-wide association studies from five community-based studies; Eur Heart J; 33(2):238-51.; Jan. 2012.
Griffiths et al.; Human anti-self antibodies with high specificity from phage display libraries; EMBO J.; 12(2):725-34; Feb. 1993.
Grissom et al.; Platelet-activating factor acetylhydrolase is increased in lung lavage fluid from patients with acute respiratory distress syndrome; Critical Care Medicine; 31(3):770-775, Mar. 2003.
Guss et al.; Structure of the IgG-binding regions of streptococcal protein; G EMBO J; 5(7):1567-75; Jul. 1986.
Hakkinen et al.; Lipoprotein-associated phospholipase A(2), platelet-activating factor acetylhydrolase, is expressed by macrophages in human and rabbit atherosclerotic lesions; Arterioscler Thromb Vasc Biol; 19(12):2909-17; Dec. 1999.
Hemmings et al.; Platelet-Activating Factor Acetylhydrolase Activity in Peritoneal Fluids of Women with Endometriosis; Obstetrics and Gynecology; 81(2):276-279; Feb. 1993.
Henderson et al.; Recombinant Human Platelet-Activating Factor-Acetylhydrolase Inhibits Airway Inflammation and Hyperreactivity in Mouse Asthma Model; J Immunol; 164(6):3360-3367; Mar. 15, 2000.
Hendrickson et al.; Intramolecularly Quenched BODIPY-Labeled Phospholipids Analogs in Phospholipase A2 and Platelet-Activating Factor Acetylhydrolase assays and in Vivo Fluorescence Imaging; Analytical Biochemistry; 276 (1):27-35; Dec. 1999.
Heron; Deaths: Leading Causes for 2004; Nat'l Vital Stat Rep; 56(5):1-95; Nov. 20, 2007.
Herrmann et al.; Expression of lipoprotein-associated phospholipase A(2) in carotid artery plaques predicts long-term cardiac outcome; Eur Heart J; 30(23):2930-8; Dec. 2009.
Hiramoto et al.; A mutation in plasma platelet-activating factor acetylhydrolase (Val279-->Phe) is a genetic risk factor for stroke; Stroke; 28(12):2417-20; Dec. 1997.
Hoffman et al.; Genetic variants and haplotypes of lipoprotein associated phospholipase A2 and their influence on cardiovascular disease (The Ludwigshafen Risk and Cardiovascular Health Study); J Thromb Haemost; 7(1):41-8; Jan. 2009.
Holliger et al.; Diabodies: small bivalent and bispecific antibody fragments; Proc Natl Acad Sci USA; 90(14):6444-8; Jul. 15, 1993.
Hwang et al.; Hepatic uptake and degradation of unilamellar sphingomyelin/cholesterol liposomes: a kinetic study; Proc Natl Acad Sci USA; 77(7):4030-4; Jul. 1980.
Ibe et al.; Platelet Activating Factor Acetylhydrolase Activity in Lamb Lungs is Up-Regulated in the Immediate Newborn Period; Molecular Genetics and Metabolism; 69(1):46-55; Jan. 2000.
Imaizumi et al.; Activity of platelet-activating factor (PAF) acetylhydrolase in plasma from healthy habitual cigarette smokers; Heart and Vessels; 5(2):81-86; (year of publication is sufficiently earlier than the effective U.S. filing date and any foreign priority date) 1990.
Ito et al.; Serum PAF-Acetylhydrolase (PAF-AH) in Hepatobiliary Disease; Japanese Pharmacology and Therapeutics; 30/Suppl. 2; (year of publication is sufficiently earlier than the effective U.S. filing date and any foreign priority date) 2002.
Ito et al.; Serum PAF-Acetylhydrolase (PAF-AH) in Hepatobiliary Disease; Japanese Pharmacology and Therapeutics; 30/Suppl. 2.; (year of publication is sufficiently earlier than the effective U.S. filing date and any foreign priority date) 2002; Abstract—Science Links Japan (1 page).
Izake et al.; Platelet-activating factor and arachidonic acid metabolites in psoriatic inflammation; Br J Dermatol.; 134(6):1060-4; Jun. 1996.
Jakobovits et al.; Analysis of homozygous mutant chimeric mice: deletion of the immunoglobulin heavy-chain joining region blocks B-cell development and antibody production; Proc Natl Acad Sci USA; 90(6):2551-5; Mar. 15, 1993.
Karkabounas et al.; Quantitative Fluorescence Determination of Phospholipase A2 and PAF Acetylhydrolase in Biological Fluids using High Performance Liquid Chromatography; Chemistry and Physics of Lipids; 130(1):69-70; Jun. 2004.
Karlan Research Products Corporation, Santa Rosa, CA; Auto PAF-AH Serum (plasma) platelet-activating factor (PAF) acetylhydrolase assay—Instruction Manual; (date of publication unknown; available to applicants at least as of Sep. 16, 2005).
Kawamura,Y.; A Simple Measurement of Plasma Platelet-Activating Factor (PAF) Acetylhydrolase, Normal Level Activity, and Distribution Among Lipoprotein Fractions; Japanese Journal of Clincal Pathology; 35(10)1149-1153; Oct. 1987.
Kawamura,Y.; A Simple Measurement of Plasma Platelet-Activating Factor (PAF) Acetylhydrolase, Normal Level Activity, and Distribu-

(56) References Cited

OTHER PUBLICATIONS tion Among Lipoprotein Fractions; Japanese Journal of Clinical Pathology; 35(10):1149-1153; Oct. 1987; Abstract- HCAPLUS (1 Page).
Khovidhunkit et al.; Plasma platelet-activating factor acetylhydrolase activity in human immunodeficiency virus infection and the acquired immunodeficiency syndrome; Metabolism.; 48(12):1524-31; Dec. 1999.
Kirschbaum B.; Platelet Activating Factor Acetylhydrolase activity in the urine of patients with renal disease; Clinical Chimica Acta; 199(2):139-146; Jun. 14, 1991.
Kitsiouli et al.; Differential Determination of Phospholipase A2 ane P AFAcetylhydrolase in Biological Fluids Using Fluorescent Substrates; Journal of Lipid Research; 40(12):2346-2356; Dec. 1999.
Koenig et al.; Lipoprotein-Associated Phospholipase A2 Adds to Risk Prediction of Incident Coronary Events by C-Reactive Protein in Apparently Healthy Middle-Aged Men from the General Population; Circulation; 110(14):1903-1908; Oct. 2004.
Kosaka et al.; Serum platelet-activating factor acetylhydrolasse (PAF-AH) activity in more than 3000 healthy Japanese; Clinica Chimica Acta; 313(1-2):179-183; Oct. 2001.
Kosaka et al.; Spectrophotometric Assay for Serum Platelet-Activating Factor Acetylhydrolase Activity; Clinica Chimica Acta; 296(1-2):151-161; Jun. 2000.
Kruse et al.; The Ile198Thr and Ala379Val variants of plasmatic PAF-acetylhydrolase impair catalytical activities and are associated with atopy and asthma; Am J Hum Genet; 66(5):1522-30; May 2000.
Kujiraoka et al.; Altered Distribution of Plasma PAF-AH between HDLs and other Lipoproteins in Hyperlipidemia and Diabetes Mellitus; Journal of Lipid Research; 44(10):2006-14; Oct. 2003.
Lindahl et al.; Markers of myocardial damage and inflammation in relation to long-term mortality in unstable coronary artery disease. FRISC Study Group. Fragmin during Instability in Coronary Artery Disease; N Engl J Med; 343(16):1139-47; Oct. 19, 2000.
Lutz-Freyermuth et al.; Quantitative determination that one of two potential RNA-binding domains of the A protein component of the U1 small nuclear ribonucleoprotein complex binds with high affinity to stem-loop II of U1 RNA; Proc Natl Acad Sci USA; 87(16):6393-7; Aug. 1990.
MacPhee et al.; Lipoprotein-associated phospholipase A2, platelet-activating factor acetylhydrolase, generates two bioactive products during the oxidation of low-density lipoprotein: use of a novel inhibitor; Biochem J; 338:479-87; Mar. 1, 1999.
Martin et al.; Irreversible coupling of immunoglobulin fragments to preformed vesicles. An improved method for liposome targeting; J Biol Chem; 257(1):286-8; Jan. 10, 1982.
Mather; Establishment and characterization of two distinct mouse testicular epithelial cell lines; Biol Reprod; 23(1):243-52; Aug. 1980.
Matsuzaki, Masaharu; Measurement Methods of Platelet Activating Factor (PAF) and PAF Acetylhydrolase (PAFAH) Activity; SRL Hokan; 13(3): 36-41; (year of publication is sufficiently earlier than the effective U.S. filing date and any foreign priority date) 1989; English translation of introduction.
McManus et al.; PAF, a Putative Mediator of Oral Inflammation; Crit Rev Oral Biol Med.; 11(2):240-258; (year of publication is sufficiently earlier than the effective U.S. filing date and any foreign priority date) 2000.
Min et al., Platelet-Activating Factor Acetylhydrolases:? Broad Substrate Specificity and Lipoprotein Binding Does Not Modulate the Catalytic Properties of the Plasma Enzyme; Biochemistry; 40(15): 4539-4549; Apr. 17, 2001.
Miwa et al.; "Serum platelet-activating factor (PAF) acetylhydrolase of children with bronchial asthma," Japanese Journal of Inflammation; 8 (4):327- 333; Dec. 1988; Abstract—HCAPLUS (1 Page).
Miwa et al.; Characterization of serum platelet-activating factor (PAF) acetylhydrolase. Correlation between deficiency of serum P AF acetylhydrolase and respiratory symptoms in asthmatic children; Journal of Clinical Investigation; 82(6): 1983-1991; Dec. 1988.
Miwa et al.; On Development of a Measurement Method of Serum PAF Acetylhydrolase Activity Using an Automatic Analyser, and the Clinical Significance of Serum PAF Acetylhydrolase Defect; Proceedings of Japanese Conference on the Biochemistry of Lipids; 34:305-308; (year of publication is sufficiently earlier than the effective U.S. filing date and any foreign priority date) 1992; English Abstract.
Miwa et al.; Serum platelet-activating factor (PAF) acetylhydrolase of children with bronchial asthma; Japanese Journal of Inflammation; 8(4):327-333; Dec. 1988.
Morrison et al.; Chimeric human antibody molecules: mouse antigen-binding domains with human constant region domains; Proc Natl Acad Sci USA; 81*21):6851-5; Nov. 1984.
Muguruma et al.; the central role of PAF in necrotizing enterocolitis development; Adv Exp Med Biol.; 407:379-82; (year of publication is sufficiently earlier than the effective U.S. filing date and any foreign priority date) 1997.
No authors listed, Thrombolytic therapy with streptokinase in acute ischemic stroke. The Multicenter Acute Stroke Trial-Europe Study Group; N Engl J Med; 335(3): 145-50; Jul. 18, 1996.
No authors listed, Tissue plasminogen activator for acute ischemic stroke. The National Institute of Neurological Disorders and Stroke rt-PA Stroke Study Group; N Engl J. Med; 333(24): 1581-7; Dec. 14, 1995.
Packard et al.; Lipoprotein-associated phospholipase A2 as an independent predictor of coronary heart disease; N Engl J Med; 343(16):1148-55; Oct. 19, 2000.
Patrick et al.; Reduced PAF-Acetyihydrolase Activity is Associated with Postinjury Multiple Organ Failure; Shock; 7(3):170-174; Mar. 1997.
Pritchard et al.; The Degradation of Platelet-Activating Factor in the Plasma of a Patient with Familial High Density Lipoprotein Deficiency (Tangier Disease); Blood; 66(6):1476-1478; Dec. 1985.
Rattan et al., Protein synthesis, posttranslational modifications, and aging, Ann N Y Acad Sci.; 663:48-62; Nov. 21, 1992.
Ridker et al.; Comparison of C-reactive protein and low-density lipoprotein cholesterol levels in the prediction of first cardiovascular events; N Engl J Med; 347(20):1557-65; Nov. 14, 2002.
Riehl et al.; Platelet-activating factor acetylhydrolases in Caco-2 cells and epithelium of normal and ulcerative colitis patients; Gastroenterology; 109(6): 1826-1834; Dec. 1995.
Rosamond et al.; Heart disease and stroke statistics-2008 update: a report from the American Heart Association Statistics Committee and Stroke Statistics Subcommittee; Circulation; 117(4):e25-146; Jan. 29, 2008.
Santos et al.; Relation of markers of inflammation (C-reactive protein, white blood cell count, and lipoprotein-associated phospholipase A2) to the ankle-brachial index; Vasc Med; 9(3):171-6; May 2004.
Saougos et al.; Differential effect of hypolipidemic drugs on lipoprotein-associated phospholipase A2; Arterioscler Thromb Vasc Biol; 27(10):2236-43; Oct. 2007.
Sarchielli et al.; Platelet-Activating Factor (PAF) in Internal Jugular Venous Blood of Migraine without Aura Patients Assessed During Migraine Attacks; Cephalagia; 24(8):623-630; Aug. 2004.
Satoh et al.; Plasma platelet-activating factor acetylhydrolase deficiency in Japanese patients with asthma; Am J Respir Crit Care Med.; 159(3):974-9; Mar. 1999.
Satoh et al.; Platelet-activating factor acetylhydrolase in plasma lipoproteins from patients with ischemic stroke; Stroke; 23(8); pp. 1090-1092; Aug. 1992.
Satoh et al; Platelet-activating factor (PAF) acetylhydrolase and plasma lipoproteins: Relative distribution of the activity among lipoprotein classes; Journal of Japan Atherosclerosis Society; 16(4):501-504; (year of publication is sufficiently earlier than the effective U.S. filing date and any foreign priority date) 1988.
Schindler et al.; Fluorophore-labeled ether lipids: substrates for enzymes of the plateletactivating factor cycle in peritoneal polymorphonuclear leukocytes; Analytical Biochemistry; 174(2):477-84; Nov. 1, 1988.
Seifter et al.; Analysis for protein modifications and nonprotein cofactors; Methods Enzymol.;182:626-46; (year of publication is sufficiently earlier than the effective U.S. filing date and any foreign priority date) 1990.

(56) References Cited

OTHER PUBLICATIONS

Serebruany et al.; Depressed Plasma Platelet- Activating Factor Acetylhydrolasein Patients Presenting with Acute Myocardial Infarction; Cardiology; 90(2):127-130; Oct. 1998.
Servillo et al.; Simultaneous Determination of Lysophospholipids by High-performance Liquid Chromatography with Fluorescence Detection; Journal of Chromatography; 689(2):281-286; Feb. 1997.
Shalaby et al.; Development of humanized bispecific antibodies reactive with cytotoxic lymphocytes and tumor cells overexpressing the HER2 protooncogene; J Exp Med; 175(1):217-25; Jan. 1, 1992.
Skinner et al.; Use of the Glu-Glu-Phe C-terminal epitope for rapid purification of the catalytic domain of normal and mutant ras GTPase-activating proteins; J Biol Chem; 266(22):14163-6; Aug. 5, 1991.
Stafforini et al.; Human macrophages secrete platelet-activating factor acetylhydrolase; Journal of Biological Chemistry; 265(17); pp. 9682-9687; Jun. 1990.
Song et al.; Sequencing of Lp-PLA2-encoding PLA2G7 gene in 2000 Europeans reveals several rare loss-of-function mutations; Pharmacogenomics J; 12(5):425-31; Oct. 2012.
Stafforini et al.; Human Plasma Platelet-Activating Factor Acetylhyrolase. Purification and Properties; Journal of Biological Chemistry; 262(9):4223-4230; Mar. 25, 1987.
Stafforini et al.; Platelet-Activating Factor Acetylhydrolase in Human erythrocytes; Methods in Enzymology; 197:411-425; (year of publication is sufficiently earlier than the effective U.S. filing date and any foreign priority date) 1991.
Stafforini et al.; Platelet-activating Factor Acetylhydrolases; J. Biol. Chem.; 272(29): 17895-17898; Jul. 18, 1997.
Stremler et al.; An oxidized derivative of phosphatidylcholine is a substrate for the platelet-activating factor acetylhydrolase from human plasma; J. Biological Chemistry; 264(10); pp. 5331-5334; Apr. 1989
Tew et al.; Mechanism of Inhibition of LDL Phospholipase A2 by Monocyclic-?-lactams. Burst Kinetics and the Effect of Stereochemistry; Biochemistry; 37(28):10087-10093; Jul. 14, 1998.
Tew et al.; Purification, Properties, Sequencing, and Cloning of a Lipoprotein-Associated, Serine-Dependent Phospholipase Involved in the Oxidative Modification of Low-Density Lipoproteins; Arterioscler Thromb Vasc Biol. 16(4):591-599; Apr. 1996.
Thirkettle et al.; SB-253514 and Analogues; Novel Inhibitors of Lipoprotein-Associated Phospholipase A2 Produced by *Pseudomonas fluorescens* DSM 11579; J. Antibiotics; vol. 53(7):664-669; Jul. 2000.
Thirkettle, Jan; SB-253514 and Analogues; Novel Inhibitors of Lipoprotein Associated Phospholipase A2 Produced by *Pseudomonas fluorescens* DSM 11579. III. Biotransformation Using Naringinase; J. Antibiotics; vol. 53(7):733-735; Jul. 2000.
Tjoelker et.; Anti-inflammatory properties of a platelet-activating factor acetylhydrolase; Nature 374, 549-553; Apr. 6, 1995.
Traunecker et al.; Bispecific single chain molecules (Janusins) target cytotoxic lymphocytes on HIV infected cells; EMBO J; 10(12):3655-9; Dec. 1991.
Tselepis et al.; Association of the inflammatory state in active juvenile rheumatoid arthritis with hypoRhigh-density lipoproteinemia and reduced lipoprotein-associated platelet-activating factor acetylhydrolase activity; Arthritis Rheum.; 42(2):373R383, Feb. 1999.
Tselepis et al.; Inflammation, bioactive lipids and atherosclerosis: potential roles of a lipoprotein-associated phospholipase A2, platelet activating factor-acetylhydrolase; Atheroscler Suppl.; 3(4):57-68; Dec. 2002.
Tsuji et al.; The presence of platelet-activating factor-acetylhydrolase in human middle ear effusions; ORL J Otorhinolaryngol Relat Spec.; 60(1):25-9; Jan.-Feb. 1998.
Tsukioka et al.; Increased Plasma Level of Platelet-Activating Factor (PAF) and Decreased Serum PAF etylhydrolase (PAFAH) Activity in Adults with Bronchial Asthma; Journal of Investigational Allergology and Clinical Immunology; 6(1):22-29; Jan.-Feb. 1996.

Unno et al.; Single Nucleotide Polymorphism (G994?T) in the Plasma Platelet-Activating Factor-Acetylhydrolase Gene is Associated with Graft Patency of Femoropopliteal Bypass; Surgery; 132(1):66-71; Jul. 2002.
Urlaub et al.; Isolation of Chinese hamster cell mutants deficient in dihydrofolate reductase activity; Proc Natl Acad Sci USA; 77(7):4216-20; Jul. 1980.
Washburn et al.; Novel general approach for the assay and inhibition of hydrolytic enzymes utilizing suicide-inhibitory bifunctionally linked substrates (SIBLINKS): Exemplified by a phospholipase A2 assay; J. Am. Chem. Soc.; 112; pp. 2040-2041; Feb. 1990.
Washburn et al.; Suicide-inhibitory bifunctionally linked substrates (SIBLINKS) as phospholipase A2 inhibitors; J. Biological Chemistry; 266(8); pp. 5042-5048; Mar. 1991.
Waterhouse et al.; Combinatorial infection and in vivo recombination: a strategy for making large phage antibody repertoires; Nucleic Acids Res; 21(9):2265-6; May 11, 1993.
Winkler et al.; Fluvastatin slow-release lowers platelet-activating factor acetyl hydrolase activity: a placebo-controlled trial in patients with type 2 diabetes; J Clin Endocrinol Metab; 89(3):1153-9; Mar. 2004.
Wold, Finn; Posttranslational Protein Modifications: Perspectives and Prospects; Posttranslational Covalent Modification of Proteins; B.C. Johnson, Ed.; Academic Press, New York; pp. 1-12; (year of publication is sufficiently earlier than the effective U.S. filing date and any foreign priority date) 1983.
Wolff et al.; Monoclonal antibody homodimers: enhanced antitumor activity in nude mice; Cancer Res.; 53(11):2560-5; Jun. 1, 1993.
Yoon et al.; Interdependent effect of angiotensin-converting enzyme and platelet-activating factor acetylhydrolase gene polymorphisms on the progression of immunoglobulin A nephropathy; Clinical Genetics; 62(2):128-134; Aug. 2002.
Yoshida et al.; Platelet-activating factor acetylhydrolase in red cell membranes. Does decreased activity impair erythrocyte deformability inischemic stroke patients?; Stroke; 24(1); pp. 14-18; Jan. 1993.
Zalewski et al.; Role of Lipoprotein-Associated Phospholipase A2 in Atherosclerosis. Biology, Epidemiology, and Possible Therapeutic Target; Arterioscler Thromb Vasc Biol; 25(5):923-931; May 2005.
NCBI RefSeqID: NM_001168357; *Homo sapiens* phospholipase A2, group VII (platelet-activating factor acetylhydrolase, plasma) (PLA2G7), transcript variant 2, mRNA; www.ncbi.nlm.nih.gov/nuccore/ NM_001168357.1?report=gbwithparts&log$=seqview; 5pgs; downloaded Aug. 27, 2013.
NCBI RefSeqID: NP_005075; platelet-activating factor acetylhydrolase precursor [*Homo sapiens*]; http://www.ncbi.nlm.nih.gov/protein/ NP_005075.3; 3pgs; downloaded Aug. 27, 2013.
NCBI RefSeqID: NM_005084; *Homo sapiens* phospholipase A2, group VII (platelet-activating factor acetylhydrolase, plasma) (PLA2G7), transcript variant 1, mRNA; http://www.ncbi.nlm.nih.gov/nuccore/ NM_005084; 5pgs; ; downloaded Aug. 27, 2013.
NCBI RefSeqID: NP_001161829; platelet-activating factor acetylhydrolase precursor [*Homo sapiens*]; http://www.ncbi.nlm.nih.gov/protein/NP_001161829; 3pgs; downloaded Aug. 27, 2013.
NCNI Entrez GeneID: 7941 (PLA2G7); PLA2G7 phospholipase A2, group VII (platelet-activating factor acetylhydrolase, plasma) [ *Homo sapiens* (human) ]; http://www.ncbi.nlm.nih.gov/gene/7941; 9pgs; downloaded Aug. 27, 2013.
Miller et al.; U.S. Appl. No. 13/839,041 entitled "Lipotrotein-associated phospholipase A2 antibody composition and methods of use," filed Mar. 15, 2013.
Blake et al.; A prospective evaluation of lipoprotein-associated phospholipase A(2) levels and the risk of future cardiovascular events in women; J Am Coll Cardiol.; 1;38(5):1302-1306; Nov. 2001.
Chothia et al.; Canonical structures for the hypervariable regions of immunoglobulins; J Mol Biol; 196(4):901-917; Aug. 20, 1987.
Chothia et al.; Structural repertoire of the human VH segments; J Mol Biol; 227(3):799-817; Oct. 5, 1992.
Clark et al.; Recombinant tissue-type plasminogen activator (Alteplase) for ischemic stroke 3 to 5 hours after symptom onset; The ATLANTIS Study: a randomized controlled trial. Alteplase Thrombolysis for Acute Noninterventional Therapy in Ischemic Stroke'JAMA; 282(21):2019-2026; Dec. 1, 1999.

(56) References Cited

OTHER PUBLICATIONS

Expert Panel on Detection, Evaluation, and Treatment of High Blood Cholesterol in Adults; Executive Summary of the Third Report of the National Cholesterol Education Program (NCEP) Expert Panel on Detection, Evaluation, and Treatment of High Blood Cholesterol in Adults (Adult Treatment Panel III); JAMA; 285(19):2486-2497; May 16, 2001.
Hopp et al.; A Short Polypeptide Marker Sequence Useful for Recombinant Protein Identification and Purification; Nature Biotechnology; 6:1204-10; Oct. 1988.
Katzan et al.; Use of tissue-type plasminogen activator for acute ischemic stroke: The Cleveland area experience; JAMA; 283(9):1151-8; Mar. 1, 2000.
Lusis; Atherosclerosis; Nature; 407(6801):233-41; Sep. 14, 2000 (Author Manuscript).
Marks et al.; By-passing immunization. Human antibodies from V-gene libraries displayed on phage; J Mol Biol; 222(3):581-597; Dec. 5, 1991.
Martin et al.; GAP domains responsible for ras p21-dependent inhibition of muscarinic atrial K+ channel currents; Science; 255(5041):192-194; Jan.10, 1992.
Morimoto et al.; Single-step purification of F(ab')2 fragments of mouse monoclonal antibodies (immunoglobulins G1) by hydrophobic interaction high performance liquid chromatography using TSKgel Phenyl-5PW; J Biochem Biophys Methods; 24(1-2):107-17; Mar. 1992.
Muhlestein et al.; The reduction of inflammatory biomarkers by statin, fibrate, and combination therapy among diabetic patients with mixed dyslipidemia; The DIACOR (Diabetes and Combined Lipid Therapy Regimen) study, J Am Coll Cardiol.; 48(2):396-401; Jul. 18, 2006.
Oei et al.; Lipoprotein-associated phospholipase A2 is associated with risk of coronary heart disease and stroke; The Rotterdam Study ( ) European Society of Cardiology Congress 2004; pp. 570-575; Aug.-Sep. 2004.
Riechmann et al.; Reshaping human antibodies for therapy; Nature; 332 (6162):323-7; Mar. 24, 1988.
Rosensen; Fenofibrate reduces lipoprotein associated phospholipase A2 mass and oxidative lipids in hypertriglyceridemic subjects with the metabolic syndrome; Am Heart J.; 155(3):499.e.9-499.e16; Mar. 2008.
Smith et al.; Identification of common molecular subsequences; J Mol Biol; 147(1):195-197; Mar. 25, 1981.
Albert et al.; The effect of statin therapy on lipoprotein associated phospholipase A2 levels; Atherosclerosis; 182(1):193-198; Sep. 2005.
Alberts et al.; Risk of Stroke and Elevated Levels of Lipoprotein-Associated Phospholipase A2, Abstracts From the 2008 International Stroke Conference; Stroke; 39(2):642; Feb. 2008.
Anderson; Human gene therapy; Science; 256(5058):808-813; May 8, 1992.
Barnes et al.; Methods for growth of cultured cells in serum-free medium; Anal Biochem; 102(2):255-270; Mar. 1, 1980.
Blackie et al.; The identification of clinical candidate SB-480848: a potent inhibitor of lipoprotein-associated phospholipase A2; Bioorg Med Chem Lett.; 13(6):1067-1070; Mar. 23, 2003.
Bloomer et al.; 1-(Arylpiperazinylamidoalkyl)-pyrimidones: orally active inhibitors of lipoprotein-associated phospholipase A(2); Bioorg Med Chem Lett.; 11(14):1925-1929; Jul. 23, 2001.
Boyd et al.; Potent, orally active inhibitors of lipoprotein-associated phospholipase A(2): 1-(biphenylmethylamidoalkyl)-pyrimidones; Bioorg Med Chem Lett.; 12(1):51-55; Jan. 7, 2002.
Boyd et al.; The identification of a potent, water soluble inhibitor of lipoprotein-associated phospholipase A2; Bioorg Med Chem Lett.; 11(5):701-704; Mar. 12, 2001.
Brennan et al.; Preparation of bispecific antibodies by chemical recombination of monoclonal immunoglobulin G1 fragments; Science; 229(4708):81-83; Jul. 5, 1985.
Brodeur et al.; (Chap. 4) Mouse-human myeloma partners for the production of heterohybridomas; in Monoclonal Antibody Production Techniques and Applications; Marcel Dekker, Inc., New York; pp. 51-63; -'1987(year of pub. sufficiently earlier than effective US filing date and any foreign priority date).
Brüggemann et al.; Designer mice: the production of human antibody repertoires in transgenic animals; Year Immunol; 7:33-40; Feb. 1993.
Capel et al.; Heterogeneity of human IgG Fc receptors; Immunomethods; 4 (1):25-34; Feb. 1994.
Carpenter et al.; Inhibition of lipoprotein-associated phospholipase A2 diminishes the death-inducing effects of oxidised LDL on human monocyte-macrophages; FEBS Lett.; 505(3):357-63; Sep. 21, 2001.
Carter et al.; High level *Escherichia coli* expression and production of a bivalent humanized antibody fragment; Biotechnology; 10(2):163-167; Feb. 1992.
Chothia et al.; Structural determinants in the sequences of immunoglobulin variable domain; J Mol Biol; 278(2):457-479; May 1, 1998.
Clackson et al.; Making antibody fragments using phage display libraries; Nature; 352(6336):624-628; Aug. 15, 1991.
Cunningham et al.; High-resolution epitope mapping of hGH-receptor interactions by alanine-scanning mutagenesis; Science; 244(4908):1081-1085; Jun. 2, 1989.
Daeron; Fc receptor biology; Annu Rev Immunol; 15:203-234; Apr. 1997.
De Haas et al.; Fc gamma receptors of phagocytes; J Lab Clin Med; 126 (4):330-341; Oct. 1995.
Donnan et al.; Streptokinase for acute ischemic stroke with relationship to time of administration; Australian Streptokinase (ASK) Trial Study Group, JAMA. 276(12):961-966; Sep. 25, 1996.
Fecker et al.; Expression of single-chain antibody fragments (scFv) specific for beet necrotic yellow vein virus coat protein or 25 kDa protein in *Escherichia coli* and *Nicotiana benthamiana*; Plant Mol Biol; 32 (5):979-986; Dec. 1996.
Fraker et al.; Protein and cell membrane iodinations with a sparingly soluble chloroamide, 1,3,4,6-tetrachloro-3a,6a-diphrenylglycoluril; Biochem Biophys Res Commun; 80:849-857; Feb. 28,1978.
Gabizon et al.; Pharmacokinetics and tissue distribution of doxorubicin encapsulated in stable liposomes with long circulation times; J Natl Cancer Inst; 81(19):1484-1488; Oct. 4, 1989.
Gazzano-Santoro et al.; A non-radioactive complement-dependent cytotoxicity assay for anti-CD20 monoclonal antibody; J Immunol Methods; 202(2):163-171; Mar. 28, 1997.
Goding; Monoclonal Antibodies: Principles and Practice; Academic Press; pp. 103; 1986 (year of pub. sufficiently earlier than effective US filing date and any foreign priority date).
Goodman et al.; (Chap. 6) Immunoglobulin Proteins; in Stites et al. (eds.); Basic and Clinical Immunology, 8th Ed.; Appleton & Lange, Norwalk, CT.; pp. 66-79; Jan. 1, 1994.
Gruber et al.; Efficient tumor cell lysis mediated by a bispecific single chain antibody expressed in *Escherichia coli*; J Immunol; 152(11):5368-5374; Jun. 1, 1994.
Guyer et al.; Immunoglobulin binding by mouse intestinal epithelial cell receptors; J Immunol; 117(2):587-593; Aug. 1976.
Hacke et al.; Intravenous thrombolysis with recombinant tissue plasminogen activator for acute hemispheric stroke; The European Cooperative Acute Stroke Study (ECASS), JAMA; 274(13):1017-1025; Oct. 4, 1995.
Hacke et al.; Randomised double-blind placebo-controlled trial of thrombolytic therapy with intravenous alteplase in acute ischaemic stroke (ECASS II); Lancet; 352(9136):1245-1251; Oct. 17, 1998.
Ham et al.; Media and growth requirements; Methods Enzymol; 58:44-93; 1979 (year of pub. sufficiently earlier than effective US filing date and any foreign priority date).
Hiatt et al.; Production of antibodies in transgenic plants; Nature; 342 (6245):76-78; Nov. 2, 1989.
Jakobovits et al.; Germ-line transmission and expression of a human-derived yeast artificial chromosome; Nature; 362(6417):255-258; Mar. 18, 1993.
Johnson et al.; Human antibody engineering; Curr Opin Struct Biol; 3 (4):564-571; Aug. 1993.
Jones et al.; Replacing the complementarity-determining regions in a human antibody with those from a mouse; Nature; 1321(6069):522-525; May 1986.

(56) References Cited

OTHER PUBLICATIONS

Kearney et al.; A new mouse myeloma cell line that has lost immunoglobulin expression but permits the construction of antibody-secreting hybrid cell lines; J Immunol; 123(4):1548-1550; Oct. 1979.
Köhler et al.; Continuous cultures of fused cells secreting antibody of predefined specificity; Nature; 256(5517):495-497; Aug. 7, 1975.
Kostelny et al.; Formation of a bispecific antibody by the use of leucine zippers; J Immunol; 148(5):1547-1553; Mar. 1, 1992.
Kozbor et al.; A human hybrid myeloma for production of human monoclonal antibodies; J Immunol; 133(6):3001-3005; Dec. 1984.
Kuvin et al.; Effects of extended-release niacin on lipoprotein particle size, distribution, and inflammatory markers in patients with coronary artery disease; Am J Cardiol.; 98(6):743-745; Sep. 15, 2006.
Leach et al.; Lipoprotein-associated PLA2 inhibition—a novel, non-lipid lowering strategy for atherosclerosis therapy; Farmaco.; 56(1-2):45-50; Jan.-Feb. 2001.
Libby et al.; Macrophages and atherosclerotic plaque stability; Curr Opin Lipidol.; 7(5):330-335; Oct. 1996.
Lindmark et al.; Binding of immunoglobulins to protein A and immunoglobulin levels in mammalian sera; J Immunol Methods; 62(1):1-13; Aug. 12, 1983.
MacPhee; Lipoprotein-associated phospholipase A2: a potential new risk factor for coronary artery disease and a therapeutic target; Curr Opin Pharmaco;. 1(2):121-125; Apr. 2001.
Marks et al.; By-passing immunization: building high affinity human antibodies by chain shuffling; Biotechnology; 10(7):779-783; Jul. 1992.
MAST-I Group (Italy); Randomised controlled trial of streptokinase, aspirin, and combination of both in treatment of acute ischaemic stroke. Multicentre Acute Stroke Trial—Italy (MAST-I) Group; Lancet; 346(8989):1509-1514; Dec. 9, 1995.
Mather et al.; Culture of testicular cells in hormone-supplemented serum-free medium; Ann N Y Acad Sci; 383:44-68; Jun. 1982.
McAfferty et al.; Phage antibodies: filamentous phage displaying antibody variable domains; Nature; 348(6301):552-554; Dec. 6, 1990.
Miller et al.; Epitope binning of murine monoclonal antibodies by a multiplexed pairing assay; J Immunol Methods; 365(1-2):118-125; Feb. 28, 2011.
Milstein et al.; Hybrid hybridomas and their use in immunohistochemistry; Nature; 305:537-540; Oct. 1983.
Munson et al.; Ligand: a versatile computerized approach for characterization of ligand-binding systems; Anal Biochem; 107(1):220-239; Sep. 1, 1980.
National Institute of Health (NIH), Clinical Guidelines on the Identification, Evaluation, and Treatment of Overweight and Obesity in Adults; Sep. 1998.
Neuberger et al.; Recombinant antibodies possessing novel effector functions; Nature; 312:604-608; Dec. 1984.
Owen et al.; Synthesis of a functional anti-phytochrome single-chain Fv protein in transgenic tobacco; Biotechnology; 10(7):790-794; Jul. 1992.
Paborsky et al.; Mammalian cell transient expression of tissue factor for the production of antigen; Protein Eng; 3(6):547-553; May 1990.
Pearson; Searching protein sequence libraries: comparison of the sensitivity and selectivity of the Smith-Waterman and FASTA algorithms; Genomics; 11(3):635-650; Nov. 1991.
Pinto et al.; Natural product derived inhibitors of lipoprotein associated phospholipase A2, synthesis and activity of analogues of SB-253514; Bioorg Med Chem Lett.; 10(17):2015-2017; Sep. 4, 2000.
Plückthun; Chap. 11: Antibodies from *escherichia coli*; in: Rosenberg et al.; The Pharmacology of Monoclonal Antibodies, vol. 113; Springer-Verlag; New York, NY; pp. 269-315; 1994 (year of pub. sufficiently earlier than effective US filing date and any foreign priority date).
Plückthun; Mono- and bivalent antibody fragments produced in *Escherichia coli*: engineering, folding and antigen binding; Immunol Rev; 130:151-188; Dec. 1992.
Presta et al.; Humanization of an antibody directed against IgE; J Immunol; 151(5):2623-2632; Sep. 1, 1993.
Presta; Antibody engineering; Curr Opin Struc Biol; 2(4):593R596; Aug. 1992.
Ravetch et al.; Fc receptors; Annu Rev Immunol; 9:457-492; Apr. 1991.
Sandercock et al.; Antiplatelet therapy for acute ischaemic stroke. Cochrane Database of Systematic Reviews 2008, Issue 3. Jul. 2008.
Schaefer et al.; Effects of atorvastatin versus other statins on fasting and postprandial C-reactive protein and lipoprotein-associated phospholipase A2 in patients with coronary heart disease versus control subjects; Am J Cardiol; 95(9):1025-1032; May 1, 2005.
Shopes; A genetically engineered human IgG mutant with enhanced cytolytic activity; J Immunol; 148(9):2918-2922, May 1, 1992.
Sims et al.; A humanized CD18 antibody can block function without cell destruction; J Immunol; 151(4):2296-2308; Aug. 15, 1993.
Skerra; Bacterial expression of immunoglobulin fragments; Curr Opin Immunol; 5(2):256-62; Apr. 1993.
Stevenson et al.; A chimeric antibody with dual Fc regions (bisFabFc) prepared by manipulations at the IgG hinge; Anticancer Drug Des; 3(4):219-30; Mar. 1989.
Strong et al.; Preventing stroke: saving lives around the world; Lancet Neurol.; 6(2):182-7; Feb. 2007.
Suckling et al.; Lipoprotein-associated phospholipase A2: a target directed at the atherosclerotic plaque; Expert Opin Ther Targets.; 6(3):309-314; Jun. 2002.
Suresh et al.; Bispecific monoclonal antibodies from hybrid hybridomas; Methods Enzymol; 121:210-228; 1986 (year of pub. sufficiently earlier than effective US filing date and any foreign priority date).
Tutt et al.; Trispecific F(ab')3 derivatives that use cooperative signaling via the TCR/CD3 complex and CD2 to activate and redirect resting cytotoxic T cells; J Immunol; 147(1):60-9; Jul. 1, 1991.
Verhoeyen et al.; Reshaping human antibodies: grafting an antilysozyme activity; Science; 239(4847):1534-6; Mar. 25, 1998.
Wardlaw et al.; Thrombolysis for acute ischaemic stroke. Cochrane Database of Systematic Reviews 2009, Issue 4. Oct. 2009.
Witztum; The oxidation hypothesis of atherosclerosis; Lancet.; 344 (8925):793-5; Sep. 17, 1994.
Zapata et al.; Engineering linear F(ab')2 fragments for efficient production in *Escherichia coli* and enhanced antiproliferative activity; Protein Eng; 8(10):1057-62; Oct. 1995.
Schaal; U.S. Appl. No. 14/279,106 entitled "Value-Assigned Solutions of Lipoprotein-Associated Phospholipase A2 having a long shelf-life," filed May 15, 2014.
Schaal et al.; U.S. Appl. No. 14/279,148 entitled "Long shelf-life kits and methods for standardizing, verifying, calibrating or recalibrating detection of lipoprotein-associated phospholipase A2," filed May 15, 2014.
Shou et al.; U.S. Appl. No. 14/498,980 entitled "Methods for detecting LP-PLA2 activity and inhibition of LP-PLA2 activity," filed Sep. 26, 2014.
Ackermann et al.; Ca(2+))-independent cytosolic phospholipase A2 from macrophage-like P388D1 cells. Isolation and characterization; J. Biol. Chem; 269(12); pp. 9227-9233; Mar. 25, 1994.
Arkin et al.; Inhibition of Protein Interaction: Non-Cellular Assay Formats; Assay Guidance Manual; 26 pages; Mar. 2012.
Atmeh et al.; Albumin Aggregates: Hydrodynamic shape and physico-chemical properties; Jordan Journal of Chemistry; 2(2); pp. 169-182; Jul. 29, 2007.
Attri et al.; Self-association of Zn-insulin at neutral pH: investigation by concentration gradient static and dynamic light scattering; Biophys. Chem.; 148(1-3); pp. 23-27; May 2010.
Bhairi; A guide to the properties and uses of detergents in biology and biochemistry; Calbiochem-Novobio-chem Corporation, San Diego; © 2001; 43 pgs.; Aug. 13, 2014; retrieved from the internet (http://wolfson.huji.ac.il/purification/PDF/detergents/calbiochem detergents.pdf).
Burke; Phospholipase A2 biochemistry; Cardiovas. Drugs Ther.; 23(1); pp. 49-59; Feb. 2009.
Cao et al; Lipoprotein-associated phospholipase A2 interacts with phospholipid vesicles via a surface-disposed hydrophobic alpha-helix; Biochemistry; 50(23); pp. 5314-5321; Jun. 14, 2011.

(56) References Cited

OTHER PUBLICATIONS

Ferrer et al.; The conformation of serum albumin in solution: a combined phosphorescence deploarization-hydrodynamic modeling; Biophys. J.; 80(5); pp. 2422-2430; May 2001.

Gardner et al.; Identification of a domain that mediates association of platelet-activating factor acetylhydrolase with high density lipoprotein; J. Biol. Chem.; 283(25); pp. 17099-17106; Jun. 20, 2008.

Heart Protection Study Group; Lipoprotein-associated phoslipase A2 activity and mass in relation to vascular disease and nonvascular mortality; J. Intern. Med.; 268; pp. 348-358; Oct. 2010.

Jaaskelainen et al.; Conformational change in the activation of lipase: an analysis in terms of low-frequency normal modes; Protein Sci.; 7(6); pp. 1359-1367; Jun. 7, 1998.

Karabina et al; Increased activity of plate-activating factor acetylhydrolase in low-density lipoprotein subfractions induces enhanced lysophosphatidylcholine production during oxidation in patients with heterozygous familial hypercholesterolaemia; Eur. J. Clin. Invest; 27(7); pp. 595-602; Jul. 1997.

Lorber et al.; Purification of octyl-beta-D-glucopyranoside and re-estimation of its micellar size; Biochimica et Biophysica Acta (BBA)- Biomembranes; 1023(2); pp. 254-265; Apr. 13, 1990.

Lund_Katz et al.; High density lipoprotein structure-function and role in reverse cholesterol transport; Subcell Biochem.; 51; pp. 183-227; Nov. 14, 2010.

Mannuzza et al.; Is bovine albumin too complex to be just a commodity? Part One: manufacturing and implications; Bioprocess International; 8(2); pp. 40-42; Feb. 2010.

Mannuzza et al.; Is bovine albumin too complex to be just a commodity? Part two: Manufacturing and implications; Bioprocess International; 8(4); pp. 42-48; Apr. 2010.

Menzies et al.; Stimulation of specific binding of [3H]-progesterone to bovine luteal cell-surface membranes: specificity of digitonin; Mol. Cell Endrocrinol.; 153 (1-2); pp. 57-69; Jul. 20, 1999.

Pande; Membrane lipid composition differentially modulates the function of human plasma platelet activating factor-acetylhydrolase; Biochim. Biophys. Acta.; 1811(1); pp. 46-56; Jan. 2011.

Qin et al.; Concentration-dependent aggregation of CHAPS investigated by NMR spectroscopy; J. Phys. Chem. B; 114(11); pp. 3863-3868; Mar. 25, 2010.

Qin et al.; Proton NMR based investigation of the effects of temperature and NaCL on micellar properties of CHAPS; J. Phys. Chem. B; 115(9); pp. 1991-1998; Mar. 10, 2011.

Samanta et al.; Crystal structure of human plasma platelet-activating factor acetylhydrolase: structural implication to lipoprotein binding and cataysis; J. Biol. Chem.; 283(43); pp. 31617-31624; Nov. 14, 2008.

Samanta et al.; Crystallization and preliminary x-ray crystallographic analysis of human plasma platelet activating factor acetyhydrolase; Protein Pept. Lett.; 16(1); pp. 97-100; Nov. 20, 2011.

SG3; Quality management systems—process validation guidance; The Global Harmonization Task Force; Edition 2; 36 pages; Jan. 2004.

Stafforini et al.; Human plasma platelet-activating factor acetylhydrolase. Association with lipoprotein particles and role in the degradation of platelet-activating factor; J. Biol. Chem.; 262(9); pp. 4215-4222; Mar. 25, 1987.

Stafforini et al.; Lipoproteins alter the catalytic behavior of the platelet-activating factor acetylhydrolase in human plasma; Proc. Natl. Acad. Sci. USA; 86(7); pp. 2393-2397; Apr. 1989.

Stafforini et al.; Molecular basis of the interaction between plasma platelet-activating factor acetylhydrolase and low density lipoprotein; J. Biol. Chem.; 274; 4(11); pp. 7018-7024; Mar. 12, 1999.

Stafforini; Biology of platelet-activating factor acetylhydrolase (PAF-AH, lipoprotein associated phospholipase A2); Cardiovasc. Drugs Ther.; 23(1); pp. 73-83; Feb. 2009.

Tjoelker et al.; Plasma platelet-activating factor acetylhydrolase is a secreted phospholipase A2 with a catalytic triad; J. Bio. Chem.; 270(43); pp. 25481-25487; Oct. 27, 1995.

Tsimihodimos et al.; Altered distribution of platelet-activating factor-acetyhyrolase activity between LDL and HDL as function of the severity of hypercholesterolemia; J. Lipid Res.; 43(2); pp. 256-263; Feb. 2002.

Tsimihodimos et al.; Fenofirate iinduces HDL-associated PAF-AH but attenuates enzyme activity associated with apoB-containing lipoproteins; J. Lipid Res. 44(5); pp. 927-934; May 2003.

Zhang et al.; Interactions between macromolecules and ions: The hofmeister series; Curr. Opin. Chem. Biol.; 10(6); pp. 658-663; Dec. 10, 2006.

Asano et al; Cellular source(s) of platelet-activating-factor acetylhydrolase activity in plasma; Biochem. Biophsys. Res. Commun.; 261(2); pp. 511-514; Aug. 2, 1999.

Ridker et al.; Relationship of lipoprotien-associated phopholipase A2 mass and activity with incident vascular events among primary prevention patients allocated to placebo or statin therapy: an analysis form the JUPITER trial; Clinical Chemistry; Clinical Chemistry; 58(5); pp. 877-886; 2012 (year of pub. sufficiently earlier than effective US filing date and any foreign priority date).

* cited by examiner

SEQUENCE LISTING

<160> NUMBER OF SEQ ID NOS: 40

<210> SEQ ID NO 1
<211> LENGTH: 353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gggatattgt gctcacccaa actcacaaat tcatgtccac atcagtagga gacagggtca    60
acatcacctg caaggccagt caggatgtga atactgctgt agcctggtat caacaaaaac   120
cagggcaatc tcctaaacta ctgattaagt gggcatccac ccggcacact ggagtccctg   180
atcgcttcac aggcagtgga tctgggacag attatatttt caccatcagc agtgtgcagg   240
ctgaagacct ggcactttat tactgtcagc aacattatag cactccgtgg acgttcggtg   300
gaggcaccaa gctggaaatc aaacgggctg atgctgcacc aactgtatcc acc          353
```

<210> SEQ ID NO 2
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Leu Thr Gln Thr His Lys Phe Met Ser Thr Ser Val Gly
1               5                   10                  15

Asp Arg Val Asn Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Lys Trp Ala Ser Thr Arg His Thr Gly Val Pro Asp Arg Phe Thr Gly
    50                  55                  60

Ser Gly Ser Gly Thr Asp Tyr Ile Phe Thr Ile Ser Ser Val Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys Arg Ala Asp Ala Ala
            100                 105                 110

Pro Thr Val Ser Thr
        115

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Ala Ser Gln Asp Val Asn Thr Ala Val Ala
1               5                   10

<210> SEQ ID NO 4
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 4

Trp Ala Ser Thr Arg His Thr
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Gln His Tyr Ser Thr Pro Trp Thr
1               5

<210> SEQ ID NO 6
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
cttccggagg tgaagctgga ggagtctgga cctgagctga agaagcctgg agagacagtc     60
aagatctcct gcaaggcttc tggttatacc ttcacagact attcagtgca ctgggtgaag    120
caggctccag gaaagggttt aaagtggatg gctggataa acactgacac tggtgagcca    180
acatttgcag atgacttcaa gggacggttt gccttctctt tggaaacctc taccagcact    240
gcctatttgc agatcaacaa cctcaaaaat gaggacacgg ctacatattt ctgtgctagg    300
ggagataact acctatatta ctatactatg gactactggg gtcaaggaat atcagtcacc    360
gtctcctcag ccaaaacgac accccatct gtctattcc                            399

<210> SEQ ID NO 7
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Leu Pro Glu Val Lys Leu Glu Glu Ser Gly Pro Glu Leu Lys Lys Pro
1               5                   10                  15

Gly Glu Thr Val Lys Ile Ser Cys Lys Ala Ser Gly Tyr Thr Phe Thr
                20                  25                  30

Asp Tyr Ser Val His Trp Val Lys Gln Ala Pro Gly Lys Gly Leu Lys
            35                  40                  45

Trp Met Gly Trp Ile Asn Thr Asp Thr Gly Glu Pro Thr Phe Ala Asp
        50                  55                  60

Asp Phe Lys Gly Arg Phe Ala Phe Ser Leu Glu Thr Ser Thr Ser Thr
65                  70                  75                  80

Ala Tyr Leu Gln Ile Asn Asn Leu Lys Asn Glu Asp Thr Ala Thr Tyr
                85                  90                  95

Phe Cys Ala Arg Gly Asp Asn Tyr Leu Tyr Tyr Tyr Thr Met Asp Tyr
            100                 105                 110
```

Trp Gly Gln Gly Ile Ser Val Thr Val Ser Ser Ala Lys Thr Thr Pro
            115                 120                 125
Pro Ser Val Tyr Ser
        130

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Tyr Thr Phe Thr Asp Tyr Ser Val His
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp Ile Asn Thr Asp Thr Gly Glu Pro Thr Phe Ala Asp Asp Phe Lys
1               5                   10                  15
Gly

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Asp Asn Tyr Leu Tyr Tyr Tyr Thr Met Asp Tyr
1               5                   10

<210> SEQ ID NO 11
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gggatattgt gatgacccaa actccagctt ctttggctgt gtctctaggg cagagggcca      60
ccatctcctg cagagccagc gaaagtgttg ataattatgg cattagtttt atgcactggt     120
tccaacagaa accaggacag ccaccccaaac tcctcatcta tgctgcatcc aaccaaggat    180
ccggggtccc tgccaggttt agtggcagtg gtctgggac agacttcagc ctcaacatcc      240
atcctatgga ggaggatgat actgcaatgt atttctgtca gcaaagtaag gaggttccat     300
tcacgttcgg ctcggggaca aagttggaaa taaaacgggc tgatgctgca ccaactgtat     360
ccacc                                                                 365

<210> SEQ ID NO 12
<211> LENGTH: 121

-continued

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Val Met Thr Gln Thr Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met His Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Phe Thr Phe Gly Ser Gly Thr Lys Leu Glu Ile Lys Arg
            100                 105                 110

Ala Asp Ala Ala Pro Thr Val Ser Thr
            115                 120

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ala Ser Glu Ser Val Asp Asn Tyr Gly Ile Ser Phe Met His
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Ser Asn Gln Gly Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Gln Ser Lys Glu Val Pro Phe Thr
1               5

<210> SEQ ID NO 16
<211> LENGTH: 405
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 16

```
cttccggagg tacagctgga gcagtcagga cctgaactgg tgaagcctgg ggcttcagtg      60
aagatatcct gcaagacttc tggatacaca ttcactgaat acaccatgca ctgggtgaaa     120
cagagccatg gaaagagccc tgagtggatt ggaggtatta atcctaacaa tggttatgct     180
aggtacaacc agaagttcaa gggcaaggcc acattgactg tagacaagtc ctccagcaca     240
gcctccatgg agctccgcag cctgacatct gaggattctg cagtctgtta ctgtgcaaga     300
gggccctatt actacggtag tagccactat gctatggact actggggtca aggaacctca     360
gtcaccgtct cctcagccaa aacgacaccc ccatctgtct attcc                     405
```

<210> SEQ ID NO 17
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Leu Pro Glu Val Gln Leu Glu Gln Ser Gly Pro Glu Leu Val Lys Pro
  1               5                  10                  15

Gly Ala Ser Val Lys Ile Ser Cys Lys Thr Ser Gly Tyr Thr Phe Thr
             20                  25                  30

Glu Tyr Thr Met His Trp Val Lys Gln Ser His Gly Lys Ser Pro Glu
         35                  40                  45

Trp Ile Gly Gly Ile Asn Pro Asn Asn Gly Tyr Ala Arg Tyr Asn Gln
     50                  55                  60

Lys Phe Lys Gly Lys Ala Thr Leu Thr Val Asp Lys Ser Ser Ser Thr
 65                  70                  75                  80

Ala Ser Met Glu Leu Arg Ser Leu Thr Ser Glu Asp Ser Ala Val Cys
                 85                  90                  95

Tyr Cys Ala Arg Gly Pro Tyr Tyr Tyr Gly Ser Ser His Tyr Ala Met
            100                 105                 110

Asp Tyr Trp Gly Gln Gly Thr Ser Val Thr Val Ser Ser Ala Lys Thr
        115                 120                 125

Thr Pro Pro Ser Val Tyr Ser
    130                 135
```

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

```
Gly Tyr Thr Phe Thr Glu Tyr Thr Met His
  1               5                  10
```

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Gly Ile Asn Pro Asn Asn Gly Tyr Ala Arg Tyr Asn Gln Lys Phe Lys
1               5                   10                  15

Gly

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Pro Tyr Tyr Tyr Gly Ser Ser His Tyr Ala Met Asp Tyr
1               5                   10

<210> SEQ ID NO 21
<211> LENGTH: 368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gggatattgt gatgacccaa actccactca ctttgtcggt taccattgga caaccagcct      60
ctatttcttg caagtcaagt cagagcctct tatatattaa tggaaaaacc tatttgaatt     120
ggttattaca gaggccaggc cagtctccaa agcgcctaat ctatctggtg tctaaactgg     180
actctggagt ccctgacagg ttcactggca gtggatcggg aacagatttt acactgaaaa     240
tcagcagagt ggaggctgag gatttgggaa tttattactg cgtgcaaggt acacattttc     300
cattcacgtt cggctcgggg acaaagttgg aaataaaacg gctgatgct gcaccaactg      360 tatccacc                                                             368

<210> SEQ ID NO 22
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ile
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Val Gln Gly
                85                  90                  95

Thr His Phe Pro Phe Thr Phe Gly Ser Gly Thr Lys Leu Glu Ile Lys
            100                 105                 110

Arg Ala Asp Ala Ala Pro Thr Val Ser Thr
          115                 120

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Ser Ser Gln Ser Leu Leu Tyr Ile Asn Gly Lys Thr Tyr Leu Asn
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Val Ser Lys Leu Asp Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Gln Gly Thr His Phe Pro Phe Thr
1               5

<210> SEQ ID NO 26
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (363)..(363)
<223> OTHER INFORMATION: a, c, t, g, unknown or other

<400> SEQUENCE: 26
cttccgcaag taaagctgga ggagtctgga cctgagctgg tgaagcctgg agcttcaatg      60
cagatatcct gcaaggcttc tggttactca ttcactgtct acaccatgaa ctgggtgaag     120
cagagccatg gaaagaacct tgagtgggtt ggacttatta atcctttcaa tggtgatact     180
acttacaacc agaagttcaa gggcaaggcc acattaactg tagacaagtc atccagcaca     240
gcctacatgg acctcctcag tctgacatct gacgactctg cagtctatta ctgtgtaaga     300 tttttgggaag gaattgactt ctggggccaa ggcaccactc tcacagtctc ctcagccaaa     360
acnacacccc catctgtcta ttcc                                            384

<210> SEQ ID NO 27
<211> LENGTH: 128
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 27

Leu Pro Gln Val Lys Leu Glu Glu Ser Gly Pro Glu Leu Val Lys Pro
1               5                   10                  15

Gly Ala Ser Met Gln Ile Ser Cys Lys Ala Ser Gly Tyr Ser Phe Thr
            20                  25                  30

Val Tyr Thr Met Asn Trp Val Lys Gln Ser His Gly Lys Asn Leu Glu
        35                  40                  45

Trp Val Gly Leu Ile Asn Pro Phe Asn Gly Asp Thr Thr Tyr Asn Gln
    50                  55                  60

Lys Phe Lys Gly Lys Ala Thr Leu Thr Val Asp Lys Ser Ser Ser Thr
65                  70                  75                  80

Ala Tyr Met Asp Leu Leu Ser Leu Thr Ser Asp Asp Ser Ala Val Tyr
                85                  90                  95

Tyr Cys Val Arg Phe Trp Glu Gly Ile Asp Phe Trp Gly Gln Gly Thr
            100                 105                 110

Thr Leu Thr Val Ser Ser Ala Lys Thr Thr Pro Pro Ser Val Tyr Ser
        115                 120                 125

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Tyr Ser Phe Thr Val Tyr Thr Met Asn
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Ile Asn Pro Phe Asn Gly Asp Thr Thr Tyr Asn Gln Lys Phe Lys
1               5                   10                  15

Gly

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Trp Glu Gly Ile Asp Phe
1               5

<210> SEQ ID NO 31
<211> LENGTH: 368
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 31

```
gggatattgt gctcacccag tctccactca ctttgtcggt taccattgga caaccagcct    60
ctatctcttg caagtcaagt cagagcctct tatatagtaa tggaaaatcc tttttgaatt   120
ggttattaca gaggccaggc cagtctccaa agcgcctaat ctatctggtg tctaaattgg   180
actctggagt ccctgacagg ttcactggct gtggatcagg aaaagatttt acactgaaaa   240
tcagcagagt ggaggctgag gatttgggag tttattactg cgtgcaaggt acacattttc   300
ctcagacgtt cggtggaggc accaagctag aaatcaaacg gctgatgct gcaccaactg    360
tatccacc                                                            368
```

<210> SEQ ID NO 32
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Asp Ile Val Leu Thr Gln Ser Pro Leu Thr Leu Ser Val Thr Ile Gly
1               5                   10                  15
Gln Pro Ala Ser Ile Ser Cys Lys Ser Ser Gln Ser Leu Leu Tyr Ser
            20                  25                  30
Asn Gly Lys Ser Phe Leu Asn Trp Leu Leu Gln Arg Pro Gly Gln Ser
        35                  40                  45
Pro Lys Arg Leu Ile Tyr Leu Val Ser Lys Leu Asp Ser Gly Val Pro
    50                  55                  60
Asp Arg Phe Thr Gly Cys Gly Ser Gly Lys Asp Phe Thr Leu Lys Ile
65                  70                  75                  80
Ser Arg Val Glu Ala Glu Asp Leu Gly Val Tyr Tyr Cys Val Gln Gly
                85                  90                  95
Thr His Phe Pro Gln Thr Phe Gly Gly Thr Lys Leu Glu Ile Lys
            100                 105                 110
Arg Ala Asp Ala Ala Pro Thr Val Ser Thr
        115                 120
```

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

```
Lys Ser Ser Gln Ser Leu Leu Tyr Ser Asn Gly Lys Ser Phe Leu Asn
1               5                   10                  15
```

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Leu Val Ser Lys Leu Asp Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Gln Gly Thr His Phe Pro Gln Thr
1               5

<210> SEQ ID NO 36
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
cttccggaag tgcagctgga gcagtcagga cctggcctag tgcagccctc acagagcctg      60
tccatcacct gcacagtctc tggtttctca ttaaccacct atgatgtact ctgggtgcgc     120
cagtctccag gaaagggtct ggagtggctg ggaattatct ggagtggtgg aagcgcagac     180
tataatgcag ctttcatctc cagactgagc atcactaagg acaattccaa gagccaagtt     240
ttctttgaaa tgaacagtct gcaagctaat gacacagcca tatattactg tgccagttac     300
tacatcaatg ctctggacta ctgggggcaa ggaacctcag tcaccgtctc ctcagccaaa     360
acgacacccc catctgtcta ttcc                                             384

<210> SEQ ID NO 37
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Leu Pro Glu Val Gln Leu Glu Gln Ser Gly Pro Gly Leu Val Gln Pro
1               5                   10                  15

Ser Gln Ser Leu Ser Ile Thr Cys Thr Val Ser Gly Phe Ser Leu Thr
            20                  25                  30

Thr Tyr Asp Val Leu Trp Val Arg Gln Ser Pro Gly Lys Gly Leu Glu
        35                  40                  45

Trp Leu Gly Ile Ile Trp Ser Gly Gly Ser Ala Asp Tyr Asn Ala Ala
    50                  55                  60

Phe Ile Ser Arg Leu Ser Ile Thr Lys Asp Asn Ser Lys Ser Gln Val
65                  70                  75                  80

Phe Phe Glu Met Asn Ser Leu Gln Ala Asn Asp Thr Ala Ile Tyr Tyr
                85                  90                  95

Cys Ala Ser Tyr Tyr Ile Asn Ala Leu Asp Tyr Trp Gly Gln Gly Thr
            100                 105                 110

Ser Val Thr Val Ser Ser Ala Lys Thr Thr Pro Pro Ser Val Tyr Ser
        115                 120                 125

```
<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Phe Ser Leu Thr Thr Tyr Asp Val Leu
1               5                   10

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Ile Trp Ser Gly Gly Ser Ala Asp Tyr Asn Ala Ala Phe Ile Ser
1               5                   10                  15

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Tyr Ile Asn Ala Leu Asp Tyr
1               5
```

LIPOPROTEIN-ASSOCIATED PHOSPHOLIPASE A2 ANTIBODY COMPOSITIONS AND METHODS OF USE

CROSS REFERENCE TO RELATED APPLICATION

This application is a continuation of U.S. patent application Ser. No. 13/839,041, filed Mar. 15, 2013 and titled "LIPOPROTEIN-ASSOCIATED PHOSPHOLIPASE A2 ANTIBODY COMPOSITIONS AND METHODS OF USE," which is herein incorporated by reference in its entirety

SEQUENCE LISTING

The instant application contains a Sequence Listing which has been submitted in ASCII format via EFS-Web and is hereby incorporated by reference in its entirety. Said ASCII copy, created on Jul. 12, 2013, is named 12248-701-300_SL.txt and is 21,605 bytes in size.

FIELD OF THE INVENTION

The present invention relates to anti-Lipoprotein-associated Phospholipase A2 (Lp-PLA2) antibody compositions and methods of detecting and treating Lp-PLA2 related diseases.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Introduction

Lipoprotein-associated Phospholipase A2 (Lp-PLA2) is an enzymatically active 50 kD protein that has been associated with Coronary vascular disease (CVD) including coronary heart disease (CHD) and stroke. Lp-PLA2 has been previously identified and characterized in the literature by Tew et al. (1996) Arterioscler. Thromb. Vasc. Biol. 16:591-599, Tjoelker, et al. (1995) Nature 374(6522):549-53), and Caslake et al. (2000) Atherosclerosis 150(2): 413-9. In addition, the protein, assays and methods of use have been described in the patent literature WO 95/00649-A1: U.S. Pat. Nos. 5,981,252, 5,968,818, 6,177,257, 7,052,862, 7,045,329, 7,217,535, 7,416,853; WO 00/24910-A1: U.S. Pat. Nos. 5,532,152; 5,605,801; 5,641,669; 5,656,431; 5,698,403; 5,977,308; and 5,847,088; WO 04/089184; WO 05/001416: U.S. Pat. No. 7,531,316; WO 05/074604; WO 05/113797; the contents of which are hereby incorporated by reference in their entirety. Lp-PLA2 is expressed by macrophages, with increased expression in atherosclerotic lesions (Hakkinin (1999) Arterioscler Thromb Vasc Biol 19(12): 2909-17). Lp-PLA2 circulates in the blood bound mainly to LDL, co-purifies with LDL, and is responsible for >95% of the phospholipase activity associated with LDL (Caslake 2000).

The United States Food and Drug Administration (FDA) has granted clearance for the PLAC® Test (diaDexus, South San Francisco, Calif.) for the quantitative determination of Lp-PLA2 in human plasma or serum, to be used in conjunction with clinical evaluation and patient risk assessment as an aid in predicting risk for coronary heart disease, and ischemic stroke associated with atherosclerosis.

Various methods for detecting Lp-PLA2 protein have been reported which include immunoassays (Caslake, 2000), activity assays (PAF Acetylhydrolase Assay Kit, Cat#760901 product brochure, Cayman Chemical, Ann Arbor, Mich., 12/18/97 (caymanchem with the extension .com of the world wide web); Azwell/Alfresa Auto PAF-AH kit available from the Nesco Company, Alfresa, 2-24-3 Sho, Ibaraki, Osaka, Japan or Karlan Chemicals, Cottonwood, Ariz., see also Kosaka (2000)), spectrophotometric assays for serum platelet activating factor acetylhydrolase activity (Clin Chem Acta 296: 151-161, WO 00/32808 (to Azwell)). Other published methods to detect Lp-PLA2 include WO 00/032808, WO 03/048172, WO 2005/001416, WO 05/074604, WO 05/113797, U.S. Pat. Nos. 5,981,252 and 5,880,273 and U.S. publication No. US 2012-0276569 A1. The contents of the published applications are hereby incorporated by reference in their entirety.

Coronary Heart Disease

Lipoprotein-associated phospholipase A2 (Lp-PLA2) levels have been shown to be significantly correlated in men with angiographically-proven Coronary Heart Disease (CHD) (Caslake 2000) and associated with cardiac events in men with hypercholesterolemia (Packard (2000) N Engl J Med 343(16): 1148-55).

Coronary heart disease (CHD) is the single most prevalent fatal disease in the United States. In the year 2003, an estimated 1.1 million Americans are predicted to have a new or recurrent coronary attack (see the American Heart Association web site, americanheart with the extension .org of the world wide web). Approximately 60% of these individuals have no previously known risk factors. It is apparent that there is a great need to diagnose individuals at risk of developing CHD, selecting patients suitable for therapy and monitoring response to therapies directed at reducing the individual's risk.

Coronary vascular disease (CVD) encompasses all diseases of the vasculature, including high blood pressure, coronary heart disease (CHD), stroke, congenital cardiovascular defects and congestive heart failure. Studies have shown that CHD is responsible for the majority of the CVD. The prevalence of CHD increases markedly as a function of age, with men having a higher prevalence than women within most age groups.

The current standard of care used to identify individuals at risk for heart disease is the measurement of a lipid panel, including triglycerides, total cholesterol, low density lipoprotein (LDL)-cholesterol, and high density lipoprotein (HDL)-cholesterol (Adult Treatment Panel III). Executive Summary of The Third Report of The National Cholesterol Education Program (NCEP) Expert Panel on Detection, Evaluation, And Treatment of High Blood Cholesterol In Adults (Adult Treatment Panel III). JAMA (2001) 285(19): 2486-97. According to the recent Adult Treatment Panel III (ATP III) guidelines (2001), depending on the risk factor score, individuals with LDL-cholesterol levels from ≥100 to ≤130 mg/dL are recommended to initiate therapeutic lifestyle changes. Adults with LDL-cholesterol >130 mg/dL are recommended for intensive lifestyle therapy and an LDL-cholesterol-lowering drug therapy to achieve an LDL-cholesterol goal of <100 mg/dL. Patients with LDL levels >160 mg/dL should be considered for therapies with lipid-lowering drugs. The American Heart Association has estimated that over 100 million adults in the US exceed the optimal level of total cholesterol. See the website americanheart with the extension .org of the world wide web.

While research continues to link elevated LDL-cholesterol levels with CHD risk, it is well understood that a significant number of individuals with normal LDL-cholesterol levels experience a cardiac event, suggesting that other factors not currently recognized may be involved (Eaton (1998) J Am Board Fam Pract 11(3): 180-6). In the search for new risk factors, significant attention has been focused in recent years on markers of inflammation, as a growing body of basic and clinical research emerges regarding the role of inflammation in atherogenesis (Lusis (2000) Atherosclerosis. Nature 407 (6801): 233-41; Lindahl (2000) N Engl J Med 343(16): 1139-47). Some of the inflammatory markers under investigation include cell adhesion molecules, CD-40 ligand, interleukin 6 and C-reactive protein (CRP, measured by the high sensitivity method, or hsCRP). CRP, a non-specific acute phase inflammatory marker, has recently received significant attention as a potential risk indicator for CHD (Ridker (2002) N Engl J Med 347(20): 1557-65; Blake (2002)); J Intern Med 252(4): 283-94). CRP, however, is well known to be responsive to many sources of inflammation, which justifies further investigations to identify more specific markers of arterial involvement.

The pathogenesis of atherosclerosis leading to the formation of unstable plaque has been recognized as one of the major causes of CHD (Lusis 2000). Recently, new understanding of the pathogenesis of atherosclerosis has placed emphasis on the inflammatory process as a key contributor to the formation of unstable plaque. The instability of the atherosclerotic plaque, rather than the degree of stenosis, is considered to be the primary culprit in the majority of myocardial infarctions (MI). This realization has led to the investigation of plaque biology and recognition that markers of inflammation may be useful as predictors of cardiovascular risk. Among the various candidate markers of inflammation, CRP (measured by high sensitivity method, hs-CRP), a non-specific acute phase inflammatory marker, has received the most attention as a predictor of CHD (Ridker 2002).

Stroke

Stroke is a leading cause of death and disability in the world. Worldwide there are 16 million first time strokes annually and 5.7 million stroke deaths. Eighty-seven percent of these deaths occur in low- and middle-income countries. Globally, there are more than 50 million survivors of stroke and transient ischemic attack (TIA). Of these survivors, at least 1 in 5 will have another stroke within 5 years (Strong K (2007) Lancet Neurol. 6:182-187).

In the United States stroke is the third-leading cause of death with about 150,000 per year. Only heart disease and cancer kill more people.

There are approximately 780,000 strokes per year, of which 600,000 are strokes occurring in patients for the first time and 180,000 are recurrent strokes. These attacks leave a large number of survivors with disabilities. Of the approximately 5-6 million stroke survivors in the United States 15%-30% of stroke victims experience permanent disability and 20% require institutional care at 3 months after onset. The total annual cost of stroke was estimated to be $62.7 billion in 2004 in the United States. See Heron (2007) National Vital Statistics Reports. 56(5):1-96 and Rosamond (2008) Circulation. 117:e25-e146. Accordingly, there is a great need to assess an individual's risk for stroke and to provide appropriate care for those who have had a stroke.

Data presented from the Rotterdam Study—Oei et al (European Society of Cardiology in August 2004) and from the ARIC Study—Ballantyne et al. (Scientific Sessions of the American Heart Association (AHA) in November 2004) indicate Lp-PLA2 is an independent risk factor for stroke. In addition, the ARIC stroke study indicated that the measurement of both hsCRP and Lp-PLA2 was particularly useful for stroke risk assessment. After adjusting for traditional cardiovascular risk factors, lipids and hsCRP, elevated levels of Lp-PLA2 were associated with a doubling of risk for ischemic stroke. As in other stroke epidemiological studies, LDL cholesterol (LDL-C) did not differentiate stroke cases from controls in ARIC. Interestingly, statins lower risk of ischemic stroke (and levels of Lp-PLA2), even though LDL-C is not a reliable predictor of stroke (Ballantyne (2005) Arch Intern Med. 165:2479-2484).

Several studies have evaluated Lp-PLA2 and stroke in acute settings. Elkind et al (Arch Intern Med. 2006; 166: 2073-2080) evaluated 467 patients with first-ever ischemic stroke who were followed for four years to determine whether levels of hs-CRP and Lp-PLA2 drawn in the setting of acute stroke (84% drawn within 72 hours of stroke) predict risk of stroke recurrence. Levels of Lp-PLA2 and hs-CRP were weakly correlated. After multivariate analysis, patients with the highest Lp-PLA2 levels had double the risk for recurrent stroke and for the combined outcome of stroke, MI, or vascular death. Lp-PLA2 identifies stroke patients who require the most aggressive treatment to prevent a second event. Cucchiara et al (Stroke. 2009 July; 40(7):2332-6) conclude that many patients with TIA have a high-risk mechanism (large vessel stenosis or cardioembolism) or will experience stroke/death within 90 days. The results from their study suggest a potential role for measuring Lp-PLA2 for short-term risk stratification of patients with acute TIA. A review article by Philip Gorelick (Am J Cardiol. 2008; 101[suppl]: 34F-40F) provides the first published review of several important prospective epidemiological studies of Lp-PLA2 and risk of stroke. He finds that the "Lp-PLA2 immunoassay may prove to be especially useful for proper risk classification of persons with stroke or cardiovascular diseases who are found to be at moderate risk. It appears useful in overall cardiovascular risk classification and may lead to more aggressive therapeutic approaches with statin agents for lipid control or with other high-risk patient approaches for cardiovascular disease reduction." Dr. Gorlick characterizes the findings of Furie et al. (Stroke 2007; 38:458) in a study evaluating Lp-PLA2 in patients with acute ischemic stroke stating "Lp-PLA2 was a significant predictor of risk of early stroke recurrence at 6 month and remained significant after multivariate adjustment for diabetes, hypertension, hyperlipidemia, atrial fibrillation, smoking and stroke subtype."

While Lp-PLA2 has previously been shown to be associated with primary and secondary stroke and useful as a marker to assess risk of stroke, no data have shown Lp-PLA2 as a useful marker to select patients who will benefit from therapy in an acute setting.

Peripheral Vascular Disease and Additional Disease

Peripheral vascular disease (PVD) is a nearly pandemic condition that has the potential to cause loss of limb, or even loss of life. PVD manifests as insufficient tissue perfusion caused by existing atherosclerosis that may be acutely compounded by either emboli or thrombi. Because of the connection between Lp-PLA2, atherosclerosis and vascular inflammation, measurement of Lp-PLA2 levels may be useful for detecting, diagnosing or monitoring PVD. Recently, Santos et al. reported studies of Lp-PLA2 and ankle-brachial index (ABI) a measure of peripheral vascular disease. They found Lp-PLA2 was a borderline-significant predictor of lower ABI (p=0.05) whereas the other markers studied, CRP and white blood count (WBC), were not significant (Santos (2004) Vasc Med. 9(3):171-6).

Lp-PLA2 has been implicated in several other diseases including respiratory distress syndrome (Grissom (2003) Crit Care Med. 31(3):770-5), immunoglobulin A nephropathy (Yoon (2002) Clin Genet. 62(2):128-34), graft patency of femoropopliteal bypass (Unno (2002) Surgery 132(1):66-71), oral-inflammation (McManus and Pinckard (2000) Crit Rev Oral Biol Med. II (2):240-58), airway inflammation and hyperreactivity (Henderson (2000) J. Immunol. 15; 164(6):3360-7), HIV and AIDS (Khovidhunkit (1999) Metabolism 48(12):1524-31), asthma (Satoh (1999) Am J Respir Crit Care Med. 159(3):974-9), juvenile rheumatoid arthritis (Tselepis (1999) Arthritis Rheum. 42(2):373-83), human middle ear effusions (Tsuji (1998) ORL J Otorhinolaryngol Relat Spec. 60(1):25-9), schizophrenia (Bell (1997) Biochem Biophys Res Commun. 29; 241(3):630-59), necrotizing enterocolitis development (Muguruma, (1997) Adv Exp Med Biol. 407:3 79-82), and ischemic bowel necrosis (Furukawa (1993) Pediatr Res. 34(2):237-41).

Molecular Basis for Disease

Oxidation of LDL in the endothelial space of the artery is considered a critical step in the development of atherosclerosis. Oxidized LDL, unlike native LDL, has been shown to be associated with a host of pro-inflammatory and pro-atherogenic activities, which can ultimately lead to atherosclerotic plaque formation (Glass (2001) Cell 104(4): 503-16; Witztum (1994) Lancet 344(8925): 793-5). Increasing evidence from basic research suggests that atherosclerosis has an inflammatory component and represents much more than simple accumulation of lipids in the vessel wall. The earliest manifestation of a lesion is the fatty streak, largely composed of lipid-laden macrophages known as foam cells. The precursors of these cells are circulating monocytes. The ensuing inflammatory response can further stimulate migration and proliferation of smooth muscle cells and monocytes to the site of injury, to form an intermediate lesion. As layers of macrophages and smooth muscle cells accumulate, a fibrous plaque is formed, which is characterized by a necrotic core composed of cellular debris, lipids, cholesterol, calcium salts and a fibrous cap of smooth muscle, collagen and proteoglycans. Gradual growth of this advanced lesion may eventually project into the arterial lumen, impeding the flow of blood. Further progression of atherosclerosis may lead to plaque rupture and subsequent thrombus formation, resulting in acute coronary syndromes such as unstable angina, MI or sudden ischemic death (Davies (2000) Heart 83:361-366; Libby (1996) Curr Opin Lipidol 7(5): 330-5).

Lp-PLA2 plays a key role in the process of atherogenesis by hydrolyzing the sn-2 fatty acid of oxidatively modified LDL, resulting in the formation of lysophosphatidylcholine and oxidized free fatty acids (Macphee (1999) Biochem J 338 (Pt 2): 479-87). Both of these oxidized phospholipid products of Lp-PLA2 action are thought to contribute to the development and progression of atherosclerosis, by their ability to attract monocytes and contribute to foam cell formation, among other pro-inflammatory actions (Macphee (2001) Curr Opin Pharmacol 1(2): 121-5; Macphee (2002) Expert Opin Ther Targets 6(3): 309-14).

Clinical Evidence

Lp-PLA2 has been previously reported as a potential risk factor for CHD. The predictive value of plasma levels of Lp-PLA2 for CHD has been reported in a large, prospective case-control clinical trial involving 6,595 men with hypercholesterolemia, known as the West of Scotland Coronary Prevention Study (WOSCOPS) (Packard 2000). Lp-PLA2 was measured in 580 CHD cases (defined by non-fatal MI, death from CHD, or a revascularization procedure) and 1,160 matched controls. The results indicated that plasma levels of Lp-PLA2 were significantly associated with development of CHD events by univariate and multivariate analyses, with almost a doubling of the relative risk for CHD events for the highest quintile of Lp-PLA2 compared to the lowest quintile. The association of Lp-PLA2 with CHD was independent of traditional risk factors such as LDL-cholesterol and other variables. This study provided an encouraging preliminary indication of the clinical utility of Lp-PLA2 as a risk factor for CHD.

Furthermore, in a study of angiographically proven CHD, Lp-PLA2 was shown to be significantly associated with the extent of coronary stenosis (Caslake 2000).

In another study, in which only females were examined (n=246, 123 cases and 123 controls), baseline levels of Lp-PLA2 were higher among cases than controls (p=0.016), but was not significantly associated with CHD when adjusted for other cardiovascular risk factors. In this study, cases included 40% of women with stroke, 51% non-fatal myocardial infarction and 9% fatal CHD (Blake (2001) J Am Coll Cardiol 38(5): 1302-6).

Recently, several large studies have added to the clinical evidence. For example, the Atherosclerosis Risk in Communities Study (ARIC) was designed to study, over a ten year period, the etiology, risk factors, clinical sequelae, and treatment alternatives for atherosclerosis. It was sponsored by the National Institutes of Health (NIH) and involved 15,792 apparently healthy men and women, aged 45 to 64, in four communities in the United States. In a retrospective study using banked samples, individuals with LDL <130 mg/dL but elevated levels of Lp-PLA2 (highest tertile) had a 2.08-fold higher risk of a coronary event compared to those individuals with low levels of Lp-PLA2 (Ballantyne (2004) Circulation. 109(7):837-42).

Monitoring Trends and Determinants in Cardiovascular Diseases Study (MONICA) was a recent World Health Organization project collecting data from 282,279 apparently healthy men from urban and rural areas in twenty-one countries. In a subsequent study using serum samples from a sub-population of the MONICA subjects, the association between Lp-PLA2 and coronary events was investigated. In this sub-study, 934 men, aged 45 to 64, were followed for 14 years. Mean baseline levels of Lp-PLA2 were significantly higher in the cases versus the non-cases (p=0.01). A one standard deviation increase in Lp-PLA2 concentration as measured by an ELISA was associated in a univariate analysis with a relative risk of 1.37 (p=0.0002), and the risk association remained statistically significant even after adjusting for other factors such as age, diabetes, smoking, blood pressure, lipid levels, BMI and CRP level (relative risk: 1.21; p<0.04). In this study, individuals with the highest levels of both Lp-PLA2 and CRP had a 1.9-fold greater risk than individuals with low levels of both markers.

Lp-PLA2 has been cleared by the FDA for predicting risk for coronary heart disease, and ischemic stroke associated with atherosclerosis. These data support the utility of Lp-PLA2 to predict a first ever stroke and is beginning to be suggested as a marker to predict a second stroke or vascular event after a first cerebrovascular event.

Alberts et al showed at the ISC in New Orleans (Stroke. 2008; 39(2):642) a meta-analysis reviewing five published prospective epidemiological studies confirming the association of elevated Lp-PLA2 and the risk of stroke (Atherosclerosis Risk in Communities (ARIC), 2005, Healthy middle-aged adults; Rotterdam Study, 2005, Healthy men and women; Veterans Affairs HDL Intervention Trial (VA-HIT), 2006, Recurrent CV events, low LDL and low HDL; Women's Health Initiative Observational Study, 2008, Postmenopausal women; Malmo Diet and Cancer Study, 2008, 5393 (60% women) healthy subjects).

In a study evaluating recurrent strokes (Elkind et al, 2006) Lp-PLA2 was related with an increased risk of recurrent stroke (adjusted hazard ratio, 2.08; 95% confidence interval, 1.04-4.18) and of the combined outcome of recurrent stroke, MI, or vascular death (adjusted hazard ratio, 1.86; 95% confidence interval, 1.01-3.42). However in the study by Furie presented at the ISC 2007, an association was found for a recurrent stroke within the next 6 months after a first stroke 1.014 (1.3-6.6), but not for the combined endpoint of stroke, MI or vascular death.

Lp-PLA2 Therapies

Several papers have been published citing the potential of Lp-PLA2 as a therapeutic target for the treatment of coronary artery disease and atherosclerosis (Caslake 2000; Macphee 2001; Carpenter (2001) FEBS Lett. 505(3):357-63; Leach (2001) Farmaco 56 (1-2): 45-50). Evidence that Lp-PLA2 is a therapeutic target for the treatment of CHD has been published in many articles describing several genuses of inhibitors of Lp-PLA2 and their use. These genuses include but are not limited to: azetidinone inhibitors, SB-222657, SB-223777 (MacPhee 1999); reversible 2-(alkylthio)-pyrimidin-4-ones (Boyd et al. (2000) Bioorg Med Chem Lett. 10(4):395-8); natural product derived inhibitors, SB-253514 and analogues (Pinto (2000); Bioorg Med Chem Lett. 10(17): 2015-7); inhibitors produced by *Pseudomonas fluorescens* DSM 11579, SB-253514 and analogues (Thirkettle (2000) et al. J Antibiot (Tokyo). 53(7):664-9; Busby (2000) J Antibiot (Tokyo). 53(7):670-6; Thirkettle (2000) J Antibiot (Tokyo). 53(7):733-5); 2-(alkylthio)-pyrimidones, orally active 1-((amidolinked)-alkyl)-pyrimidones (Boyd et al. (2000) Bioorg Med Chem Lett. 10(22):2557-61); modified pyrimidone 5-substituent in 1-((amidolinked)-alkyl)-pyrimidones is highly water soluble (Boyd, et al. (2001) Bioorg Med Chem Lett. 2001 11(5):701-4); phenylpiperazineacetamide derivative of lipophilic 1-substituent in 1-((amidolinked)-alkyl)-pyrimidones (Bloomer (2001) Bioorg Med Chem Lett. 11(14):1925-9); 5-(Pyrazolylmethyl) derivative and 5-(methoxypyrimidinylmethyl) derivative of 1-(biphenylmethylamidoalkyl)-pyrimidones (Boyd et al. (2002) Bioorg Med Chem Lett. 12(1):51-5); cyclopentyl fused derivative, SB-480848, of the pyrimidone 5-substituent in clinical candidate SB-435495 (Blackie (2003) Bioorg Med Chem Lett. 2003 Mar. 24; 13(6):1067-70). To date, GlaxoSmithKline (GSK) has announced positive clinical data for a novel compound, darapladib, that dramatically lowers Lp-PLA2 activity. Darapladib and other Lp-PLA2 inhibitors, including ralapladib, may represent a new generation of drugs that reduce cardiovascular disease and death.

Winkler recently reported a multicenter, double-blind, randomized study evaluating the effects of fluvastatin XL versus placebo on the level of Lp-PLA2 in 89 patients with type 2 diabetes (42 fluvastatin and 47 placebo) (Winkler (2004) J Clin Endocrinol Metab. 89 (3) 1153-1159). Among these subjects, higher Lp-PLA2 activity was significantly associated with a history of CAD. The highest quartile in terms of Lp-PLA2 activity was at significantly greater risk than the lowest quartile (risk ratio: 2.09; 95% CI: 1.02-4.29; p=0.043). Fluvastatin treatment decreased Lp-PLA2 activity by 22.8%. Blankenberg also reported that taking statins lowered the measurable Lp-PLA2 activity (Blankenberg (2003) J of Lipid Research 44: 1381-1386).

Albert et al reported on the effect of statin therapy on lipoprotein associated phospholipase a2 levels. The researchers evaluated the effect of pravastatin 40 mg daily vs. placebo on Lp-PLA2 levels in a cardiovascular disease free population derived from the PRINCE trial. After 12 weeks, Lp-PLA2 levels decreased by 22.1% among treated patients (vs. 7.8% among placebo group). Only 6% of the lowering of Lp-PLA2 by pravastatin could be accounted for by the lowering of LDL-C (Albert (2005) Atherosclerosis. 182:193-198).

Schaefer et al reported on the effects of atorvastatin versus other statins on fasting and postprandial c-reactive protein and Lp-PLA2 in patients with coronary heart disease versus control subjects. In this study the impact of various statins at the 40 mg/day dosage on Lp-PLA2 was compared. The study found that "atorvastatin is more effective than fluvastatin, lovastatin, pravastatin, or simvastatin for decreasing not only low density lipoprotein cholesterol but also hs-CRP and Lp-PLA2" (Schaefer (2005) Am J Cardiol. 95:1025-1032).

Saougos et al have reported on the effect of hypolipidemic drugs on Lp-PLA2. This is the first study to demonstrate that ezetimibe and rosuvastatin both lower Lp-PLA2 mass. Statin intolerant Type IIa dyslipidemics had an 18% reduction in Lp-PLA2 mass with ezetimibe 10 mg/day, and Type IIa dyslipidemics had a 29% reduction in Lp-PLA2 mass with rosuvastatin 10 mg/day. It also showed that fenofibrate 200 mg/day lowered Lp-PLA2 mass 32%, a finding similar to fenofibrate's effect on Lp-PLA2 mass in Type 2 DM (Saogos (2007) Arterioscler Thromb Vasc Biol. 27:2236-2243).

Muhlestein et al reported on The Reduction of Lp-PLA2 by statin, fibrate, and combination therapy among diabetic patients with mixed dyslipidemia. This study evaluated the effect of simvastatin 20 mg and fenofibrate 160 mg on Lp-PLA2 and CRP in type 2 diabetic patients with mixed dyslipidemia. Fenofibrate, simvastatin and the combination each lowered Lp-PLA2, and the effect was greatest among patients with baseline levels greater than the median. In this study, lipid-modifying agents lowered Lp-PLA2 by more than 25% (fenofibrate: 27%; simvastatin: 35%) (Muhlestein (2006) J Am Coll Cardiol. 48:396-401).

Rosenson et al recently reported on the effects of fenofibrate on Lp-PLA2 levels in non-diabetic patients with metabolic syndrome. In this study reduction in small LDL-P particles was significantly associated with the reduction in Lp-PLA2, suggesting that fenofibrate may lower Lp-PLA2 via plaque stabilization mediated by lowering small LDL-P (Rosenson (2008) Am Heart J. 155(3):499.e9-16).

Schmidt et al reported on the effects of eicosapentaenoic acid (EPA) on Lp-PLA2 levels in patients admitted to elective coronary angiography because of suspected coronary artery disease (CAD). The content of the marine n-3 fatty acid, eicosapentaenoic acid (EPA) in adipose tissue, a measure of long-term intake of seafood independently and inversely correlated with plasma levels of Lp-PLA2(r=−0.18, p<0.01). The results support that Lp-PLA2 may relate to CAD and that intake of marine n-3 fatty acids might reduce plasma Lp-PLA2 suggesting another mechanism by which n-3 fatty acids could reduce the risk of cardiovascular disease.

Kuvin et al reported on effects of extended-release niacin on lipoprotein particle size, distribution, and inflammatory markers in patients with coronary artery disease. This study evaluated the effect on Lp-PLA2 of adding niacin to stable coronary heart disease patients with well-managed baseline LDL levels of 76 mg/dL. While there was no significant change in baseline LDL levels after three months, niacin significantly lowered Lp-PLA2 by 20% (Kuvin (2006) Am J Cardiol. 98:743-745).

It appears from this study that Lp-PLA2 lowering was independent of LDL (which did not change) and that there appears to be residual opportunity to lower Lp-PLA2 in patients with low achieved LDL cholesterol, consistent with the concept that low achieved LDL alone may not assure that plaque has stabilized.

These studies identify therapies which benefit patients who have an increased risk of Lp-PLA2 related disease, e.g. CVD including coronary heart disease and stroke.

Care in the Acute Setting

The American Heart Association and American Stroke Association strongly urge people to seek medical attention as soon as possible if they believe they're having a stroke or heart attack. The sooner thrombolytic agents or other appropriate treatment is begun, the better the chances for recovery. One such thrombolytic agent is tissue plasminogen activator (tPA), a clot-busting drug. tPA is approved for use in certain patients having a heart attack or stroke. The drug can dissolve blood clots, which cause most heart attacks and strokes. tPA is the only drug approved by the U.S. Food and Drug Administration for the acute (urgent) treatment of ischemic stroke.

According to the American Heart Association studies have shown that thrombolytic agents, such as tPA, can reduce the amount of damage to the heart muscle and save lives. However, to be effective, they must be given within a few hours after symptoms begin. Administering tPA or other clot-dissolving agents is complex and is done through an intravenous (IV) line in the arm by hospital personnel. tPA has also been shown to be effective in treating ischemic stroke. This kind of stroke is caused by blood clots that block blood flow to the brain.

In 1996 the U.S. Food and Drug Administration (FDA) approved the use of tPA to treat ischemic stroke in the first three hours after the start of symptoms. This makes it very important for people who think they're having a stroke to seek help immediately. If given promptly, tPA can significantly reduce the effects of stroke and reduce permanent disability. tPA can only be given to a person within the first few hours after the start of stroke symptoms. The National Institute of Neurological Disorders and Stroke (NINDS) study suggested that 8 out of 18 stroke patients who receive tPA according to a strict protocol will recover by three months after the event without significant disability. This is compared to 6 out of 18 stroke patients (one-third) who recover substantially regardless of treatment. (N Engl J Med 333:1581-1587, 1995.)

While tPA or other thrombolytics can reduce disability from a heart attack or stroke, there is also a higher risk of bleeding. Studies vary in predicting the likelihood of complications, which include bleeding into the brain, other types of serious bleeding (e.g., gastrointestinal), and death. The NINDS study suggested that bleeding into the brain occurred in about 1 out of 18 patients receiving tPA (specifically, 5.8%). When this occurred, there was a 45 percent fatality rate. Several studies suggested treatment with "clot-dissolving" medications increases the number of patients who die following a stroke (JAMA 274(13):1017, 1995; Lancet 346:1509-1514, 1995; JAMA 276(12):961-6, 1996; NEJM 335 (3):145, 1996; Lancet 352:1245-1251, 1998; JAMA 282(21):2019-26. 1999). Subsequent studies demonstrated that using tPA more liberally than is recommended in the NINDS protocol resulted in a higher rate of intracranial hemorrhage (JAMA 283:1151-1158, 2000; Cerebrovasc Dis 8 (suppl 4):48, 1998; Arch Intern Med 162:1994-2001, 2002; Cochrane Database Syst Rev. 2000:CD000213; Cochrane Database Syst Rev. 2000:CD000029). Complications are more likely when tPA is used in patients over 70 years old, those with more severe stroke, or those with glucose over 300 mg/dl.

Due to the severe risks associated with thrombolytics, it is important for physicians to weigh the possibility of benefit (e.g. improved function at 3 months) against the possibility of harm (severe bleeding or death). Stroke symptoms alone are insufficient to definitely diagnose stroke and, in patients with a stroke mimic, tPA use results only in potential adverse effects without any possibility of benefit. It is clear there is a need to identify patients who are suspected of having a cardiovascular event who will benefit from administration of thrombolytics (e.g. tPA).

Lp-PLA2 can be used to identify patients who will benefit from administration of thrombolytics. Lp-PLA2 expression has been shown to be higher in carotid plaques of patients with than without cardiac events (Herrmann (2009) Eur Heart J. 30(23):2930-8). In the event of a plaque rupture and vascular thrombus, high levels of Lp-PLA2 may be released into circulation from the rupture site. Measuring Lp-PLA2 levels of individuals suspected of having a stroke or myocardial infarction (e.g. individuals who present symptoms of a stroke or MI) can identify individuals who will benefit from standard thrombolytic therapy or and those who may need aggressive therapy including aggressive thrombolytic drug dosing, drug combinations and/or interventional and surgical therapies.

All publications and other materials described herein are used to illuminate the invention or provide additional details respecting the practice and are hereby incorporated by reference in their entirety.

SUMMARY OF THE INVENTION

This invention is directed to an isolated antibody, or antigen binding fragment thereof, wherein the antibody competes for binding to Lp-PLA2 with a reference antibody comprising: a light chain variable region comprising an amino acid sequence selected from the group consisting of SEQ ID NOs: 2, 12, 22, and 32; and a heavy chain variable region comprising an amino acid sequence selected from the group consisting of SEQ ID NOs: 7, 17, 27, and 37. Further, the antibody is a monoclonal antibody, a human antibody, a humanized or a chimeric antibody.

The invention is further directed to an isolated monoclonal antibody, or antigen binding fragment thereof, comprising: a light chain variable region comprising CDR1, CDR2 and CDR3 sequences; and a heavy chain variable region comprising CDR1, CDR2, CDR3 sequences, wherein the light chain variable region CDR1 sequence comprises an amino acid sequence selected from the group consisting of SEQ ID NO: 3, 13, 23, and 33, and conservative modifications thereof; the heavy chain variable region CDR1 sequence comprises an amino acid sequence selected from the group consisting of SEQ ID NO: 8, 18, 28, and 38, and conservative modifications thereof; light chain variable region CDR2 sequence comprises an amino acid sequence selected from the group consisting of SEQ ID NO: 4, 14, 24, and 34, and conservative modifications thereof; and the heavy chain variable region CDR2 sequence comprises an amino acid sequence selected from the group consisting of SEQ ID NO: 9, 19, 29, and 39, and conservative modifications thereof; the light chain variable region CDR3 sequence comprises an amino acid sequence selected from the group consisting of SEQ ID NO: 5, 15, 25, and 35, and conservative modifications thereof; and the heavy chain variable region CDR3 sequence comprises an amino acid sequence selected from the group consisting of SEQ ID NO: 10, 20, 30, and 40, and conservative modifications thereof, and the antibody binds to Lp-PLA2.

The antibody may be produced in bacteria or in mammalian cells (or by other organisms not limited to plants, yeast). The invention is also directed to a method of producing the antibodies comprising culturing an appropriate cell and recovering the antibody from the cell culture.

The invention is also directed to a transgenic mouse comprising human immunoglobulin light and heavy chain transgenes, wherein the mouse expresses the antibody of the instant invention. Additionally, a hybridoma may be prepared from such mouse, wherein the hybridoma produces said antibody.

The invention is also directed to compositions comprising the antibodies and a carrier.

In addition, the invention is directed to an article of manufacture comprising a container and a composition contained therein, wherein the composition comprises an antibody as described herein. The article of manufacture may also comprise an additional component, e.g., a package insert indicating that the composition can be used detect or diagnose an Lp-PLA2 related disease.

In the invention is further directed to a method for detecting Lp-PLA2 in a subject comprising contacting a sample from the subject with an antibody, or antigen binding fragment thereof, of the instant invention under conditions suitable for binding; determining the level of Lp-PLA2 in the sample.

DETAILED DESCRIPTION OF THE INVENTION

Definitions and General Techniques

As used herein, the teens "embodiment" and "aspect" are used interchangeably. "Lipoprotein-associated Phospholipase A2", "Lp-PLA2", "LpPLA2", "Lp-PLA2", "Platelet-activating factor-acetylhydrolase", "PAF-AH", and "LDL-PLA2" are used interchangeably herein and within the literature and refer to native Lp-PLA2, and allelic variants thereof, as described, for example, in Tew et al. (1996) Arterioscler. Thromb. Vasc. Biol. 16:591-599, Tjoelker, et al. (1995) Nature 374(6522):549-53), Caslake et al. (2000) Atherosclerosis 150(2): 413-9, Genbank RefSeq IDs: NM_005084, NP_005075, NM_001168357 and NP_001161829 and Genebank Entrez GeneID: 7941 (PLA2G7), which are hereby incorporated by reference in their entirety. Unless indicated otherwise, the terms "Lipoprotein-associated Phospholipase A2", "Lp-PLA2", "LpPLA2", "Lp-PLA2", "Platelet-activating factor-acetylhydrolase", "PAF-AH", and "LDL-PLA2" when used herein refer to the human protein.

The term "Lp-PLA2 activity" as used here includes the biochemical activities of Lp-PLA2, including catalytic activity of Lp-PLA2, hydrolysis of the sn-2 fatty acid of oxidatively modified LDL, the formation of lysophosphatidylcholine and oxidized free fatty acids, hydrolysis of PAF; and biological activities of Lp-PLA2 function including attraction monocytes to vascular plaques, foam cell formation, upregulation of other pro-inflammatory agents, growth of vascular plaques, destabilization of vascular plaques, development of atherosclerosis or other Lp-PLA2 related diseases, progression of atherosclerosis or other Lp-PLA2 related diseases.

The terms "Lp-PLA2 associated disease" or "Lp-PLA2 related disease" means the diseases described herein and any disease in which abnormal Lp-PLA2 expression or activity is present. Without the limiting the foregoing, Lp-PLA2 associated diseases include vascular disease, coronary vascular disease, atherosclerosis, PVD, and rheumatoid arthritis.

As used herein, the term "coronary vascular disease" or "CVD" means diseases of the vasculature, including high blood pressure, coronary heart disease (CHD), myocardial infarction, stroke, transient ischemic attack (TIA), cerebrovascular accident (CVA), congenital cardiovascular defects and congestive heart failure. Coronary vascular disease includes primary and subsequent acute events including myocardial infarction, stroke, TIA and CVA.

The term "antibody" (Ab) as used herein includes monoclonal antibodies, polyclonal antibodies, multispecific antibodies (e.g. bispecific antibodies), and antibody fragments, so long as they exhibit the desired biological activity. The team "immunoglobulin" (Ig) is used interchangeably with "antibody" herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. Preferably, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for [L and F isotypes. Each 6 L chain has at the N-terminus, a variable domain (VL) followed by a constant domain (CL) at its other end.

The VL is aligned with the VH and the CL is aligned with the first constant domain of the heavy chain (CHI).

Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Teff and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ and μ, respectively. The γ and α classes are further divided into subclasses on the basis of relatively minor differences in CH sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 1-10-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a P-sheet configuration, connected by three hypervariable regions, which form loops connecting, and in some cases forming part of, the P-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (LI), 5056 (L2) and 89-97 (L3) in the VL, and around about 1-35 (HI), 50-65 (H2) and 95-102 (H3) in the VH; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (LI), 50-52 (L2) and 91-96 (U) in the VL, and 26-32 (HI), 53-55 (1-12) and 96-101 (H3) in the VH; Chothia and Lesk J. Mol. Biol. 196: 901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences. An "intact" antibody is one which comprises an antigen-binding site as well as a CL and at least heavy chain constant domains, CHI, CH2 and CH3. The constant domains may be native sequence constant domains (e.g. human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CHI). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CHI domain including one or more cysteines from the antibody hinge region. Fab'-SH is the designation herein for Fab' in which the cysteine residue(s) of the constant domains bear a free thiol group. F(ab')2 antibody fragments originally were produced as pairs of 8 Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993), the disclosures of which are hereby expressly incorporated by reference.

A "native sequence" polypeptide is one which has the same amino acid sequence as a polypeptide (e.g., antibody) derived from nature. Such native sequence polypeptides can be isolated from nature or can be produced by recombinant or synthetic means. Thus, a native sequence polypeptide can have the amino acid sequence of a naturally occurring human polypeptide, murine polypeptide, or polypeptide from any other mammalian species.

The term "amino acid sequence variant" refers to a polypeptide that has amino acid sequences that differ to some extent from a native sequence polypeptide. Ordinarily, amino acid sequence variants of Lp-PLA2 will possess at least about 70% homology with the native sequence Lp-PLA2, preferably, at least about 80%, more preferably at least about 85%, even more preferably at least about 90% homology, and most preferably at least 95%. The amino acid sequence variants can possess substitutions, deletions, and/or insertions at certain positions within the amino acid sequence of the native amino acid sequence. Examples of Lp-PLA2 variants include those described in Grallert et al., Eur Heart J. 2012 January; 33(2): 238-5, Song et al., Pharmacogenomics J. 2012 October; 12(5):425-31, Casas et al., Circulation. 2010 Jun. 1; 121(21): 2284-93, Hoffmann et al, J Thromb Haemost. 2009 January; 7(1):41-8, Kruse et al., Am J Hum Genet. 2000 May; 66(5): 1522-30, Tew et al. (1996) Arterioscler. Thromb. Vase. Biol. 16:591-599, Tjoelker, et al. (1995) Nature 374(6522):549-53), Caslake et al. (2000) Atherosclerosis 150(2): 413-9, Genbank RefSeq IDs: NM_005084, NP_005075, NM_001168357 and NP_001161829 and Genebank Entrez GeneID: 7941 (PLA2G7), the disclosures of which are hereby expressly incorporated by reference. Antibodies of the instant invention bind to these variants of Lp-PLA2.

The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcεRI.

"Homology" is defined as the percentage of residues in the amino acid sequence variant that are identical after aligning the sequences and introducing gaps, if necessary, to achieve the maximum percent homology. Methods and computer programs for the alignment are well known in the art. Sequence similarity may be measured by any common sequence analysis algorithm, such as GAP or BESTFIT or other variation Smith-Waterman alignment. See, T. F. Smith and M. S. Waterman, J. Mol. Biol. 147:195-197 (1981) and W. R. Pearson, Genomics 11:635-650 (1991).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

An antibody having a "biological characteristic" of a designated antibody, such as any of the monoclonal antibodies LpPLA2.A7.1, LpPLA2.A8.2, LpPLA2.A201.1, LpPLA2.A202.1, LpPLA2.A203.1, LpPLA2.B5.2, LpPLA2.B6, LpPLA2.B17.1, LpPLA2.B17.2, LpPLA2.B26, LpPLA2.B31, LpPLA2.B38.2, LpPLA2.B40, LpPLA2.B44, LpPLA2.B48, LpPLA2.B69, LpPLA2.B71, LpPLA2.B78, LpPLA2.B81, LpPLA2.B82, LpPLA2.B84, LpPLA2.B94, LpPLA2.B98, LpPLA2.B130, LpPLA2.B132, LpPLA2.B142, LpPLA2.B144.1, LpPLA2.B144.2, LpPLA2.B149, LpPLA2.B154, LpPLA2.B155, LpPLA2.B159.3, LpPLA2.B160, LpPLA2.B179, LpPLA2.B194, LpPLA2.B195, LpPLA2.B200.1, LpPLA2.B200.2, LpPLA2.B201.1, LpPLA2.B206, LpPLA2.B213, LpPLA2.B224, LpPLA2.B225, LpPLA2.B228, LpPLA2.B229.1, LpPLA2.B235, LpPLA2.B236, LpPLA2.B238, LpPLA2.B241, LpPLA2.B248, LpPLA2.B251, LpPLA2.B266, LpPLA2.B280, LpPLA2.B281, LpPLA2.B500.6, LpPLA2.B501.5, LpPLA2.C1, LpPLA2.C2, LpPLA2.C3, LpPLA2.C4, LpPLA2.C5, LpPLA2.C6, LpPLA2.C7, LpPLA2.C8, LpPLA2.C9, LpPLA2.C10, LpPLA2.C11, LpPLA2.C12, LpPLA2.C13, LpPLA2.C14, LpPLA2.C15, LpPLA2.C16, LpPLA2.C18, LpPLA2.C19, LpPLA2.C201.1, and LpPLA2.C203.1 is one which possesses one or more of the biological characteristics of that antibody which distinguish it from other antibodies that bind to the same antigen, LpPLA2.A7.1, LpPLA2.A8.2, LpPLA2.A201.1, LpPLA2.A202.1, LpPLA2.A203.1, LpPLA2.B5.2, LpPLA2.B6, LpPLA2.B17.1, LpPLA2.B17.2, LpPLA2.B26, LpPLA2.B31, LpPLA2.B38.2, LpPLA2.B40, LpPLA2.B44, LpPLA2.B48, LpPLA2.B69, LpPLA2.B71, LpPLA2.B78, LpPLA2.B81, LpPLA2.B82, LpPLA2.B84, LpPLA2.B94, LpPLA2.B98, LpPLA2.B130, LpPLA2.B132, LpPLA2.B142, LpPLA2.B144.1, LpPLA2.B144.2, LpPLA2.B149, LpPLA2.B154, LpPLA2.B155, LpPLA2.B159.3, LpPLA2.B160, LpPLA2.B179, LpPLA2.B194, LpPLA2.B195, LpPLA2.B200.1, LpPLA2.B200.2, LpPLA2.B201.1, LpPLA2.B206, LpPLA2.B213, LpPLA2.B224, LpPLA2.B225, LpPLA2.B228, LpPLA2.B229.1, LpPLA2.B235, LpPLA2.B236, LpPLA2.B238, LpPLA2.B241, LpPLA2.B248, LpPLA2.B251, LpPLA2.B266, LpPLA2.B280, LpPLA2.B281, LpPLA2.B500.6, LpPLA2.B501.5, LpPLA2.C1, LpPLA2.C2, LpPLA2.C3, LpPLA2.C4, LpPLA2.C5, LpPLA2.C6, LpPLA2.C7, LpPLA2.C8, LpPLA2.C9, LpPLA2.C10, LpPLA2.C11, LpPLA2.C12, LpPLA2.C13, LpPLA2.C14, LpPLA2.C15, LpPLA2.C16, LpPLA2.C18, LpPLA2.C19, LpPLA2.C201.1, and LpPLA2.C203.1 will bind the same epitope as that bound by LpPLA2.A7.1, LpPLA2.A8.2, LpPLA2.A201.1, LpPLA2.A202.1, LpPLA2.A203.1, LpPLA2.B5.2, LpPLA2.B6, LpPLA2.B17.1, LpPLA2.B17.2, LpPLA2.B26, LpPLA2.B31, LpPLA2.B38.2, LpPLA2.B40, LpPLA2.B44, LpPLA2.B48, LpPLA2.B69, LpPLA2.B71, LpPLA2.B78, LpPLA2.B81, LpPLA2.B82, LpPLA2.B84, LpPLA2.B94, LpPLA2.B98, LpPLA2.B130, LpPLA2.B132, LpPLA2.B142, LpPLA2.B144.1, LpPLA2.B144.2, LpPLA2.B149, LpPLA2.B154, LpPLA2.B155, LpPLA2.B159.3, LpPLA2.B160, LpPLA2.B179, LpPLA2.B194, LpPLA2.B195, LpPLA2.B200.1, LpPLA2.B200.2, LpPLA2.B201.1, LpPLA2.B206, LpPLA2.B213, LpPLA2.B224, LpPLA2.B225, LpPLA2.B228, LpPLA2.B229.1, LpPLA2.B235, LpPLA2.B236, LpPLA2.B238, LpPLA2.B241, LpPLA2.B248, LpPLA2.B251, LpPLA2.B266, LpPLA2.B280, LpPLA2.B281, LpPLA2.B500.6, LpPLA2.B501.5, LpPLA2.C1, LpPLA2.C2, LpPLA2.C3, LpPLA2.C4, LpPLA2.C5, LpPLA2.C6, LpPLA2.C7, LpPLA2.C8, LpPLA2.C9, LpPLA2.C10, LpPLA2.C11, LpPLA2.C12, LpPLA2.C13, LpPLA2.C14, LpPLA2.C15, LpPLA2.C16, LpPLA2.C18, LpPLA2.C19, LpPLA2.C201.1, and LpPLA2.C203.1 (e.g. which competes for binding or blocks binding of monoclonal antibody LpPLA2.A7.1, LpPLA2.A8.2, LpPLA2.A201.1, LpPLA2.A202.1, LpPLA2.A203.1, LpPLA2.B5.2, LpPLA2.B6, LpPLA2.B17.1, LpPLA2.B17.2, LpPLA2.B26, LpPLA2.B31, LpPLA2.B38.2, LpPLA2.B40, LpPLA2.B44, LpPLA2.B48, LpPLA2.B69, LpPLA2.B71, LpPLA2.B78, LpPLA2.B81, LpPLA2.B82, LpPLA2.B84, LpPLA2.B94, LpPLA2.B98, LpPLA2.B130, LpPLA2.B132, LpPLA2.B142, LpPLA2.B144.1, LpPLA2.B144.2, LpPLA2.B149, LpPLA2.B154, LpPLA2.B155, LpPLA2.B159.3, LpPLA2.B160, LpPLA2.B179, LpPLA2.B194, LpPLA2.B195, LpPLA2.B200.1, LpPLA2.B200.2, LpPLA2.B201.1, LpPLA2.B206, LpPLA2.B213, LpPLA2.B224, LpPLA2.B225, LpPLA2.B228, LpPLA2.B229.1, LpPLA2.B235, LpPLA2.B236, LpPLA2.B238, LpPLA2.B241, LpPLA2.B248, LpPLA2.B251, LpPLA2.B266, LpPLA2.B280, LpPLA2.B281, LpPLA2.B500.6, LpPLA2.B501.5, LpPLA2.C1, LpPLA2.C2, LpPLA2.C3, LpPLA2.C4, LpPLA2.C5, LpPLA2.C6, LpPLA2.C7, LpPLA2.C8, LpPLA2.C9, LpPLA2.C10, LpPLA2.C11, LpPLA2.C12, LpPLA2.C13, LpPLA2.C14, LpPLA2.C15, LpPLA2.C16, LpPLA2.C18, LpPLA2.C19, LpPLA2.C201.1, and LpPLA2.C203.1 to Lp-PLA2. Likewise, an antibody with the biological characteristic of the LpPLA2.A7.1, LpPLA2.A8.2, LpPLA2.A201.1, LpPLA2.A202.1, LpPLA2.A203.1, LpPLA2.B5.2, LpPLA2.B6, LpPLA2.B17.1, LpPLA2.B17.2, LpPLA2.B26, LpPLA2.B31, LpPLA2.B38.2, LpPLA2.B40, LpPLA2.B44, LpPLA2.B48, LpPLA2.B69, LpPLA2.B71, LpPLA2.B78, LpPLA2.B81, LpPLA2.B82, LpPLA2.B84, LpPLA2.B94, LpPLA2.B98, LpPLA2.B130, LpPLA2.B132, LpPLA2.B142, LpPLA2.B144.1, LpPLA2.B144.2, LpPLA2.B149, LpPLA2.B154, LpPLA2.B155, LpPLA2.B159.3, LpPLA2.B160, LpPLA2.B179, LpPLA2.B194, LpPLA2.B195, LpPLA2.B200.1, LpPLA2.B200.2, LpPLA2.B201.1, LpPLA2.B206, LpPLA2.B213, LpPLA2.B224, LpPLA2.B225, LpPLA2.B228, LpPLA2.B229.1, LpPLA2.B235, LpPLA2.B236, LpPLA2.B238, LpPLA2.B241, LpPLA2.B248, LpPLA2.B251, LpPLA2.B266, LpPLA2.B280, LpPLA2.B281, LpPLA2.B500.6, LpPLA2.B501.5, LpPLA2.C1, LpPLA2.C2, LpPLA2.C3, LpPLA2.C4, LpPLA2.C5, LpPLA2.C6, LpPLA2.C7, LpPLA2.C8, LpPLA2.C9, LpPLA2.C10, LpPLA2.C11, LpPLA2.C12, LpPLA2.C13, LpPLA2.C14, LpPLA2.C15, LpPLA2.C16, LpPLA2.C18, LpPLA2.C19, LpPLA2.C201.1, and LpPLA2.C203.1 antibody will have the same epitope binding, targeting, protein detection, therapeutic effect and properties of the antibody.

The term "antagonist" antibody is used in the broadest sense, and includes an antibody that partially or fully blocks, inhibits, or neutralizes a biological activity of a native Lp-PLA2 protein disclosed herein. Methods for identifying antagonists of an Lp-PLA2 polypeptide may comprise contacting an Lp-PLA2 polypeptide or a cell expressing Lp-PLA2 on the cell surface, with a candidate antagonist antibody and measuring a detectable change in one or more biological activities normally associated with the Lp-PLA2 polypeptide. An agonist antibody includes antibodies that enhance, activate or facilitate the function of Lp-PLA2.

An "antibody that inhibits Lp-PLA2 activity" or an "inhibitory" antibody is one which binds to and results in measurable inhibition of Lp-PLA2, in vitro or in vivo. Preferred inhibitory anti-Lp-PLA2 antibodies inhibit activity of Lp-PLA2 by greater than 20%, preferably from about 20% to about 50%, and even more preferably, by greater than 50% (e.g. from about 50% to about 100%) as compared to the appropriate control, the control typically being Lp-PLA2 not treated with the antibody being tested. Inhibition can be measured at an antibody concentration of about 0.1 to 30 pg/ml or about 0.5 nM to 200 nM in body fluid, where the growth inhibition is determined 1-10 days after exposure to the antibody. Inhibition of Lp-PLA2 in vivo can be determined in various ways such as is described in the Experimental Examples section below. The antibody is inhibitory in vivo if administration of the anti-Lp-PLA2 antibody at about 1 pg/kg to about 100 mg/kg body weight results in reduction in Lp-PLA2 activity within about 5 days to 3 months from the first administration of the antibody, preferably within about 5 to 30 days.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses Lp-PLA2. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cells in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereofctivating receptor FcγRIIA contains an immunoreceptor tyrosine-based activation motif (ITAM) in its cytoplasmic domain. Inhibiting receptor FcγRI1B contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126.330-41 (1995). Other FcRs, including those to be identified in the future, are encompassed by the term "FcR" herein. The term also includes the neonatal receptor, FcRn, which is responsible for the transfer, of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g. from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., J. Immunol. Methods 202:163 (1996) may be performed.

"Label" as used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

The teem "epitope tagged" used herein refers to a chimeric polypeptide comprising an anti-Lp-PLA2 polypeptide fused to a "tag polypeptide". The anti-Lp-PLA2 polypeptide may be an anti-Lp-PLA2 antibody, or antigenic fragment thereof. The tag polypeptide has enough residues to provide an epitope against which an antibody can be made, yet is short enough such that it does not interfere with activity of the attached protein to which it is fused. The tag polypeptide is also preferably fairly unique so that the antibody against it does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The term "package insert" is used to refer to instructions customarily included in commercial packages of therapeutic products, that contain information about the indications, usage, dosage, administration, contraindications and/or warnings concerning the use of such therapeutic products. A package insert is also used to refer to instructions customarily included in commercial packages of diagnostic products, that contain information about the indications, usage, dosage, administration, contraindications and/or warnings concerning the use of such diagnostic products.

An "isolated nucleic acid molecule" is a nucleic acid molecule, e.g., an RNA, DNA, or a mixed polymer, which is substantially separated from other genome DNA sequences as well as proteins or complexes such as ribosomes and polymerases, which naturally accompany a native sequence. The term embraces a nucleic acid molecule which has been removed from its naturally occurring environment, and includes recombinant or cloned DNA isolates and chemically synthesized analogues or analogues biologically synthesized by heterologous systems. A substantially pure nucleic acid molecule includes isolated forms of the nucleic acid molecule.

"Vector" includes shuttle and expression vectors and includes, e.g., a plasmid, cosmid, or phagemid. Typically, a plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in prokaryotic, e.g., bacterial, or eukaryotic cells. Suitable vectors are disclosed below.

The cell that produces an anti-Lp-PLA2 antibody of the invention will include the parent hybridoma cell e.g., the hybridomas that are deposited with the ATCC, as well as bacterial, yeast and eukaryotic host cells into which nucleic acid encoding the antibodies have been introduced. Suitable host cells are disclosed below.

As used herein, the term "acute care" means health-care or necessary treatment of a disease over a short period of time in which a patient is treated for a brief but severe episode of illness, such as CVD, myocardial infarction and stroke. Acute care is typically rendered in an emergency department, ambulatory care clinic, or other short-term stay facility. An acute care setting or timeframe means within half an hour, 1 hour, 2 hours, 3 hours, 4 hours, 5 hours or 6 hours.

"High" refers to a measure that is greater than normal, greater than a standard such as a predetermined measure or a subgroup measure or that is relatively greater than another subgroup measure. For example, high Lp-PLA2 refers to a measure of Lp-PLA2 that is greater than a normal Lp-PLA2 measure. A normal Lp-PLA2 measure may be determined according to any method available to one skilled in the art. High Lp-PLA2 may also refer to a measure that is equal to or greater than a predetermined measure, such as a predetermined cutoff. High Lp-PLA2 may also refer to a measure of Lp-PLA2 wherein a high Lp-PLA2 subgroup has relatively greater levels of Lp-PLA2 than another subgroup. For example, without limitation, according to the present specification, two distinct patient subgroups can be created by dividing samples around a mathematically determined point, such as, without limitation, a median, thus creating a subgroup whose measure is high (ie, higher than the median) and another subgroup whose measure is low. Lp-PLA2 can be measured by any method known to one skilled in the art such as, for example, without limitation, using the PLAC® Test, an Lp-PLA2 activity assay, an immunohistochemical (IHC) assay or using any standard method for detecting Lp-PLA2, including Lp-PLA2 mass and Lp-PLA2 activity. In some cases, a "high" expression level may comprise a range of expression that is very high and a range of expression that is "moderately high" where moderately high is a level of expression that is greater than normal, but less than "very high". Example ranges for high (including very high and moderately high) high Lp-PLA2 expression are provided in the literature cited herein, the PLAC Test product specification, in the present application and include >200 ng/mL, >201 ng/mL, >201.5 ng/mL, >210 ng/mL, >220 ng/mL, >230 ng/mL, >240 ng/mL, >250 ng/mL, >260 ng/mL, >270 ng/mL, >280 ng/mL, >290 ng/mL, >300 ng/mL, >100 ng/mL/min, >110 ng/mL/min, >120 ng/mL/min, >130 ng/mL/min, >140 ng/mL/min, >150 ng/mL/min, >160 ng/mL/min, >170 ng/mL/min, >180 ng/mL/min, >190 ng/mL/min, and >200 ng/mL/min.

"Likely to" (and "unlikely to"), as used herein, refers to an increased (or decreased) probability that an item, object, thing or person will occur. Thus, in one example, a subject that is likely to benefit from treatment with a thrombolytic agent has an increased probability of benefiting from treatment with a thrombolytic agent relative to a reference subject or group of subjects.

"Long," as used herein, refers to a time measure that is greater than normal, greater than a standard such as a predetermined measure or a subgroup measure that is relatively longer than another subgroup measure. For example, with respect to a patient's longevity, a long time progression refers to time progression that is longer than a normal time progression. Whether a time progression is long or not may be determined according to any method available to one skilled in the art. In one embodiment, "long" refers to a time that is greater than the median time course required for a significant event to occur in a disease.

"Low" is a term that refers to a measure that is less than normal, less than a standard such as a predetermined measure or a subgroup measure that is relatively less than another subgroup measure. For example, low Lp-PLA2 means a measure of Lp-PLA2 that is less than a normal Lp-PLA2 measure in a particular set of samples of patients. A normal Lp-PLA2 measure may be determined according to any method available to one skilled in the art. Low Lp-PLA2 may also mean a measure that is less than a predetermined measure, such as a predetermined cutoff. Low Lp-PLA2 may also mean a measure wherein a low Lp-PLA2 subgroup is relatively lower than another subgroup. For example, without limitation, according to the present specification, two distinct patient subgroups can be created by dividing samples around a mathematically determined point, such as, without limitation, a median, thus creating a group whose measure is low (i.e., less than the median) with respect to another group whose measure is high (i.e., greater than the median). Lp-PLA2 can be measured by any method known to one skilled in the art such as, for example, without limitation, using the PLACE) Test, an Lp-PLA2 activity assay, an immunohistochemical (IHC) assay or using any standard method for detecting Lp-PLA2, including Lp-PLA2 mass and Lp-PLA2 activity. Example ranges for low values of Lp-PLA2 expression are provided in the literature cited herein, the PLAC Test product specification, in the present application and include <200 ng/mL, <201 ng/mL, <201.5 ng/mL, <210 ng/mL, <220 ng/mL, <230 ng/mL, <240 ng/mL, <250 ng/mL, <260 ng/mL, <270 ng/mL, <280 ng/mL, <290 ng/mL, <300 ng/mL, <100 ng/mL/min, <110 ng/mL/min, <120 ng/mL/min, <130 ng/mL/min, <140 ng/mL/min, <150 ng/mL/min, <160 ng/mL/min, <170 ng/mL/min, <180 ng/mL/min, <190 ng/mL/min, and <200 ng/mL/min.

"Overall survival" or "OS" refers to a time as measured from the start of treatment to death or censor. Censoring may come from a study end or change in treatment. Overall survival can refer to a probability as, for example, a probability when represented in a Kaplan-Meier plot of being alive at a particular time, that time being the time between the start of the treatment to death or censor.

"Pre-determined cutoff" as used herein, refers to the value of a predetermined measure on subjects exhibiting certain attributes that allow the best discrimination between two or more categories of an attribute. For example, a pre-determined cutoff that allows one to discriminate between two categories such as high Lp-PLA2 expression and low Lp-PLA2 expression for determining overall survival may be used. Pre-determined cutoffs may be used to separate the subjects with values lower than or higher than the pre-determined cutoff to optimize the prediction model.

"Respond" to treatment, and other forms of this verb, as used herein, refer to the reaction of a subject to treatment with an agent. As an example, a subject responds to treatment with an agent if the subject experiences a life expectancy extended by about 5%, 10%, 20%, 30%, 40%, 50% or more beyond the life expectancy predicted if no treatment is administered. In another example, a subject responds to treatment with an agent if the subject has an overall survival or increased time to progression. Several methods may be used to determine if a patient responds to a treatment.

"Sample" or "tissue sample" or "patient sample" or "patient cell or tissue sample" or "specimen" each refers to a collection of bodily fluid, tissue, or similar cells obtained from a tissue of a subject or patient. The source of the sample may be solid tissue as from a fresh tissue, frozen and/or preserved organ or tissue or biopsy or aspirate; blood or any blood constituents, bodily fluids such as cerebral spinal fluid, amniotic fluid, peritoneal fluid or interstitial fluid or cells from any time in gestation or development of the subject. The sample may contain compounds that are not naturally intermixed with the tissue in nature such as preservatives, anticoagulants, buffers, fixatives, nutrients, antibiotics or the like. Cells may be fixed in a conventional manner, such as in an FFPE manner.

"Short," as used herein, refers to a time measure that is shorter than normal, shorter than a standard such as a predetermined measure or a subgroup measure that is relatively shorter than another subgroup measure. For example, with respect to a patient's longevity, a short time progression refers to time progression that is shorter than a normal time progression or shorter than predicted. Whether a time progression is short or not may be determined according to any method available to one skilled in the art. In one embodiment, "short" refers to a time that is less than the median time course required for a significant event to occur in a disease.

"Significant event," as used herein, shall refer to an event in a patient's disease that is important as determined by one skilled in the art. Examples of significant events include, for example, without limitation, primary diagnosis, myocardial infarction, stroke, TIA, CVA, death, recurrence, the determination that a patient's disease is metastatic, relapse of a patient's disease or the progression of a patient's disease from any one of the above noted stages to another. A significant event may be any important event used to assess OS, TTP and/or other response criteria, as determined by one skilled in the art.

As used herein, the terms "subject" and "patient" are used interchangeably. As used herein, the terms "subject" and "subjects" refer to an animal, preferably a mammal including a non-primate (e.g., a cow, pig, horse, donkey, goat, camel, cat, dog, guinea pig, rat, mouse or sheep) and a primate (e.g., a monkey, such as a cynomolgus monkey, gorilla, chimpanzee or a human).

"Treatment," and other forms of this word, including "therapy", refer to the administration of an agent to impede a disease, such as progression of CVD, to cause a reduction in risk for CVD, to extend the expected survival time of the subject and/or time to progression of the CVD or the like. Treatment may include prophylactic or preventative measures. Treatment may also refer to any course which one skilled, for example, a treating physician, deems expedient.

The term "alleviate" means to reduce, diminish, or eliminate.

"Chemotherapeutic agent" means a chemical substance that is used to treat a condition, particularly cardiovascular disease.

As used herein, the term "metabolic disorder" includes a disorder, disease or condition which is caused or characterized by an abnormal metabolism (i.e., the chemical changes in living cells by which energy is provided for vital processes and activities) in a subject. Metabolic disorders include diseases, disorders, or conditions associated with hyperglycemia or aberrant adipose cell (e.g., brown or white adipose cell) phenotype or function. Metabolic disorders can detrimentally affect cellular functions such as cellular proliferation, growth, differentiation, or migration, cellular regulation of homeostasis, inter- or intra-cellular communication; tissue function, such as liver function, renal function, or adipocyte function; systemic responses in an organism, such as hormonal responses (e.g., insulin response). Examples of metabolic disorders include obesity, diabetes, hyperphagia, endocrine abnormalities, triglyceride storage disease, Bardet-Biedl syndrome, Lawrence-Moon syndrome, Prader-Labhart-Willi syndrome, anorexia, and cachexia. Obesity is defined as a body mass index (BMI) of 30 kg/m.sup.2 or more (National Institute of Health, Clinical Guidelines on the Identification, Evaluation, and Treatment of Overweight and Obesity in Adults (1998)). However, the invention is also intended to include a disease, disorder, or condition that is characterized by a body mass index (BMI) of 25 kg/m2 or more, 26 kg/m2 or more, 27 kg/m.sup.2 or more, 28 kg/m.sup.2 or more, 29 kg/m.sup.2 or more, 29.5 kg/m.sup.2 or more, or 29.9 kg/m.sup.2 or more, all of which are typically referred to as overweight (National Institute of Health, Clinical Guidelines on the Identification, Evaluation, and Treatment of Overweight and Obesity in Adults (1998)).

As used herein, "greater than or equal to" (i.e., $>=$) can in certain alternative embodiments mean "greater than" ($>$). Also, as used herein, "less than or equal to" (i.e., $\leq$ or $<=$) can in certain alternative embodiments mean "less than" ($<$).

Agents for reducing the risk of a Coronary Vascular Disorder include those selected from the group consisting of Lp-PLA2 compounds (Leach 2001), anti-inflammatory agents, anti-thrombotic agents, anti-platelet agents, fibrinolytic agents, lipid reducing agents, niacin, direct thrombin inhibitors, and glycoprotein II b/IIIa receptor inhibitors and agents that bind to cellular adhesion molecules and inhibit the ability of white blood cells to attach to such molecules (e.g. anti-cellular adhesion molecule antibodies).

Anti-inflammatory agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobuten; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium.

Anti-thrombotic and/or fibrinolytic agents include Plasminogen (to plasmin via interactions of prekallikrein, kininogens, Factors XII, XIIIa, plasminogen proactivator, and tissue plasminogen activator[TPA]) Streptokinase; Urokinase: Anisoylated Plasminogen-Streptokinase Activator Complex; Pro-Urokinase; (Pro-UK); rTPA (alteplase or activase; r denotes recombinant), rPro-UK; Abbokinase; Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; retaplase; Trifenagrel; Warfarin; Dextrans.

Anti-platelet agents include Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine; Anagrelide. Lipid reducing agents include gemfibrozil, cholystyramine, colestipol, nicotinic acid, probucol lovastatin, fluvastatin, simvastatin, atorvastatin, pravastatin, cirivastatin (for statins, see Crouch 2000). Direct thrombin inhibitors include hirudin, hirugen, hirulog, agatroban, PPACK, thrombin aptamers. Glycoprotein receptor Inhibitors are both antibodies and non-antibodies, and include but are not limited to ReoPro (abcixamab), lamifiban, tirofiban. One preferred agent is aspirin.

Markers of systemic inflammation, such as CRP, are well-known to those of ordinary skill in the art. It is preferred that the markers of systemic inflammation be selected from the group consisting of C-reactive protein, cytokines, and cellular adhesion molecules. Cytokines are well-known to those of ordinary skill in the art and include human interleukins 1-17. Cellular adhesion molecules are well-known to those of ordinary skill in the art and include integrins, ICAM-1, ICAM-3, BL-CAM, LFA-2, VCAM-1, NCAM, and PECAM. The preferred adhesion molecule is soluble intercellular adhesion molecule (sICAM-1).

Biomarkers associated with CVD are well-known to those of skill in the art and include, but are not limited to: Age, ALB, Bmi, CHOL, CKB (Creatine kinase, brain (CKB), BB-CK, creatine phosphokinase (CPK), Part of CKMB), CKM (Creatine kinase, muscle (CKM), MM-CK, Part of CKMB), CRP, Diastolic Blood Pressure, Factor VIII (FVIII), anti-hemophilic factor (AHF), Family History, FGA (Fibrinogen AC, converted to Fibrin, d-dimer), FTH1, Gender, Glucose, HBA1C, HDL-C, Hip (Circumference), Homocysteine, HP, LPA, Race, Systolic Blood Pressure, SHBG, Triglycerides, VWF, Waist (Circumference), Weight, TNNI3, TNNT2, LDL-C, INS (Insulin, Soluble C-Peptide), PLA2G7, ANG (Angiogenin, ribonuclease, RNase A family, 5), APOA1, APOB, APOE, CD40, DPP4 (CD26), IL6ST (Interleukin-6 Signal Transducer, Glycoprotein 130, gp130, oncostatin M receptor, IL6ST, IL6-beta or CD130), POMC, VCAM1, GDF15, IL1RL1, CCL2, MPO, D-dimer, GPT, IGF1, LEP, VEGFA, CDK5, EGF, FABP3, IGFBP1, IL18, IL2RA, IL6R, IL8, NPPB (Brain natriuretic peptide (BNP), B-type natriuretic peptide, GC-B, Pro-BNP, NT-pro-BNP), SELE, TNFRSF1B (Tumor necrosis factor receptor superfamily, member 1B (TNFRSF1B), TNFR2, CD120b, p75, TNF-R-II, TNF-R75, TNFRB, TNFR80), IL6, RETN, Ox-LDL, TNFRSF1A, ACE, ADIPOQ, AGER, AHSG, ANGPT2, APOA2, BAX, C4A, CCL11, CCL13, CCL7, CD14, CFD, CSF1, CXCL10, ENG, FAS, FASLG, HGF, ICAM1, IFNG, IGFBP3, IL3, IL5, IL7, INHBA, MMP2, MMP3, MMP9, NGF, PLAT (plasminogen activator, tissue, tPA), SAA1, SELP (Selectin P, GRMP, granule membrane protein 140 kD (GMP140), CD62, PSEL, PADGEM), TGFB1, TNF, REN, MB, ADM, CST3, LGALS3, NPPA (Atrial natriuretic peptide (ANP), atrial natriuretic factor (ANF), atrial natriuretic hormone (ANH), Cardionatrine, Cardiodilatine (CDD) or atriopeptin, MR-ANP), Creatinine, FLT1, Adrenolutin, AGT, AVP, CLU, EDN1, EPO, GSH, LCN2, MDA, MDA-LDL, MYL2, Norepi (Norepinephrine (abbreviated norepi or NE), noradrenaline (NA, NAd, or norad)), S100A12, SERPINE1, SFTPB, SPP1, CHGA, CHGB, IL19, RLN1, TNFRSF11B, APCS, APOC3, APOH, Cardiolipin, CCL12, CCL19, CCL21, CCL3, CCL4, CCL5, CCL8, CCL9, CPB, CSF3, CXCL1, CXCL2, F2, IGFBP2, IL10, IL12B, IL13, IL1B, IL2, IL4, MMP1, MMP10, MMP7, Neopterin, OLR1, PDGFB, PF4, SERPINA7, THBD, TIMP1, and TNFSF11.

Compositions and Methods of the Invention

The invention provides anti-Lp-PLA2 antibodies. The anti-Lp-PLA2 antibodies may also internalize to vascular plaques upon binding to Lp-PLA2.

The anti-Lp-PLA2 antibodies of the invention also have various non-therapeutic applications. The anti-Lp-PLA2 antibodies of the present invention can be useful for diagnosis and staging of Lp-PLA2-related disease (e.g., in radioimaging). They may be used alone or in combination with other biomarkers, including, but not limited to inflammation and CVD biomarkers described herein. The antibodies are also useful for purification or immunoprecipitation of Lp-PLA2 from cells, for detection and quantitation of Lp-PLA2 in vitro, e.g. in an ELISA or a Western blot. The internalizing anti-Lp-PLA2 antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies, an antibody sequence is fused to a heterologous polypeptide sequence. The antibodies can be modified in the Fc region to provide desired effector functions. As discussed in more detail in the sections below, with the appropriate Fc regions, the naked antibody bound on a cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

The antibody may compete for binding, or binds substantially to, the same epitope bound by the antibodies of the invention. Antibodies having the biological characteristics of the present anti-Lp-PLA2 antibodies of the invention are also contemplated, e.g., an anti-Lp-PLA2 antibody which has the biological characteristics of a monoclonal antibody described herein. Specifically provided are anti-Lp-PLA2 antibodies that bind to an epitope present on human Lp-PLA2.

Methods of producing the above antibodies are described in detail below.

The present anti-Lp-PLA2 antibodies are useful for treating a Lp-PLA2-related disease or alleviating one or more symptoms of the disease in a mammal. The antibody is able to bind to at least a portion of Lp-PLA2 in the mammal and preferably is one that does not induce or that minimizes HAMA response. Preferably, the antibody is effective to destroy vascular plaque, in vitro or in vivo, upon binding to Lp-PLA2. Such an antibody includes a naked anti-Lp-PLA2 antibody (not conjugated to any agent). Naked anti-Lp-PLA2 antibodies having inhibition properties in vivo include the antibodies described in the Experimental Examples below. Naked antibodies that have cytotoxic or inhibition properties can be further conjugated with a cytotoxic agent to render them even more potent. Cytotoxic properties can be conferred to an anti-Lp-PLA2 antibody by, e.g., conjugating the antibody with a cytotoxic agent, to form an immunoconjugate as described below. The cytotoxic agent or a therapeutic agent is preferably a small molecule. Toxins such as maytansin, maytansinoids, saporin, gelonin, ricin or calicheamicin and analogs or derivatives thereof, are preferable.

The invention provides a composition comprising an anti-Lp-PLA2 antibody of the invention, and a carrier. For the purposes of treating vascular disease, compositions can be administered to the patient in need of such treatment, wherein the composition can comprise one or more anti-Lp-PLA2 antibodies present as an immunoconjugate or as the naked antibody. Further, the compositions can comprise these antibodies in combination with other therapeutic agents described above. The invention also provides formulations comprising an anti-Lp-PLA2 antibody of the invention, and a carrier. The formulation may be a therapeutic formulation comprising a pharmaceutically acceptable carrier.

Another aspect of the invention is isolated nucleic acids encoding the anti-Lp-PLA2 antibodies. Nucleic acids encoding both the H and L chains and especially the hypervariable region residues, chains which encode the native sequence antibody as well as variants, modifications and humanized versions of the antibody, are encompassed.

Finally, the invention also provides kits and articles of manufacture comprising at least one antibody of this invention, preferably at least one anti-Lp-PLA2 antibody of this invention. Kits containing anti-Lp-PLA2 antibodies find use in detecting Lp-PLA2 expression, or in therapeutic or diagnostic assays, e.g., for purification and/or immunoprecipitation of Lp-PLA2 from cells, tissues or bodily fluids. For example, for isolation and purification of Lp-PLA2, the kit can contain an anti-Lp-PLA2 antibody coupled to a solid support, e.g., a tissue culture plate or beads (e.g., sepharose beads). Kits can be provided which contain antibodies for detection and quantitation of Lp-PLA2 in vitro, e.g. in an ELISA or a Western blot. Such antibody useful for detection may be provided with a label such as a fluorescent or radiolabel.

Production of anti-Lp-PLA2 Antibodies

The following describes exemplary techniques for the production of the antibodies useful in the present invention. Some of these techniques are described further in Example 1. The Lp-PLA2 antigen to be used for production of antibodies may be, e.g., the full length polypeptide or a portion thereof, including a soluble form of Lp-PLA2, a catalytic peptide, or synthetic peptides to selected portions of the protein.

The nucleotide and amino acid sequences of human and murine Lp-PLA2 are available as provided above. Lp-PLA2 can be produced recombinantly in and isolated from, prokaryotic cells, e.g., bacterial cells, or eukaryotic cells using standard recombinant DNA methodology. Lp-PLA2 can be expressed as a tagged (e.g., epitope tag) or other fusion protein to facilitate its isolation as well as its identification in various assays.

Antibodies or binding proteins that bind to various tags and fusion sequences are available as elaborated below. Other forms of Lp-PLA2 useful for generating antibodies will be apparent to those skilled in the art.

Tags

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). The FLAG-peptide (Hopp et al., BioTechnology, 6:1204-1210 (1988)) is recognized by an anti-FLAG M2 monoclonal antibody (Eastman Kodak Co., New Haven, Conn.). Purification of a protein containing the FLAG peptide can be performed by immunoaffinity chromatography using an affinity matrix comprising the anti-FLAG M2 monoclonal antibody covalently attached to agarose (Eastman Kodak Co., New Haven, Conn.). Other tag polypeptides include the KT3 epitope peptide [Martin et al., Science, 255:192-194 (1992)]; an α-tubulin epitope peptide (Skinner et al., J. Biol. Chenz., 266:15163-15166 (1991)); and the T7 gene protein peptide tag (Lutz-Freyermuth et al., Proc. Natl. Acad. Sci. USA, 87:6393-6397 (1990)).

Polyclonal Antibodies

Polyclonal antibodies are preferably raised in animals, preferably non-human animals, by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraidehyde, succinic anhydride, $SOCl_2$, or $R^1N=C=NR$, where R and $R^1$ are different alkyl groups. Conjugates also can be made in recombinant cell culture as protein fusions.

Animals are immunized against the antigen, immunogenic conjugates, or derivatives by combining, e.g., 5-100 pg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by recombinant DNA methods (U.S. Pat. No. 4,816,567). In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a "fusion partner", e.g., a myeloma cell line using a suitable fusing agent, such as polyethylene glycol, to form a hybridoma cell (Goding, Monoclonal Antibodies. Principles and Practice, pp 103 (Academic Press, 1986)).

The hybridoma cells thus prepared are seeded and grown in a suitable culture medium which medium preferably contains one or more substances that inhibit the growth or survival of the unfused, fusion partner, e.g, the parental myeloma cells. For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-II mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980). Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp 103 (Academic Press, 1986)). Suitable culture media for this purpose include, for example, D-MEM or RPMI-1640 medium. In addition, the hybridoma cells may be grown in vivo as ascites tumors in an animal e.g, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transformed or transfected into prokaryotic or eukaryotic host cells such as, e.g., E coli cells, simian COS cells, Chinese Hamster Ovary (CHO) cells, or myeloma cells, that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Phickthun, Immunol. Revs., 130:151-188 (1992).

Further, the monoclonal antibodies or antibody fragments can be isolated from antibody phage libraries generated using the techniques described in McCafferty et al., Nature, 348: 552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl Acad. Sci. USA, 81:6851 (1984)), or by fusing the immunoglobulin coding sequence with all or part of the coding sequence for a nonimmunoglobulin polypeptide (heterologous polypeptide). The nonimmunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized Antibodies

Methods for humanizing non-human antibodies have been described in the art. Preferably, a humanized antibody has one or more amino acid residues introduced into it from a source which is nonhuman. These non-human amino acid residues are often referred to as "import" residues, which are typically taken from an "import" variable domain. Humanization can be essentially performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art.

Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-Lp-PLA2 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and Alternatively, phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of antioxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905. As discussed above, human antibodies may also be generated by in vitro activated B cells (see U.S. Pat. Nos. 5,567,610 and 5,229,275).

Antibody Fragments

In certain circumstances there are advantages of using antibody fragments, rather than whole antibodies. The smaller size of the fragments allows for rapid clearance, and may lead to improved access to solid tumors. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E coli, thus allowing the facile production of large amounts of these fragments. Antibody fragments can be isolated from the antibody phage libraries discussed above. Alternatively, Fab'-SH fragments can be directly recovered from E. coli and chemically coupled to foam F(ab)2 fragments (Carter et al., Bio/Technology 10: 163-167 (1992)). According to another approach, F(ab)2 fragments can be isolated directly from recombinant host cell culture. Fab and F(ab)2 fragment with increased in vivo half-life comprising a salvage receptor binding epitope residues are described in U.S. Pat. No. 5,869,046. Other techniques for the production of antibody fragments will be apparent to the skilled practitioner. The antibody of choice may also be a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of the Lp-PLA2 protein. Other such antibodies may combine an Lp-PLA2 binding site with a binding site for another protein. Alternatively, an anti-Lp-PLA2.Arm may be combined with an arm which binds to a triggering molecule on a leukocyte such as a Tcell receptor molecule (e.g. C133), or Fc receptors for IgG (FcγR), such as FcγRI (CD64), FcγRII (CD32) and FcγRIII (CD16), so as to focus and localize cellular defense mechanisms to the Lp-PLA2-expressing cell. Bispecific antibodies may also be used to localize cytotoxic agents to cells which express Lp-PLA2. These antibodies possess an Lp-PLA2-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab)2 bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region (CHI) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Preferably, the bispecific antibodies in this approach are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

The "diabody" technology described by Hollinger et al., Proc. Natl. Acad. Sci. USA, 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1(X1n-VD2-(X2)n-Fc, wherein VDI is a first variable domain, VD2 is a second variable domain, Fc is one polypeptide chain of an Fe region, XI and X2 represent an amino acid or polypeptide, and n is 0 or 1. For instance, the polypeptide chain(s) may comprise: VH-CHI-flexible linker-VH-CHI-Fc region chain; or VH-CHI-VH-CHI-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Other Amino Acid Sequence Modifications

Amino acid sequence modification(s) of the anti-Lp-PLA2 antibodies described herein are contemplated. For example, it may be desirable to improve the binding affinity and/or other biological properties of the antibody. Amino acid sequence variants of the anti-Lp-PLA2 antibody are prepared by introducing appropriate nucleotide changes into the anti-Lp-PLA2 antibody nucleic acid, or by peptide synthesis.

Such modifications include, for example, deletions from, and/or insertions into, and/or substitutions of, residues within the amino acid sequences of the anti-Lp-PLA2 antibody. Any combination of deletion, insertion, and substitution is made to arrive at the final construct, provided that the final construct possesses the desired characteristics. The amino acid changes also may alter post-translational processes of the anti-Lp-PLA2 antibody, such as changing the number or position of glycosylation sites.

A useful method for identification of certain residues or regions of the anti-Lp-PLA2 antibody that are preferred locations for mutagenesis is called "alanine scanning mutagenesis" as described by Cunningham and Wells in Science, 244:1081-1085 (1989). Here, a residue or group of target residues within the anti-Lp-PLA2 antibody are identified (e.g., charged residues such as arg, asp, his, lys, and glu) and replaced by a neutral or negatively charged amino acid (most preferably alanine or polyalanine) to affect the interaction of the amino acids with Lp-PLA2 antigen.

Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at a target codon or region and the expressed anti-Lp-PLA2 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-Lp-PLA2 antibody with an N-terminal methionyl residue or the antibody fused to a cytotoxic polypeptide. Other insertional variants of the anti-Lp-PLA2 antibody molecule include the fusion to the N- or C-terminus of the anti-Lp-PLA2 antibody to an enzyme (e.g. for ADEPT) or a fusion to a polypeptide which increases the serum half-life of the antibody.

Another type of variant is an amino acid substitution variant. These variants have at least one amino acid residue in the anti-Lp-PLA2 antibody molecule replaced by a different residue. The sites of greatest interest for substitutional mutagenesis include the hypervariable regions, but FR alterations are also contemplated. Conservative substitutions are shown in Table I under the heading of "preferred substitutions". If such substitutions result in a change in biological activity, then more substantial changes, denominated "exemplary substitutions" in the table below, or as further described below in reference to amino acid classes, may be introduced and the products screened for a desired characteristic.

| Amino Acid Substitutions | | |
|---|---|---|
| Original Residue | Exemplary Substitutions | Preferred Substitutions |
| Ala (A) | val; leu; ile | Val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gin; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | Phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gin, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the anti-Lp-PLA2 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human Lp-PLA2. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-Lp-PLA2 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared nucleic acid molecule encoding a variant or a non-variant version of the anti-Lp-PLA2 antibody.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of the antibody.

Screening for Antibodies with the Desired Properties

Techniques for generating antibodies have been described above. One may further select antibodies with certain biological characteristics, as desired.

The therapeutic effects of an anti-Lp-PLA2 antibody of the invention may be assessed by methods known in the art, e.g., using cells which express Lp-PLA2 either endogenously or following transfection with the Lp-PLA2 gene. For example, cells or tissues with native Lp-PLA2 or Lp-PLA2-transfected cells may be treated with an anti-Lp-PLA2 monoclonal antibody of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-Lp-PLA2 antibody of the invention. After antibody treatment, the cells are harvested and the amount of radioactivity incorporated into the DNA quantitated in a scintillation counter. Appropriated positive controls include treatment of a selected cell line with a therapeutic antibody known to inhibit growth of that cell line. Growth inhibition of tumor cells in vivo can be determined in various ways such as is described in the Experimental Examples section below. Preferably, the cell is one that over-expresses Lp-PLA2. Preferably, the anti-Lp-PLA2 antibody will inhibit cell proliferation of an Lp-PLA2-expressing cell in vitro or in vivo by about 25-100% compared to the untreated cell, more preferably, by about 30-100%, and even more preferably by about 50-100% or 70-100%, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the cells to the antibody.

To select for antibodies which induce cell death, loss of membrane integrity as indicated by, e.g., propidium iodide (PI), trypan blue or 7AAD uptake may be assessed relative to a control. A PI uptake assay can be performed in the absence of complement and immune effector cells. Lp-PLA2-expressing cells are incubated with medium alone or medium containing of the appropriate monoclonal antibody at e.g., about 10 µg/ml. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies.

To screen for antibodies which bind to an epitope on Lp-PLA2 bound by an antibody of interest, e.g., the Lp-PLA2 antibodies of this invention, a routine cross-blocking assay such as that describe in *Antibodies, A Laboratory Manual*, Cold Spring Harbor Laboratory, Ed Harlow and David Lane (1988), can be performed. This assay can be used to determine if a test antibody binds the same site or epitope as an anti-Lp-PLA2 antibody of the invention. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of Lp-PLA2 can be used in competition assays with the test antibodies or with a test antibody and an antibody with a characterized or known epitope.

For example, a method to screen for antibodies that bind to an epitope which is bound by an antibody this invention may comprise combining an Lp-PLA2-containing sample with a test antibody and an antibody of this invention to form a mixture, the level of Lp-PLA2 antibody bound to Lp-PLA2 in the mixture is then determined and compared to the level of Lp-PLA2 antibody bound in the mixture to a control mixture, wherein the level of Lp-PLA2 antibody binding to Lp-PLA2 in the mixture as compared to the control is indicative of the test antibody's binding to an epitope that is bound by the anti-Lp-PLA2 antibody of this invention. The level of Lp-PLA2 antibody bound to Lp-PLA2 is determined by ELISA. The control may be a positive or negative control or both. For example, the control may be a mixture of Lp-PLA2, Lp-PLA2 antibody of this invention and an antibody known to bind the epitope bound by the Lp-PLA2 antibody of this invention. The anti-Lp-PLA2 antibody labeled with a label such as those disclosed herein. The Lp-PLA2 may be bound to a solid support, e.g., a tissue culture plate or to beads, e.g., sepharose beads.

Immunoconjugates and Cytotoxic Agents

The invention also pertains to therapy with immunoconjugates comprising an antibody conjugated to an agent such as a therapeutic agent.

For selective destruction of the cells, the antibody may comprise a highly radioactive atom. A variety of radioactive isotopes are available for the production of radioconjugated anti-Lp-PLA2 antibodies. Examples include $At^{211}$, $I^{131}$, $In^{111}$, $Y^{90}$, $Re^{186}$, $Re^{188}$, $Sm^{153}$, $Bi^{212}$, $P^{32}$, and radioactive isotopes of Lu. When the conjugate is used for diagnosis, it may comprise a radioactive atom for scintigraphic studies, for example $Tc^{99M}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $Tc^{99M}$, $I^{123}$, $In^{111}$, $Re^{186}$, $Re^{188}$, can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine "Monoclonal Antibodies in Immunoscintigraphy" (Chatal, CRC Press 1989) describes other methods in detail.

Conjugates of the antibody and therapeutic agent may be made using a variety of bifunctional protein coupling agents such as N-succinimidyl(2-pyridyldithio) propionate (SPDP), succinimidyl(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). The linker may be a "cleavable linker" facilitating release of the therapeutic agent. For example, an acid-labile linker, peptidase-sensitive linker, photolabile linker, dimethyl linker or disulfide-containing linker (Chari et al. Cancer Research 52: 127-131 (1992); U.S. Pat. No. 5,208,020) may be used.

Alternatively, a fusion protein comprising the anti-Lp-PLA2 antibody and therapeutic agent may be made, e.g. by recombinant techniques or peptide synthesis. The length of DNA may comprise respective regions encoding the two portions of the conjugate either adjacent one another or separated by a region encoding a linker peptide which does not destroy the desired properties of the conjugate.

Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active drug. See, for example, WO 88/07378 and U.S. Pat. No. 4,975,278.

Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The anti-Lp-PLA2 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A che- Vectors, Host Cells, and Recombinant Methods The invention also provides isolated nucleic acid molecule encoding the humanized anti-Lp-PLA2 antibody, vectors and host cells comprising the nucleic acid, and recombinant techniques for the production of the antibody. For recombinant production of the antibody, the nucleic acid molecule encoding it is isolated and inserted into a replicable vector for further cloning (amplification of the DNA) or inserted into a vector in operable linkage with a promoter for expression. DNA encoding the monoclonal antibody is readily isolated and sequenced using conventional procedures (e.g., by using oligonucleotide probes that are capable of binding specifically to nucleic acid molecules encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Selection and Transformation of Host Cells

Suitable host cells for cloning or expressing the DNA in the vectors herein are the prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W31 10 (ATCC 27,325) are suitable. These examples are illustrative rather than limiting.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-Lp-PLA2 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactic, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244, 234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-Lp-PLA2 antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of Autographa californica NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, *Arabidopsis* and tobacco can also be utilized as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, 1413 8065); mouse mammary tumor (MMT 060562, ATCC CCL5 1); TRI cells (Mather et al., Annals N. Y Acad. Sci. 383:44-68 (1982)); MRC 5 cells; FS4 cells; and a human hepatoma line (Hep G2).

Host cells are transformed with the above-described expression or cloning vectors for anti-Lp-PLA2 antibody production and cultured in conventional nutrient media modified as appropriate for inducing promoters, selecting transformants, or amplifying the genes encoding the desired sequences.

Culturing Host Cells

The host cells used to produce the anti-Lp-PLA2 antibody of this invention may be cultured in a variety of media. Commercially available media such as Ham's FIO (Sigma), Minimal Essential Medium (MEM) (Sigma), RPMI-1640 (Sigma), and Dulbecco's Modified Eagle's Medium (DMEM) (Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or U.S. Pat. No. 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Anti-Lp-PLA2 Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SIDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Pharmaceutical formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol, and mcresol); low molecular weight (less than about 10 residues) polypeptides; proteins, such as serum albumin, gelatin, or immunoglobulins; hydrophilic polymers such as polyvinylpyllolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). The antibody preferably comprises the antibody at a concentration of between 5-200 mg/ml, preferably between 10-100 mg/ml.

The formulation herein may also contain more than one active compound as necessary for the particular indication being treated, preferably those with complementary activities that do not adversely affect each other. For example, in addition to the anti-Lp-PLA2 antibody which internalizes, it may be desirable to include in the one formulation, an additional antibody, e.g. a second anti-Lp-PLA2 antibody which binds a different epitope on Lp-PLA2, or a therapeutic for an Lp-PLA2 related disease. Alternatively, or additionally, the composition may further comprise a chemotherapeutic agent, cytotoxic agent, cytokine, therapeutic agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatinmicrocapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−) hydroxybutyric acid.

The formulations to be used for in vivo administration must be sterile. This is readily accomplished by filtration through sterile filtration membranes.

Methods and Treatment Using Anti-Lp-PLA2 Antibodies

According to the present invention, the anti-Lp-PLA2 antibody that binds to Lp-PLA2 is used to treat a subject in need thereof having an Lp-PLA2 related disease, in particular, cardiovascular diseases.

While the Lp-PLA2 related disease may be characterized by overexpression of Lp-PLA2, the present application further provides a method for treating Lp-PLA2 related disease which is not considered to be an Lp-PLA2-overexpressing disease.

This invention also relates to methods for detecting cells or tissues which overexpress Lp-PLA2 and to diagnostic kits useful in detecting cells or tissues expressing Lp-PLA2 or in detecting Lp-PLA2 in bodily fluids from a patient. Bodily fluids include blood, serum, plasma, urine, ascites, peritoneal wash, saliva, sputum, seminal fluids, tears, mucous membrane secretions, and other bodily excretions such as stool. The methods may comprise combining a cell-containing test sample with an antibody of this invention, assaying the test sample for antibody binding to cells in the test sample and comparing the level of antibody binding in the test sample to the level of antibody binding in a control sample of cells. A suitable control is, e.g., a sample of tissue or normal cells of the same type as the test sample or a cell sample known to be free of Lp-PLA2 overexpressing cells. A level of Lp-PLA2 binding higher than that of such a control sample would be indicative of the test sample overexpressing Lp-PLA2. Alternatively the control may be a sample of tissue or cells known to contain cells that overexpress Lp-PLA2. In such a case, a level of Lp-PLA2 antibody binding in the test sample that is similar to, or in excess of, that of the control sample would be indicative of the test sample containing cells that overexpress Lp-PLA2.

Additionally, the methods may comprise combining a test sample with an antibody of this invention, assaying the test sample for antibody binding to Lp-PLA2 in the test sample and comparing the level of antibody binding in the test sample to the level of antibody binding in a control sample. A suitable control is, e.g., a non-diseased sample of the same type as the test sample, sample known to be free of Lp-PLA2 or a sample of known quantity of Lp-PLA2. A level of Lp-PLA2 binding higher than that of such a control sample would be indicative of the test sample containing overexpression of Lp-PLA2. Alternatively the control may be a sample known to overexpress Lp-PLA2. In such a case, a level of Lp-PLA2 antibody binding in the test sample that is similar to, or in excess of, that of the control sample would be indicative of the test sample overexpressing Lp-PLA2.

Lp-PLA2 overexpression may be detected with a various diagnostic assays. For example, over expression of Lp-PLA2 may be assayed by immunohistochemistry (IHC). Parrafin embedded or fresh/frozen tissue sections from a biopsy may be subjected to the IHC assay and accorded an Lp-PLA2 protein staining intensity criteria Alternatively, or additionally, FISH assays such as the INFORM™ (sold by Ventana, Ariz.) or PATHVISION™ (VySiS, Illinois) may be carried out on formalin-fixed, paraffin-embedded tissue to determine the extent (if any) of Lp-PLA2 overexpression in the tissue. Lp-PLA2 overexpression or amplification may be evaluated using an in vivo diagnostic assay, e.g. by administering a molecule (such as an antibody of this invention) which binds Lp-PLA2 and which is labeled with a detectable label (e.g. a radioactive isotope or a fluorescent label) and externally scanning the patient for localization of the label.

A sample suspected of containing cells expressing or overexpressing Lp-PLA2 is combined with the antibodies of this invention under conditions suitable for the specific binding of the antibodies to Lp-PLA2. Binding and/or internalizing the Lp-PLA2 antibodies of this invention is indicative of the cells expressing Lp-PLA2. The level of binding may be determined and compared to a suitable control, wherein an elevated level of bound Lp-PLA2 as compared to the control is indicative of Lp-PLA2 overexpression. A serum sample from a subject may also be assayed for levels of Lp-PLA2 by combining a serum sample from a subject with an Lp-PLA2 antibody of this invention, determining the level of Lp-PLA2 bound to the antibody and comparing the level to a control, wherein an elevated level of Lp-PLA2 in the serum of the patient as compared to a control is indicative of overexpression of Lp-PLA2 by cells in the patient. The subject may have a Lp-PLA2 related disease such as atherosclerosis.

The anti-Lp-PLA2 antibodies of the invention are useful to alleviate Lp-PLA2 related disease. For therapeutic applications, the anti-Lp-PLA2 antibody can be used alone, or in combination therapy. Anti-Lp-PLA2 antibody treatment can be administered in conjunction with other forms of conventional therapy, either consecutively with, pre- or post-conventional therapy. The anti-Lp-PLA2 antibody will be administered with a therapeutically effective dose of the conventional.

The anti-Lp-PLA2 antibodies or immunoconjugates are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies or immunoconjugates may be injected or delivered directly into the vascular plaque. Intravenous or subcutaneous administration of the antibody is preferred. Other therapeutic regimens may be combined with the administration of the anti-Lp-PLA2 antibody.

The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 pg/kg to about 50 mg/kg body weight (e.g. about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-Lp-PLA2 antibody. However, other dosage regimens may be useful. A typical daily dosage might range from about 1 pg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of a nucleic acid molecule encoding the antibody is encompassed by the expression "administering a therapeutically effective amount of an antibody". See, for example, WO 96/07321 published Mar. 14, 1996 concerning the use of gene therapy to generate intracellular antibodies.

There are two major approaches to introducing the nucleic acid molecule (optionally contained in a vector) into the patient's cells; in vivo and ex vivo. For in vivo delivery the nucleic acid molecule is injected directly into the patient, usually at the site where the antibody is required. For ex vivo treatment, the patient's cells are removed, the nucleic acid molecule is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acid molecules into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid molecule transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., Science 256:808-813 (1992). See also WO 93/25673 and the references cited therein.

Articles of Manufacture and Kits

The invention also relates to an article of manufacture containing materials useful for the detection of Lp-PLA2 levels in samples, Lp-PLA2 overexpressing cells and/or the treatment of Lp-PLA2 related disease, in particular CHD and atherosclerosis. The article of manufacture comprises a container and a composition contained therein comprising an antibody of this invention. The composition may further comprise a carrier. The article of manufacture may also comprise a label or package insert on or associated with the container. Suitable containers include, for example, bottles, vials, syringes, etc. The containers may be formed from a variety of materials such as glass or plastic. The container holds a composition which is effective for detecting Lp-PLA2 expressing cells and/or treating a condition and may have a sterile access port (for example the container may be an intravenous solution bag or a vial having a stopper pierceable by a hypodermic injection needle). At least one active agent in the composition is an anti-Lp-PLA2 antibody of the invention. The label or package insert indicates that the composition is used for detecting Lp-PLA2 levels, Lp-PLA2 expressing cells and/or for treating CHD, in a patient in need thereof. The label or package insert may further comprise instructions for administering the antibody composition to a patient. Additionally, the article of manufacture may further comprise a second container comprising a substance which detects the antibody of this invention, e.g., a second antibody which binds to the antibodies of this invention. The substance may be labeled with a detectable label such as those disclosed herein. The second container may contain e.g., a pharmaceutically-acceptable buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

Kits are also provided that are useful for various purposes, e.g. for purification or immunoprecipitation of Lp-PLA2 from cells or for detecting the presence of Lp-PLA2 in a bodily fluid sample or detecting the presence of Lp-PLA2-expressing cells in a cell sample. For isolation and purification of Lp-PLA2, the kit can contain an anti-Lp-PLA2 antibody coupled to a solid support, e.g., a tissue culture plate or beads (e.g., sepharose beads). Kits can be provided which contain the antibodies for detection and quantitation of Lp-PLA2 in vitro, e.g. in an ELISA or a Western blot. As with the article of manufacture, the kit comprises a container and a composition contained therein comprising an antibody of this invention. The kit may further comprise a label or package insert on or associated with the container. The kits may comprise additional components, e.g., diluents and buffers, substances which bind to the antibodies of this invention, e.g., a second antibody which may comprise a label such as those disclosed herein, e.g., a radiolabel, fluorescent label, or enzyme, or the kit may also comprise control antibodies. The additional components may be within separate containers within the kit. The label or package insert may provide a description of the composition as well as instructions for the intended in vitro or diagnostic use.

EXAMPLES

Example 1

Production and Isolation of Monoclonal Antibody Producing Hybridomas

The following MAb/hybridomas of the present invention are described below:

LpPLA2.A7.1, LpPLA2.A8.2, LpPLA2.A201.1, LpPLA2.A202.1, LpPLA2.A203.1, LpPLA2.B5.2, LpPLA2.B6, LpPLA2.B17.1, LpPLA2.B17.2, LpPLA2.B26, LpPLA2.B31, LpPLA2.B38.2, LpPLA2.B40, LpPLA2.B44, LpPLA2.B48, LpPLA2.B69, LpPLA2.B71, LpPLA2.B78, LpPLA2.B81, LpPLA2.B82, LpPLA2.B84, LpPLA2.B94, LpPLA2.B98, LpPLA2.B130, LpPLA2.B132, LpPLA2.B142, LpPLA2.B144.1, LpPLA2.B144.2, LpPLA2.B149, LpPLA2.B154, LpPLA2.B155, LpPLA2.B159.3, LpPLA2.B160, LpPLA2.B179, LpPLA2.B194, LpPLA2.B195, LpPLA2.B200.1, LpPLA2.B200.2, LpPLA2.B201.1, LpPLA2.B206, LpPLA2.B213, LpPLA2.B224, LpPLA2.B225, LpPLA2.B228, LpPLA2.B229.1, LpPLA2.B235, LpPLA2.B236, LpPLA2.B238, LpPLA2.B241, LpPLA2.B248, LpPLA2.B251, LpPLA2.B266, LpPLA2.B280, LpPLA2.B281, LpPLA2.B500.6, LpPLA2.B501.5, LpPLA2.C1, LpPLA2.C2, LpPLA2.C3, LpPLA2.C4, LpPLA2.C5, LpPLA2.C6, LpPLA2.C7, LpPLA2.C8, LpPLA2.C9,

LpPLA2.C10, LpPLA2.C11, LpPLA2.C12, LpPLA2.C13, LpPLA2.C14, LpPLA2.C15, LpPLA2.C16, LpPLA2.C18, LpPLA2.C19, LpPLA2.C201.1, and LpPLA2.C203.1.

If the MAb producing hybridoma has been cloned, it will get the nomenclature "X#0.1," e.g., the first clone of LpPLA2.A10 will be referred to as A10.1, the second clone of A10 will be referred to as A10.2, etc. Sub-clones are designated by a subsequent ".#", e.g. the first sub-clone of LpPLA2.A10.1 is referred to as A10.1.1, the second sub-clone of A10.1 is A10.1.2, etc. Further generations of sub-clones are annotated in the same format. For the purposes of this invention, a reference to an anti-Lp-PLA2 antibody producing hybridoma, e.g. LpPLA2.A10 or A10, will include all clones and sub-clones of the antibody, e.g., A10.1, A10.2, A10.1.1, etc. Furthermore, the nomenclature LpPLA2.A10.3, for example, may reference the antibody producing hybridoma, or the antibody itself.

Immunogens and Antigens (Recombinant Proteins, His Tags)

For antibody production, screening and characterization various recombinant and purified proteins were prepared using techniques known by those of skill in the art.

Nucleic acid molecules encoding Lp-PLA2 were inserted into various expression vectors to produce recombinant proteins. These nucleic acid sequences were isolated by PCR using the primers which are routine to design. Lp-PLA2 proteins may include naturally occurring variants (e.g. allelic variants, SNPs). These variant sequences, and antibodies which bind to them are considered part of the invention as described herein.

Immunization

Immunogens for the LpPLA2.A-series mAbs was Lp-PLA2 from insect cells. Immunogens for the LpPLA2.B-series mAbs was Lp-PLA2 from insect cells. Immunogens for the LpPLA2.C-series mAbs was Lp-PLA2 from insect cells and mammalian cells.

For each series, mice (Balb/c, FVB or C3H) were immunized using techniques routinely employed by those of skill in the art.

Hybridoma Fusion

Hybridomas were made using techniques routinely used by those of skill in the art. After the final immunization, mice were sacrificed and draining lymph node (popliteal) tissue was collected by sterile dissection. Lymph node cells were dispersed using a tissue grinder followed by pressing through a sterile sieve into DMEM and removing T-cells via anti-CD90 (Thy1.2) coated magnetic beads.

These primary B-cell enriched lymph node cells were then immortalized by electro-cell fusion with the continuous myeloma cell line P3x63Ag8.653 (Kearney, J. F. et al., J. Immunology 123: 1548-1550, 1979). The myeloma and B-cells were pooled at a 1:1 ratio for the fusion. These fusion cultures were distributed at 2 million cells per plate into wells of 96 well culture plates. The remainder of the cells was cultured in bulk in HAT selection medium for several days and cryopreserved for future screens. Successfully fused cells were selected by culturing in selection medium (DMEM/15% FBS) containing 2.85 µM Azaserine, 50 µM Hypoxanthine (HA) or 50 µM Hypoxanthine, 0.2 µM Aminopterin, 8 µM Thymidine (HAT) supplemented with recombinant human IL-6 at 0.5 ng/mL. Cultures were transitioned into medium (DMEM/10% FBS) without selection and IL-6 supplements for continued expansion and antibody production.

The resulting murine B-cell hybridoma cultures were expanded using standard tissue culture techniques. Selected hybridomas were cryopreserved in fetal bovine serum (FBS) with 10% DMSO and stored in Liquid Nitrogen at −196° C. to assure maintenance of viable clone cultures.

Example 2

Characterization of Antibodies

Pairing of Lp-PLA2 Antibodies

To evaluate and characterize Lp-PLA2 antibodies of the present invention a luminex pairing assay was performed as set forth in Miller et al., Journal of Immuno Methods 365 (2011) 118-125, the content of which is hereby incorporated by reference in its entirety. Anti-Lp-PLA2 antibodies 2C10 and 4B4 (diaDexus, South San Francisco, Calif.) were used as reference antibodies. The pairing assay identified antibodies which bound Lp-PLA2 antigen and if antibodies bound unique epitopes or competed for binding to epitopes on Lp-PLA2.

Raw data was sorted as set forth in Miller et al and the pattern of reactivities demonstrated that Lp-PLA2 antibodies group into several 'bins'.

Bin 1 comprises B38, and B229;

Bin 2 comprises B144, B6, B31, B40, B44, B48, B71, B78, B81, B154, B194, B213, B224, B228, B281, and C10;

Bin 3 comprises B159, A201, B17, B26, B69, B130, B132, B142, B201, B236, B238, B248, B251, B280, and C8;

Bin 4 comprises B200, A7, A8, 5, B149, B179, B195, B235, B241, B266, C2, C9, and C12;

Bin 5 comprises C5, C16, C18, and C19.

Antibodies which group into the same bin have similar epitope specificities, meaning they compete for binding to an Lp-PLA2 epitope.

Sandwich ELISA Screening of Hybridomas Producing Lp-PLA2 Specific Antibodies

Plates were coated with polyclonal IgG goat anti-Lp-PLA2 antibody (10 ug/mL in PBS; 100 uL/well) by incubating overnight at 4° C. The plate wells were flicked dry and non-specific binding capacity was blocked by filling the wells (300 uL/well) with TBST/0.5% bovine serum albumin (TBST/BSA) and incubating for >30 minutes at room temperature (RT). The plate was washed with standard kit wash. Recombinant Lp-PLA2 (rLpPLA2) antigen and serum Lp-PLA2 (serumLpPLA2) were diluted 1:5 in TBST BSA+ CHAPS. Either rLpPLA2, serumLpPLA2 or control (TBST BSA+CHAPS) mixtures were added to the plate at 100 uL/well. Plates were incubated for >1 hour at RT with shaking. The plate was then washed with standard kit wash. One hundred uL of test antibodies of the present invention (pre-diluted in TBST BSA+CHAPS to 10 ug/mL) were added to wells and incubated for >1 hour at RT with shaking. The plate was then washed with standard kit wash. One hundred uL of alkaline phosphatase conjugated MsIgG (Jackson P/N 115-055-003) were added to wells and incubated for >1 hour at RT with shaking. The plate was then washed with standard kit wash. One hundred uL of alkaline phosphatase substrate para-nitrophenylphosphate (pNPP) at 1 mg/mL in 1M Diethanolamine buffer was added to each well and incubated at RT with shaking. The enzymatic reaction was quantified by measuring the solution's absorbance at 405 nm wavelength (SpectraMaxPlus, Softmax Pro) at development times of 80 minutes. Lp-PLA2 antibodies that produced an absorbance value of greater than 0.50 for LpPLA2 antigens and not the control were considered Lp-PLA2-specific.

The table below demonstrates that all anti-Lp-PLA2 antibodies except B500.6, B501.5, and C203.1 specifically bound Lp-PLA2.

| Antibody | rLpPLA2 | Serum Lp-PLA2 | No Antigen |
|---|---|---|---|
| 2C10 | 1.1012 | 1.0014 | 0.2903 |
| 4B4 | 1.4495 | 1.3081 | 0.2900 |
| B5.2 | 1.3435 | 1.1552 | 0.2988 |
| B17.2 | 0.7223 | 0.5737 | 0.2869 |
| B38.2 | 0.7550 | 0.6449 | 0.2851 |
| B144.2 | 1.3467 | 1.1619 | 0.2867 |
| B159.2 | 1.3674 | 0.8285 | 0.2970 |
| B200.2 | 1.7834 | 1.3912 | 0.2966 |
| B201.1 | 0.5968 | 0.5459 | 0.2852 |
| B229.1 | 0.6547 | 0.5958 | 0.2782 |
| B500.6 | 0.5894 | 0.5792 | 0.5792 |
| B501.5 | 0.4293 | 0.2579 | 0.2784 |
| C201.1 | 0.7894 | 0.5916 | 0.2761 |
| C203.1 | 0.2937 | 0.2626 | 0.2815 |

Lp-PLA2 MAb Isotypes

The isotypes of the anti-Lp-PLA2 MAbs were determined using commercially available mouse monoclonal antibody isotyping immunoassay test kits (IsoStrip, Roche Diagnostic Corp., Indianapolis, Ind.). Lp-PLA2 antibodies B5.2, B17.2, B38.2, B144.2, B159.2, B200.2, B201.1, B229.1, B500.6, B501.5, C201.1, and C203.1 are all IgG1 kappa isotype.

Structural Characterization of the Lp-PLA2 Antibody IgG Heavy and Light Chains

The nucleotide sequences of the variable regions of the IgG heavy and light chains of antibodies from hybridomas B38, B144, B159 and B200 were determined by McLab (South San Francisco, Calif.). The sequences of the heavy and light chains of the antibodies were evaluated to determine the CDR regions using techniques known by those of skill in the art, such as the Kabat system of CDR region determination (Kabat et al. Sequences of proteins of immunological interest, 5th edition, Public Health Service, National Institutes of Health, Bethesda, Md.) and those described by Clothia et al., J. Mol. Biol. (1987) 196, 901-917, Chothia et al., J Mol Biol. (1998) 278, 457-479, and Chothia et al. J Mol Biol. (1992) 227, 799-817.

Nucleic acid and amino acid sequences of the light chain variable region of LpPLA2.B38 are show in SEQ ID NO: 1 and 2, respectively. Light chain CDR1, CDR2 and CDR3 regions are shown in SEQ ID NO: 3, 4 and 5, respectively.

```
LpPLA2.B38_LCVD.na, SEQ ID NO: 1:
GGGATATTGTGCTCACCCAAACTCACAAATTCATGTCCACATCAGTAGGAGACAGGGTCAACAT

CACCTGCAAGGCCAGTCAGGATGTGAATACTGCTGTAGCCTGGTATCAACAAAAACCAGGGCAA

TCTCCTAAACTACTGATTAAGTGGGCATCCACCCGGCACACTGGAGTCCCTGATCGCTTCACAG

GCAGTGGATCTGGGACAGATTATATTTTCACCATCAGCAGTGTGCAGGCTGAAGACCTGGCACT

TTATTACTGTCAGCAACATTATAGCACTCCGTGGACGTTCGGTGGAGGCACCAAGCTGGAAATC

AAACGGGCTGATGCTGCACCAACTGTATCCACC

LpPLA2.B38_LCVD.aa, SEQ ID NO: 2:
DIVLTQTHKFMSTSVGDRVNITCKASQDVNTAVAWYQQKPGQSPKLLIKWASTRHTGVPDRFTG

SGSGTDYIFTISSVQAEDLALYYCQQHYSTPWTFGGGTKLEIKRADAAPTVST

LpPLA2.B38_LCVD_CDR1, SEQ ID NO: 3:
KASQDVNTAVA

LpPLA2.B38_LCVD_CDR2, SEQ ID NO: 4:
WASTRHT

LpPLA2.B38_LCVD_CDR3, SEQ ID NO: 5:
QQHYSTPWT
```

Nucleic acid and amino acid sequences of the heavy chain variable region of LpPLA2.B38 are shown in SEQ ID NO: 6 and 7, respectively. Heavy chain CDR1, CDR2 and CDR3 regions are shown in SEQ ID NO: 8, 9 and 10, respectively.

```
LpPLA2.B38_HCVD.na, SEQ ID NO: 6:
CTTCCGGAGGTGAAGCTGGAGGAGTCTGGACCTGAGCTGAAGAAGCCTGGAGAGACAGTCAAGA

TCTCCTGCAAGGCTTCTGGTTATACCTTCACAGACTATTCAGTGCACTGGGTGAAGCAGGCTCC

AGGAAAGGGTTTAAAGTGGATGGGCTGGATAAACACTGACACTGGTGAGCCAACATTTGCAGAT

GACTTCAAGGGACGGTTTGCCTTCTCTTTGGAAACCTCTACCAGCACTGCCTATTTGCAGATCA

ACAACCTCAAAAATGAGGACACGGCTACATATTTCTGTGCTAGGGGAGATAACTACCTATATTA

CTATACTATGGACTACTGGGGTCAAGGAATATCAGTCACCGTCTCCTCAGCCAAAACGACACCC

CCATCTGTCTATTCC
```

```
LpPLA2.B38_HCVD.aa, SEQ ID NO: 7:
LPEVKLEESGPELKKPGETVKISCKASGYTFTDYSVHWVKQAPGKGLKWMGWINTDTGEPTFAD

DFKGRFAFSLETSTSTAYLQINNLKNEDTATYFCARGDNYLYYYTMDYWGQGISVTVSSAKTTP

PSVYS

LpPLA2.B38_HCVD_CDR1, SEQ ID NO: 8:
GYTFTDYSVH

LpPLA2.B38_HCVD_CDR2, SEQ ID NO: 9:
WINTDTGEPTFADDFKG

LpPLA2.B38_HCVD_CDR3, SEQ ID NO: 10:
GDNYLYYYTMDY
```

Nucleic acid and amino acid sequences of the light chain variable region of LpPLA2.B144 are shown in SEQ ID NO: 11 and 12, respectively. Light chain CDR1, CDR2 and CDR3 regions are shown in SEQ ID NO: 13, 14 and 15, respectively.

```
LpPLA2.B144_LCVD.na, SEQ ID NO: 11:
GGGATATTGTGATGACCCAAACTCCAGCTTCTTTGGCTGTGTCTCTAGGGCAGAGGGCCACCAT

CTCCTGCAGAGCCAGCGAAAGTGTTGATAATTATGGCATTAGTTTTATGCACTGGTTCCAACAG

AAACCAGGACAGCCACCCAAACTCCTCATCTATGCTGCATCCAACCAAGGATCCGGGGTCCCTG

CCAGGTTTAGTGGCAGTGGGTCTGGGACAGACTTCAGCCTCAACATCCATCCTATGGAGGAGGA

TGATACTGCAATGTATTTCTGTCAGCAAAGTAAGGAGGTTCCATTCACGTTCGGCTCGGGGACA

AAGTTGGAAATAAAACGGGCTGATGCTGCACCAACTGTATCCACC

LpPLA2.B144_LCVD.aa, SEQ ID NO: 12:
DIVMTQTPASLAVSLGQRATISCRASESVDNYGISFMHWFQQKPGQPPKLLIYAASNQGSGVPA

RFSGSGSGTDFSLNIHPMEEDDTAMYFCQQSKEVPFTFGSGTKLEIKRADAAPTVST

LpPLA2.B144_LCVD_CDR1, SEQ ID NO: 13:
RASESVDNYGISFMH

LpPLA2.B144_LCVD_CDR2, SEQ ID NO: 14:
AASNQGS

LpPLA2.B144_LCVD_CDR3, SEQ ID NO: 15:
QQSKEVPFT
```

Nucleic acid and amino acid sequences of the heavy chain variable region of LpPLA2.B144 are shown in SEQ ID NO: 16 and 17, respectively. Heavy chain CDR1, CDR2 and CDR3 regions are shown in SEQ ID NO: 18, 19 and 20, respectively.

```
LpPLA2.B144 HCVD.na, SEQ ID NO: 16:
CTTCCGGAGGTACAGCTGGAGCAGTCAGGACCTGAACTGGTGAAGCCTGGGGCTTCAGTGAAGA

TATCCTGCAAGACTTCTGGATACACATTCACTGAATACACCATGCACTGGGTGAAACAGAGCCA

TGGAAAGAGCCCTGAGTGGATTGGAGGTATTAATCCTAACAATGGTTATGCTAGGTACAACCAG

AAGTTCAAGGGCAAGGCCACATTGACTGTAGACAAGTCCTCCAGCACAGCCTCCATGGAGCTCC

GCAGCCTGACATCTGAGGATTCTGCAGTCTGTTACTGTGCAAGAGGGCCCTATTACTACGGTAG

TAGCCACTATGCTATGGACTACTGGGGTCAAGGAACCTCAGTCACCGTCTCCTCAGCCAAAACG

ACACCCCCATCTGTCTATTCC
```

-continued

```
LpPLA2.B144_HCVD.aa, SEQ ID NO: 17:
LPEVQLEQSGPELVKPGASVKISCKTSGYTFTEYTMHWVKQSHGKSPEWIGGINPNNGYARYNQ

KFKGKATLTVDKSSSTASMELRSLTSEDSAVCYCARGPYYYGSSHYAMDYWGQGTSVTVSSAKT

TPPSVYS

LpPLA2.B144_HCVD_CDR1, SEQ ID NO: 18:
GYTFTEYTMH

LpPLA2.B144_HCVD_CDR2, SEQ ID NO: 19:
GINPNNGYARYNQKFKG

LpPLA2.B144_HCVD_CDR3, SEQ ID NO: 20:
GPYYYGSSHYAMDY
```

Nucleic acid and amino acid sequences of the light chain variable region of LpPLA2.B159 are shown in SEQ ID NO: 21 and 22, respectively. Light chain CDR1, CDR2 and CDR3 regions are shown in SEQ ID NO: 23, 24 and 25, respectively.

```
LpPLA2.13159_LCVD.na, SEQ ID NO: 21:
GGGATATTGTGATGACCCAAACTCCACTCACTTTGTCGGTTACCATTGGACAACCAGCCTCTAT

TTCTTGCAAGTCAAGTCAGAGCCTCTTATATATTAATGGAAAAACCTATTTGAATTGGTTATTA

CAGAGGCCAGGCCAGTCTCCAAAGCGCCTAATCTATCTGGTGTCTAAACTGGACTCTGGAGTCC

CTGACAGGTTCACTGGCAGTGGATCGGGAACAGATTTTACACTGAAAATCAGCAGAGTGGAGGC

TGAGGATTTGGGAATTTATTACTGCGTGCAAGGTACACATTTTCCATTCACGTTCGGCTCGGGG

ACAAAGTTGGAAATAAAACGGGCTGATGCTGCACCAACTGTATCCACC

LpPLA2.B159 LCVD.aa, SEQ ID NO: 22:
DIVMTQTPLTLSVTIGQPASISCKSSQSLLYINGKTYLNWLLQRPGQSPKRLIYLVSKLDSGVP

DRFTGSGSGTDFTLKISRVEAEDLGIYYCVQGTHFPFTFGSGTKLEIKRADAAPTVST

LpPLA2.B159_LCVD_CDR1, SEQ ID NO: 23:
KSSQSLLYINGKTYLN

LpPLA2.B159_LCVD_CDR2, SEQ ID NO: 24:
LVSKLDS

LpPLA2.B159_LCVD_CDR3, SEQ ID NO: 25:
VQGTHFPFT
```

Nucleic acid and amino acid sequences of the heavy chain variable region of LpPLA2.B159 are shown in SEQ ID NO: 26 and 27, respectively. Heavy chain CDR1, CDR2 and CDR3 regions are shown in SEQ ID NO: 28, 29 and 30, respectively.

```
LpPLA2.B159_HCVD.na, SEQ ID NO: 26:
CTTCCGCAAGTAAAGCTGGAGGAGTCTGGACCTGAGCTGGTGAAGCCTGGAGCTTCAATGCAGA

TATCCTGCAAGGCTTCTGGTTACTCATTCACTGTCTACACCATGAACTGGGTGAAGCAGAGCCA

TGGAAAGAACCTTGAGTGGGTTGGACTTATTAATCCTTTCAATGGTGATACTACTTACAACCAG

AAGTTCAAGGGCAAGGCCACATTAACTGTAGACAAGTCATCCAGCACAGCCTACATGGACCTCC

TCAGTCTGACATCTGACGACTCTGCAGTCTATTACTGTGTAAGATTTTGGGAAGGAATTGACTT

CTGGGGCCAAGGCACCACTCTCACAGTCTCCTCAGCCAAAACNACACCCCCATCTGTCTATTCC

LpPLA2.B159_HCVD.aa, SEQ ID NO: 27:
LPQVKLEESGPELVKPGASMQISCKASGYSFTVYTMNWVKQSHGKNLEWVGLINPFNGDTTYNQ

KFKGKATLTVDKSSSTAYMDLLSLTSDDSAVYYCVRFWEGIDFWGQGTTLTVSSAKTTPPSVYS
```

```
LpPLA2.B159_HCVD_CDR1, SEQ ID NO: 28:
GYSFTVYTMN

LpPLA2.B159_HCVD_CDR2, SEQ ID NO: 29:
LINPFNGDTTYNQKFKG

LpPLA2.B159_HCVD_CDR3, SEQ ID NO: 30:
FWEGIDF
```

Nucleic acid and amino acid sequences of the light chain variable region of LpPLA2.B200 are shown in SEQ ID NO: 31 and 32, respectively. Light chain CDR1, CDR2 and CDR3 regions are shown in SEQ ID NO: 33, 34 and 35, respectively.

```
LpPLA2.B200_LCVD.na, SEQ ID NO: 31:
GGGATATTGTGCTCACCCAGTCTCCACTCACTTTGTCGGTTACCATTGGACAACCAGCCTCTAT

CTCTTGCAAGTCAAGTCAGAGCCTCTTATATAGTAATGGAAAATCCTTTTTGAATTGGTTATTA

CAGAGGCCAGGCCAGTCTCCAAAGCGCCTAATCTATCTGGTGTCTAAATTGGACTCTGGAGTCC

CTGACAGGTTCACTGGCTGTGGATCAGGAAAAGATTTTACACTGAAAATCAGCAGAGTGGAGGC

TGAGGATTTGGGAGTTTATTACTGCGTGCAAGGTACACATTTTCCTCAGACGTTCGGTGGAGGC

ACCAAGCTAGAAATCAAACGGGCTGATGCTGCACCAACTGTATCCACC

LpPLA2.B200_LCVD.aa, SEQ ID NO: 32:
DIVLTQSPLTLSVTIGQPASISCKSSQSLLYSNGKSFLNWLLQRPGQSPKRLIYLVSKLDSGVP

DRFTGCGSGKDFTLKISRVEAEDLGVYYCVQGTHFPQTFGGGTKLEIKRADAAPTVST

LpPLA2.B200_LCVD_CDR1, SEQ ID NO: 33:
KSSQSLLYSNGKSFLN

LpPLA2.B200_LCVD_CDR2, SEQ ID NO: 34:
LVSKLDS

LpPLA2.B200_LCVD_CDR3, SEQ ID NO: 35:
VQGTHFPQT
```

Nucleic acid and amino acid sequences of the heavy chain variable region of LpPLA2.B200 are shown in SEQ ID NO: 36 and 37, respectively. Heavy chain CDR1, CDR2 and CDR3 regions are shown in SEQ ID NO: 38, 39 and 40, respectively.

```
LpPLA2.B200_HCVD.na, SEQ ID NO: 36:
CTTCCGGAAGTGCAGCTGGAGCAGTCAGGACCTGGCCTAGTGCAGCCCTCACAGAGCCTGTCCA

TCACCTGCACAGTCTCTGGTTTCTCATTAACCACCTATGATGTACTCTGGGTGCGCCAGTCTCC

AGGAAAGGGTCTGGAGTGGCTGGGAATTATCTGGAGTGGTGGAAGCGCAGACTATAATGCAGCT

TTCATCTCCAGACTGAGCATCACTAAGGACAATTCCAAGAGCCAAGTTTTCTTTGAAATGAACA

GTCTGCAAGCTAATGACACAGCCATATATTACTGTGCCAGTTACTACATCAATGCTCTGGACTA

CTGGGGGCAAGGAACCTCAGTCACCGTCTCCTCAGCCAAAACGACACCCCCATCTGTCTATTCC

LpPLA2.B200_HCVD.aa, SEQ ID NO: 37:
LPEVQLEQSGPGLVQPSQSLSITCTVSGFSLTTYDVLWVRQSPGKGLEWLGIIWSGGSADYNAA

FISRLSITKDNSKSQVFFEMNSLQANDTAIYYCASYYINALDYWGQGTSVTVSSAKTTPPSVYS

LpPLA2.B200_HCVD_CDR1, SEQ ID NO: 38:
GFSLTTYDVL

LpPLA2.B200_HCVD_CDR2, SEQ ID NO: 39:
IIWSGGSADYNAAFIS

LpPLA2.B200_HCVD_CDR3, SEQ ID NO: 40:
YYINALDY
```

We claim:

1. An isolated antibody or antigen binding fragment thereof, wherein the antibody or antigen binding fragment binds to Lp-PLA2 and comprises:
   a light chain variable region comprising an amino acid sequence selected from the group consisting of SEQ ID NOs: 2, 12, and 22; and
   a heavy chain variable region.

2. An isolated antibody or antigen binding fragment thereof, wherein the antibody or antigen binding fragment binds to Lp-PLA2 and comprises:
   a light chain variable region; and
   a heavy chain variable region comprising an amino acid sequence selected from the group consisting of SEQ ID NOs: 7, 17, and 27.

3. The antibody or antigen binding fragment of claim 1, wherein the light chain variable region comprises the amino acid sequence of SEQ ID NO: 2; and wherein the heavy chain variable region comprises the amino acid sequence of SEQ ID NO: 7.

4. The antibody or antigen binding fragment of claim 1, wherein the light chain variable region comprises the amino acid sequence of SEQ ID NO: 12; and wherein the heavy chain variable region comprises the amino acid sequence of SEQ ID NO: 17.

5. The antibody or antigen binding fragment of claim 1, wherein the light chain variable region comprises the amino acid sequence of SEQ ID NO: 22; and wherein the heavy chain variable region comprises the amino acid sequence of SEQ ID NO: 27.

6. The antibody or antigen binding fragment of claim 1, wherein the antibody or antigen binding fragment is a monoclonal antibody.

7. The antibody or antigen binding fragment of claim 1, wherein the antibody or antigen binding fragment is a chimeric antibody.

8. An isolated monoclonal antibody or antigen binding fragment thereof that binds to Lp-PLA2, the antibody or antigen binding fragment comprising: a light chain variable region comprising CDR1, CDR2 and CDR3 sequences; and a heavy chain variable region comprising CDR1, CDR2, CDR3 sequences, wherein:
   (a) the light chain variable region comprises:
      a light chain CDR1 having an amino acid sequence of SEQ ID NO: 3,
      a light chain CDR2 having an amino acid sequence of SEQ ID NO: 4,
      a light chain CDR3 having an amino acid sequence of SEQ ID NO: 5; and
   (b) the heavy chain variable region comprises:
      a heavy chain CDR1 having an amino acid sequence of SEQ ID NO: 8,
      a heavy chain CDR2 having an amino acid sequence of SEQ ID NO: 9,
      a heavy chain CDR3 having an amino acid sequence of SEQ ID NO: 10.

9. The antibody of claim 8, wherein the antibody is a humanized antibody or a chimeric antibody.

10. An isolated monoclonal antibody or antigen binding fragment thereof that binds to Lp-PLA2, the antibody or antigen binding fragment comprising: a light chain variable region comprising CDR1, CDR2 and CDR3 sequences; and a heavy chain variable region comprising CDR1, CDR2, CDR3 sequences, wherein:
  (a) the light chain variable region comprises:
    a light chain CDR1 having an amino acid sequence of SEQ ID NO: 13,
    a light chain CDR2 having an amino acid sequence of SEQ ID NO: 14,
    a light chain CDR3 having an amino acid sequence of SEQ ID NO: 15; and
  (b) the heavy chain variable region comprises:
    a heavy chain CDR1 having an amino acid sequence of SEQ ID NO: 18,
    a heavy chain CDR2 having an amino acid sequence of SEQ ID NO: 19,
    a heavy chain CDR3 having an amino acid sequence of SEQ ID NO: 20.

11. The antibody of claim 10, wherein the antibody is a humanized antibody or a chimeric antibody.

12. An isolated monoclonal antibody or antigen binding fragment thereof that binds to Lp-PLA2, the antibody or antigen binding fragment comprising: a light chain variable region comprising CDR1, CDR2 and CDR3 sequences; and a heavy chain variable region comprising CDR1, CDR2, CDR3 sequences, wherein:
  (a) the light chain variable region comprises:
    a light chain CDR1 having an amino acid sequence of SEQ ID NO: 23,
    a light chain CDR2 having an amino acid sequence of SEQ ID NO: 24,
    a light chain CDR3 having an amino acid sequence of SEQ ID NO: 25; and
  (b) the heavy chain variable region comprises:
    a heavy chain CDR1 having an amino acid sequence of SEQ ID NO: 28,
    a heavy chain CDR2 having an amino acid sequence of SEQ ID NO: 29,
    a heavy chain CDR3 having an amino acid sequence of SEQ ID NO: 30.

13. The antibody of claim 12, wherein the antibody is a humanized antibody or a chimeric antibody.

\* \* \* \* \*